US012649007B2

(12) United States Patent  (10) Patent No.: US 12,649,007 B2
Orlans et al.  (45) Date of Patent: Jun. 9, 2026

(54) GENE THERAPY FOR RETINAL DISEASE

(71) Applicant: Oxford University Innovation Limited, Oxford (GB)

(72) Inventors: Harry O. Orlans, Oxford (GB); Robert E. Maclaren, Oxford (GB); Michelle E. McClements, Oxford (GB); Alun R Barnard, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1251 days.

(21) Appl. No.: 17/288,574

(22) PCT Filed: Oct. 25, 2019

(86) PCT No.: PCT/GB2019/053036
§ 371 (c)(1),
(2) Date: Nov. 3, 2021

(87) PCT Pub. No.: WO2020/084318
PCT Pub. Date: Apr. 30, 2020

(65) Prior Publication Data
US 2022/0249702 A1     Aug. 11, 2022

(30) Foreign Application Priority Data

Oct. 26, 2018     (GB) ...................................... 1817469

(51) Int. Cl.
*A61K 48/00*     (2006.01)
*A61P 27/02*     (2006.01)
*C12N 15/113*     (2010.01)
*C12N 15/86*     (2006.01)
(52) U.S. Cl.
CPC .......... *A61K 48/0066* (2013.01); *A61P 27/02* (2018.01); *C12N 15/113* (2013.01); *C12N 15/86* (2013.01); *C12N 2310/141* (2013.01); *C12N 2750/14043* (2013.01); *C12N 2750/14071* (2013.01)
(58) Field of Classification Search
CPC ... A61K 48/0066; A61K 48/005; A61P 27/02; C12N 15/113; C12N 15/86; C12N 2310/141; C12N 2750/14043; C12N 2750/14071; C12N 15/111; C12N 2320/31; C12N 2320/34; C12N 2330/51; C12N 2750/14143
See application file for complete search history.

(56) References Cited

FOREIGN PATENT DOCUMENTS

| | | |
|---|---|---|
| JP | 2017-509632 A | 4/2017 |
| WO | 2010/029303 A1 | 3/2010 |
| WO | 2011/114106 A2 | 9/2011 |
| WO | 2015/084254 A1 | 6/2015 |
| WO | 2015/143418 A2 | 9/2015 |
| WO | WO-2017018937 A1 * | 2/2017 ........... C12N 15/111 |
| WO | 2017/151823 A1 | 9/2017 |
| WO | 2017/216560 A1 | 12/2017 |

OTHER PUBLICATIONS

Curtis, Helen J., et al. "Knockdown and replacement therapy mediated by artificial mirtrons in spinocerebellar ataxia 7." Nucleic Acids Research 45.13 (2017): 7870-7885. (Year: 2017).*
O'Reilly, Mary, et al. "RNA interference-mediated suppression and replacement of human rhodopsin in vivo." The American Journal of Human Genetics 81.1 (2007): 127-135.) (Year: 2007).*
International Search Report and Written Opinion for WO 2020/084318 (PCT/GB2019/053036), dated Jan. 24, 2020, pp. 1-10.
UK Search Report for GB 1817469.8, dated Apr. 5, 2019, pp. 1-4.
Altschul S. F., (1993) J Mol Evol 36:290-300, "A Protein Alignment Scoring System Sensitive at All Evolutionary Distances", pp. 1-11.
Altschul, S, F et al. (1990) J Mol Biol 215:403-10, "Basic Local Alignment Search Tool", pp. 1-8.
Choi et al. (Curr Gene Ther. 2005; 5(3); 299-310), "AAV Hybrid Serotypes: Improved Vectors for Gene Delivery", pp. 1-20.
Coura and Nardi, Virology Journal, 2007, 4:99, "The state of the art of adeno-associated virus-based vectors in gene therapy", pp. 1-7.
Devereux et al. (1984) Nucleic Acids Research 12, 387-395), "A comprehensive set of sequence analysis programs for the VAX", pp. 1-9.
Laughlin et al. 1979, PNAS, 76:5567-5571, "Spliced adenovirus-associated virus RNA", pp. 1-5.
Patricio et al. (2017), Mol. Ther.—Nucleic Acids 6: 198-208, "Inclusion of the Woodchuck Hepatitis Virus Posttranscriptional Regulatory Element Enhances AAV2-Driven Transduction of Mouse and Human Retina", pp. 1-11.
Schwarz et al. (2003, Cell 115(2): 199-208, "Asymmetry in the Assembly of the RNAi Enzyme Complex", pp. 1-10.
Wu et al. (Molecular Therapy. 2006; 14(3), 316-327, "Adeno-associated Virus Serotypes: Vector Toolkit for Human Gene Therapy", pp. 1-12.
Cideciyan et al., P.N.A.S., vol. 115, Sep. 2018, pp. E8547-E8556, "Mutation-independent rhodopsin gene therapy by knockdown and replacement with a single AAV vector", pp. 1-10.
Murray et al., Inv. Ophthalmol. Vis. Sci., vol. 56, 2015, pp. 6362-6375, "Allele-Specific Inhibition of Rhodopsin With an Anti-sense Oligonucleotide Slows Photoreceptor Cell Degeneration", pp. 1-14.
Curtis et al., Nucl. Acids Res., vol. 45, 2017, pp. 7870-7885, "Knockdown and replacement therapy mediated by artificial mirtrons in spinocerebellar ataxia7", pp. 1-16.

(Continued)

*Primary Examiner* — Ekaterina Poliakova-Georgantas
*Assistant Examiner* — John Charles McKillop
(74) *Attorney, Agent, or Firm* — Thomas|Horstemeyer, LLP

(57) ABSTRACT
A method of treating a retinal disease in a subject in need thereof, the method comprising administering to the subject a vector that comprises a mirtron for knocking down expression of a target gene expressed in the retina and a gene therapy vector comprising a mirtron for rhodopsin knockdown.

8 Claims, 49 Drawing Sheets

Specification includes a Sequence Listing.

(56)     References Cited

OTHER PUBLICATIONS

Kock et al., Nucl. Acids Res., vol. 43, 2015, pp. 6568-6578, "Functional VEGFA knockdown with artificial 3'-tailed mirtrons defined by 5' splice site and branch point", pp. 1-11.

Seow et al., RNA, vol. 18, 2012, pp. 1328-1337, "Artificial mirtron-mediated gene knockdown: Functional DMPK silencing in mammalian cells", pp. 1-11.

Berezikov et al., Mol. Cell, vol. 28, 2007, pp. 328-336, "Mammalian Mirtron Genes", pp. 1-14.

Ladewig et al., Genome Res., vol. 22, 2012, pp. 1634-1645, "Discovery of hundreds of mirtrons in mouse and human small RNA data", pp. 1-12.

Fischer et al. Molecular Therapy, vol. 25, No. 8, 2017, pp. 1854-1865, "Codon-Optimized RPGR Improves Stability and Efficacy of AAV8 Gene Therapy in Two Mouse Models ofX-Linked Retinitis Pigmentosa", pp. 1-12.

Fairbrother et al., SCIENCE, vol. 297 (5583), 2002, 1007-1013. "Predictive Identification of Exonic Splicing Enhancers In Human Genes", pp. 1-8.

Curtis et al., WIREs, RNA, 3, 617-632, (2012), "Mirtrons, an emerging class of atypical miRNA", pp. 1-16.

International Preliminary Report on Patentability for WO 2020/084318 (PCT/GB2019/053036), dated Apr. 27, 2021, pp. 1-7.

Webpage: http://genes.mit.edu/burgelab/rescue-ese/, pp. 1-2, no date available.

Webpage: http://www.ncbi.nlm.nih.gov/, National Center for Bio-technology Information, "A new NIH initiative to end structural racism and achieve racial equity in the biomedical research enter-prise", pp. 1-2, no date available.

Webpage: Spliceport, http://spliceport.cbcb.umd.edu, "SplicePort: An Interactive Splice Site Analysis Tool", 1 page.

Japanese Office Action for Patent Application No. 2021-523068, dated Oct. 31, 2023, pp. 1-5 (Translation Included).

Mao et al., "Long-Term Rescue of Retinal Structure and Function by Rhodopsin RNA Replacement with a Single Adeno-Associated Viral Vector in P23H RHO Transgenic Mice", Human Gene Therapy 23:356-366 (Apr. 2012), pp. 1-12.

* cited by examiner

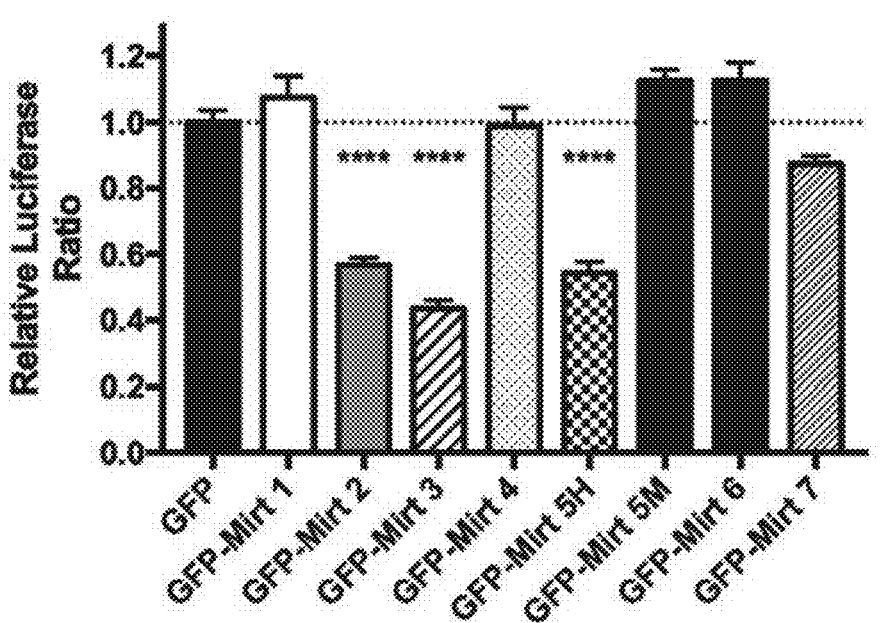
FIG. 11A
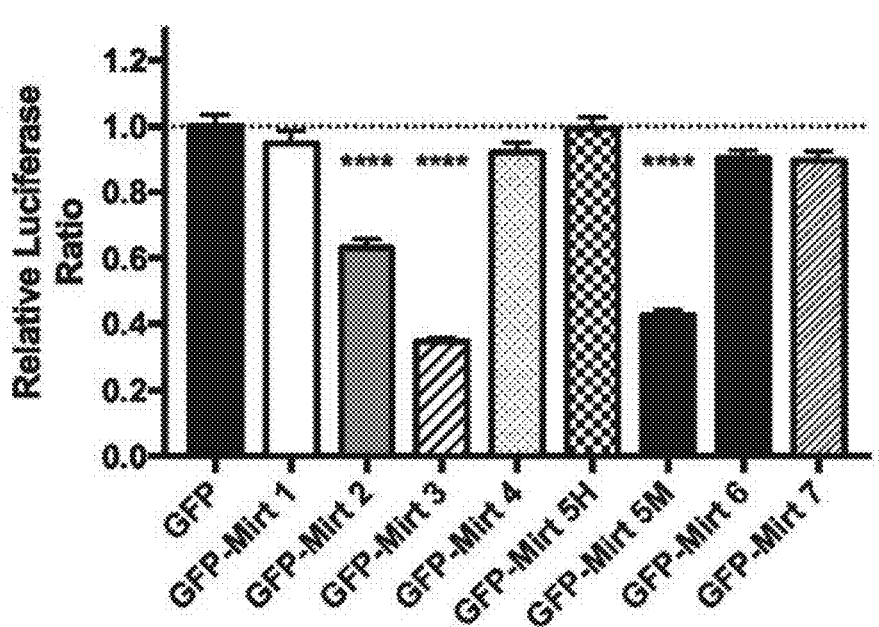
FIG. 11B

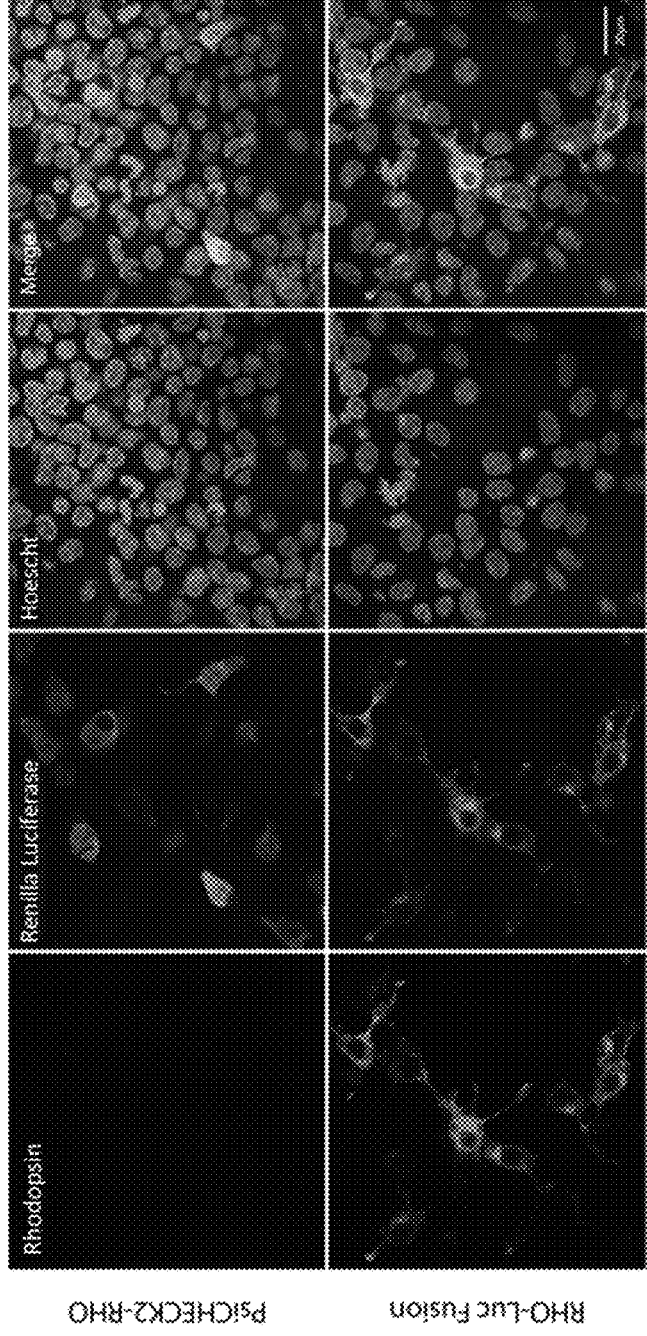
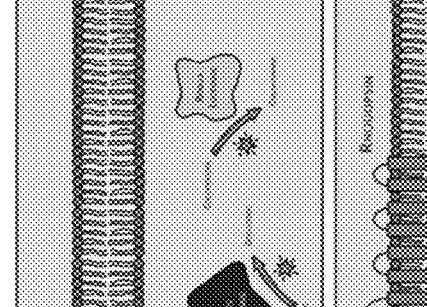
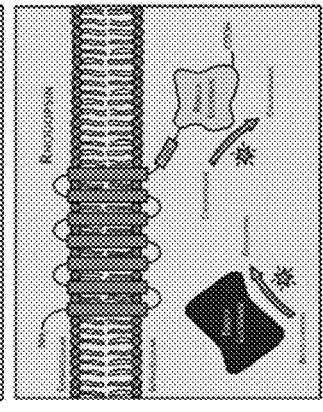
FIG. 15

```
                  ACAAGA                          TTCGAA
                  TACAAG                   GTCAAG
                ACTACA                    TGAAGT
                AACTAC                    CTGAAG
       TGACGGGAACTACAAGACCCGCGCTGAAGTCAAGTTCGAAG    SEQ ID NO:37
       .|.........|..........|..........|..........
         40        30         20         10
```

```
                                             GAGGAT
                           TGAAGG          GGAGGA
                           CTGAAG          AAGGAG
       GTGACACCCTGGTGAATAGAATCGAGCTGAAGGGCATTGACTTTAAGGAGGAT   SEQ ID
       .........|.........|.........|.........|.........|...    NO:38
                10        20        30        40        50
```

FIG. 22B

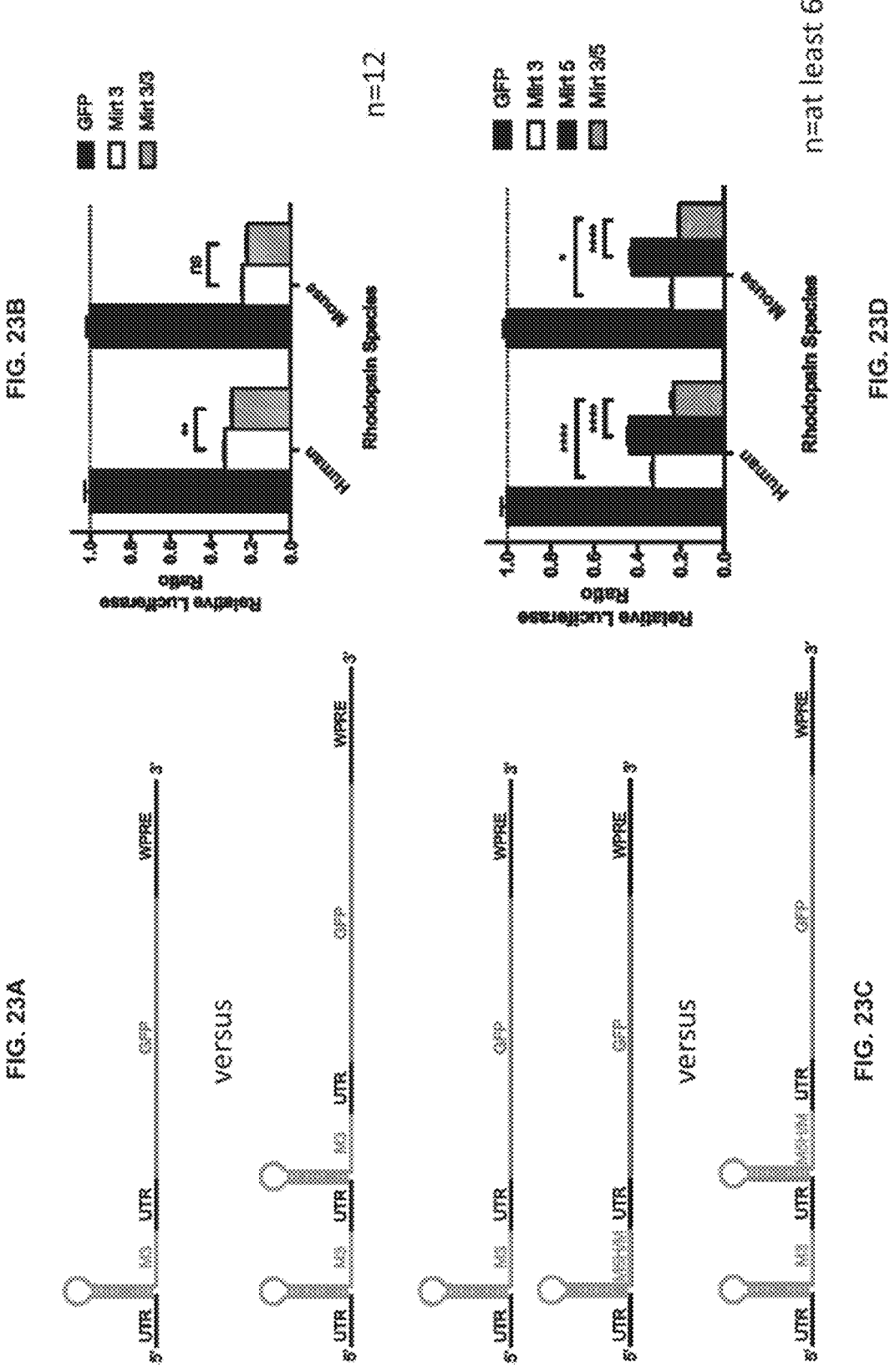

FIG. 25B

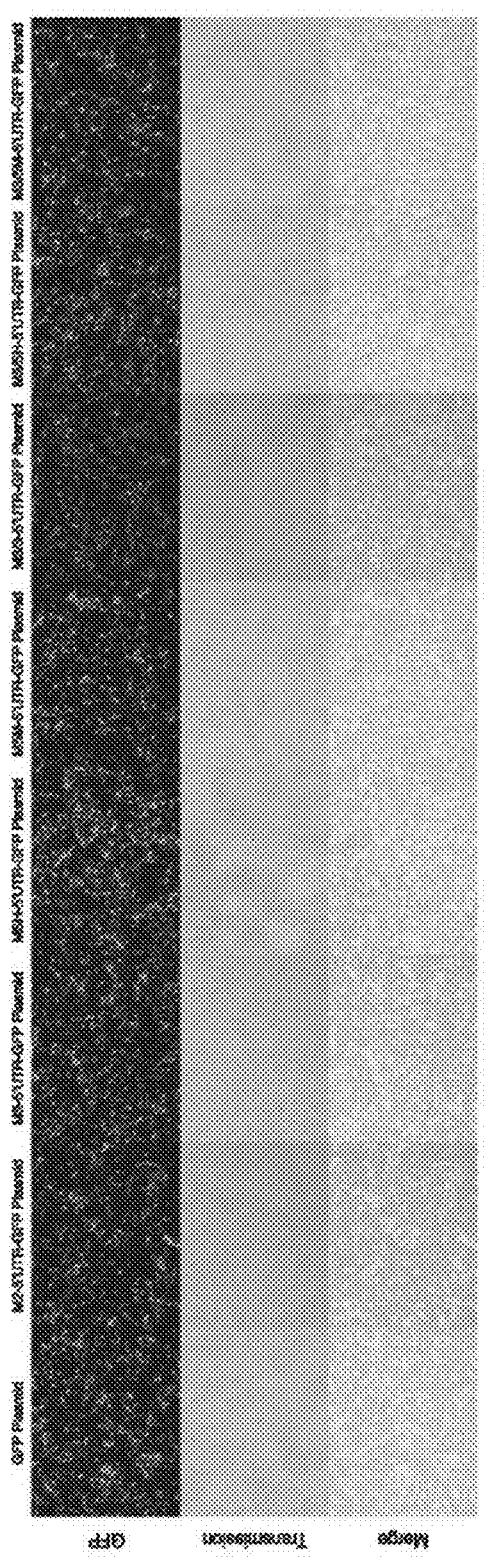
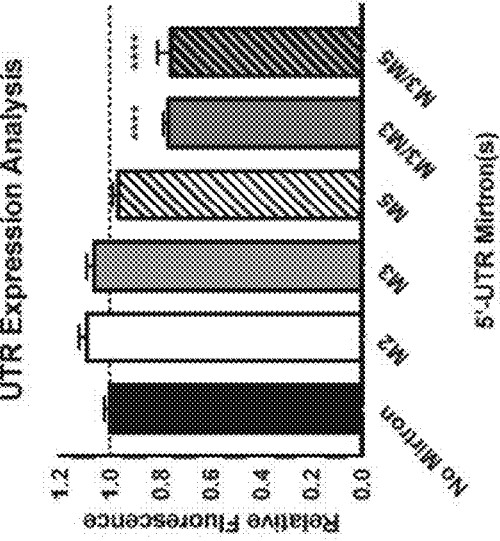
FIG. 27

AAV-M3/5H.WPRE

ITR  RHOp  EX/IN  M3  M5H  RHO^MCS  WPRE  PA  ITR

FIG. 33

FIG. 35
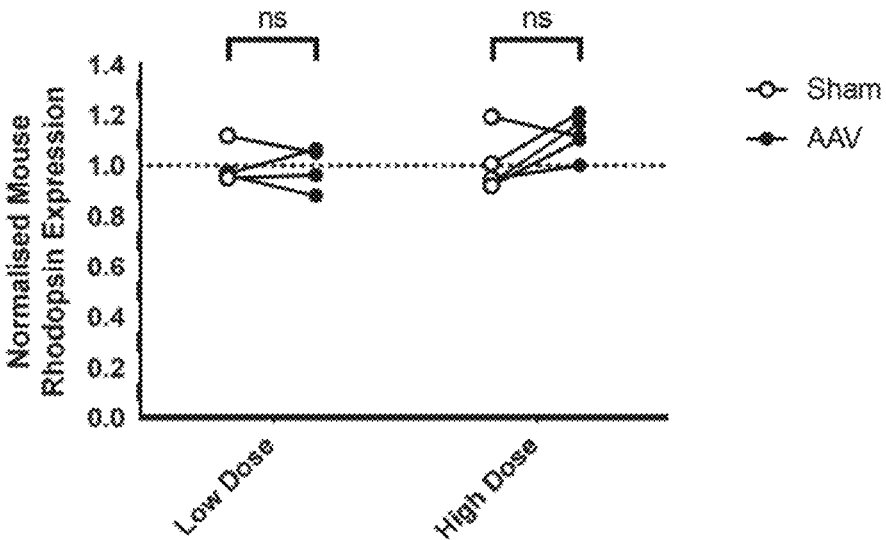
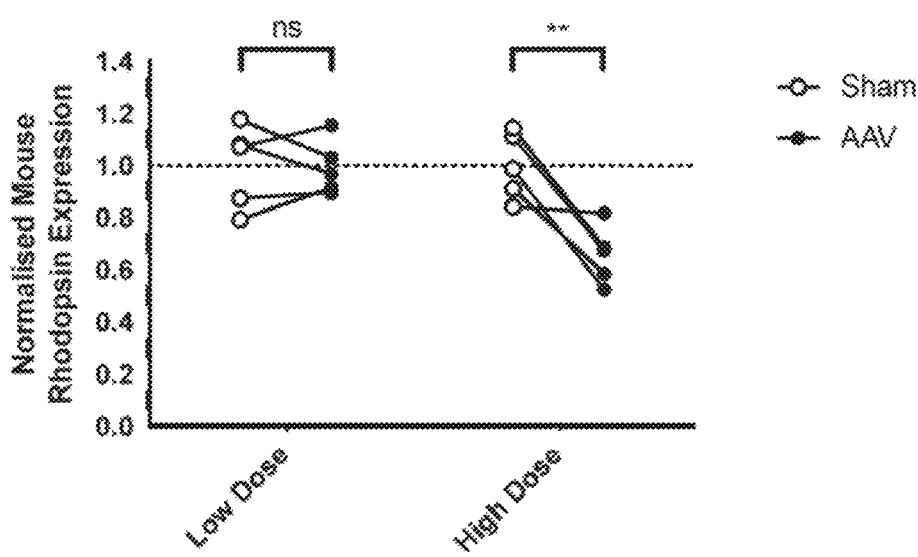

FIG. 47

GENE THERAPY FOR RETINAL DISEASE

CROSS-REFERENCE TO RELATED APPLICATIONS

This application is the National Stage of International Application No. PCT/GB2019/053036, filed Oct. 25, 2019, which claims priority to GB 1817469.8, filed Oct. 26, 2018, which are entirely incorporated herein by reference.

Sequence Listing

This application contains a sequence listing filed in electronic form as an ASCII.txt file entitled "ST.25 sequence listing-N413815US.TXT", having a size of 58,733 bytes, created May 21, 2025. The content of the sequence listing is incorporated herein in its entirety.

FIELD

The disclosure relates to methods of gene therapy to treat retinal diseases using mirtrons and to vectors for use therein.

BACKGROUND

A mirtron is a microRNAs derived from an intron that is released following splicing and processed within the cell. It has been proposed to use artificial mirtrons as part of a gene therapy vector to treat dominant disease. The mirtron could be accompanied in the vector by a codon-modified version of the target gene, which is engineered to be resistant to co-delivered mirtrons, as part of a 'block and replace' treatment paradigm. However, co-delivery of mirtrons with a transgene in a way that preserves both efficient splicing of the mirtron and adequate transgene expression is challenging (Curtis et al. Nucleic Acids Research 45(13): 7870-7885 (2017)) and has not been achieved to date.

Dominant retinitis pigmentosa (RP) is a blinding disease that is commonly caused by mutations in the rhodopsin gene expressed in the retina. There is at present no approved treatment. However, methods are being developed to deliver gene therapy to the cells of the retina to treat diseases such as RP using adeno-associated virus (AAV) (Fischer M D et al (2017). Molecular Therapy. 25 (8): 1854-1865).

SUMMARY

The inventors are the first to achieve knock down of a target gene in the retina using a mirtron. They have demonstrated the first use of mirtrons to treat a any disease in vivo. The inventors have succeeded in achieving co-delivery of an artificial mirtron with a 'replacement' transcript in which expression of the transcript is not substantially adversely affected by the presence of the mirtron. The inventors have demonstrated that disrupted expression of the transgene can be avoided by locating the mirtron in the 5'UTR of the transgene. Efficient splicing from the 5'UTR can be achieved by including exonic splice enhancer motifs (ESEs) in the regions of the 5'UTR flanking the mirtron. The inventors have demonstrated successful use of mirtrons in vivo and to treat a disease model, the use of adeno-associated virus (AAV) to successfully deliver mirtrons, and increased gene knock-down by co-delivery of multiple mirtrons from a single transcript.

Accordingly, in a first aspect the invention provides a method of treating a retinal disease in a subject in need thereof, the method comprising administering to the subject a vector that comprises a mirtron for knocking down expression of a target gene expressed in the retina.

In a further aspect the invention provides a gene therapy vector comprising a mirtron for rhodopsin knock-down.

In some cases the vector further comprises a transgene for expression in the retina.

In some cases the transgene is a variant of the target gene or a variant rhodopsin gene and the variant gene is resistant to knock-down by the mirtron.

In some cases the mirtron is embedded in the transgene or in the variant rhodopsin gene.

In some cases the mirtron is located in the 5'UTR of the transgene or in the variant rhodopsin gene.

In some cases the 5'UTR further comprises one or more exonic splice enhancer motifs.

In some cases the vector comprises two or more mirtrons for knocking down expression of one or more target genes expressed in the retina.

In a further aspect the disclosure provides a pharmaceutical composition comprising the gene therapy vector as described above.

The disclosure will now be described in more detail, by way of example and not limitation, and by reference to the accompanying drawings. Many equivalent modifications and variations will be apparent, to those skilled in the art when given this disclosure. Accordingly, the exemplary embodiments of the disclosure set forth are considered to be illustrative and not limiting. Various changes to the described embodiments may be made without departing from the scope of the disclosure. All documents cited herein, whether supra or infra, are expressly incorporated by reference in their entirety.

The present disclosure includes the combination of the aspects and preferred features described except where such a combination is clearly impermissible or is stated to be expressly avoided. As used in this specification and the appended claims, the singular forms "a", "an", and "the" include plural referents unless the content clearly dictates otherwise. Thus, for example, reference to "a vector" includes two or more such entities.

Section headings are used herein for convenience only and are not to be construed as limiting in any way.

(A) Images of cells immunostained from rhodopsin. Note GFP labelled cells (green) stain for rhodopsin (red) in transduced but not untransduced cells. Age-matched dissociated wild type cells are shown as a positive control in the left-hand panels. (B) Human rhodopsin mRNA levels in transduced dissociated cells measured by qPCR revealed a four-fold increase in the number of transcripts for scRHO compared with the other three vectors (**p<0.01, 1-way ANOVA).

Figures 3A, 3B:
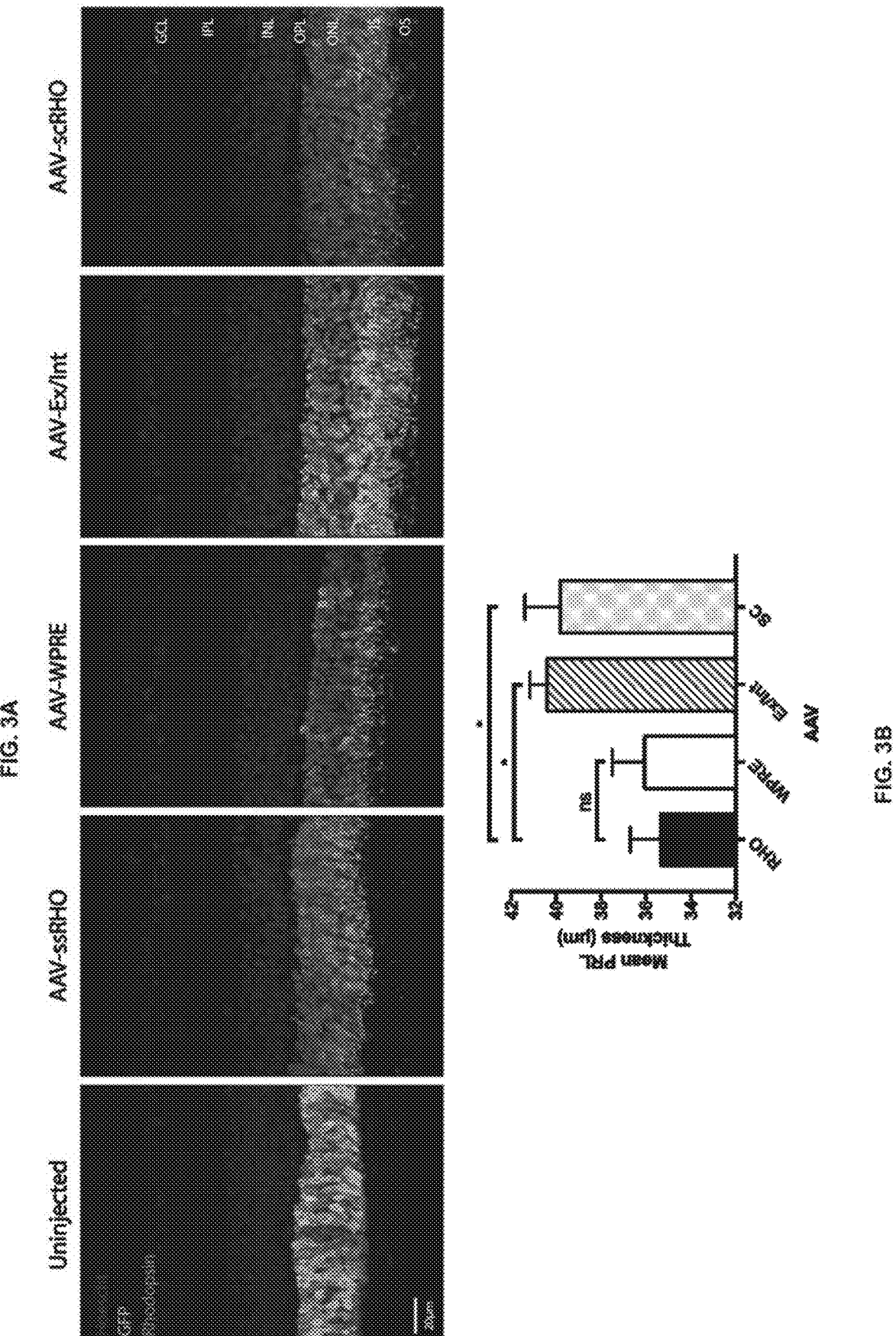

FIGS. 3A-3B In vivo comparison of RHO-expressing AAVs. (A) Nrl.GFP/Rho$^{-/-}$ mice received subretinal injections of the four AAV-RHO viruses. Immunostaining for rhodopsin in retinal sections suggested greatest expression with Ex/Int and SC vectors. All promoters conferred rod-specific expression. GCL ganglion cell layer; IPL inner plexiform layer; INL inner nuclear layer; OPL outer plexiform layer; ONL outer nuclear layer; IS inner segments; OS outer segments. (B) SD-OCT was performed on live mice 4 weeks post-injection. Photoreceptor layer (PRL) thickness was greatest for Ex/Int and SC-injected mice supporting the immunohistochemistry findings. *p<0.05, one-way ANOVA Holm-Sidak multiple comparison test.

Figure 4A:
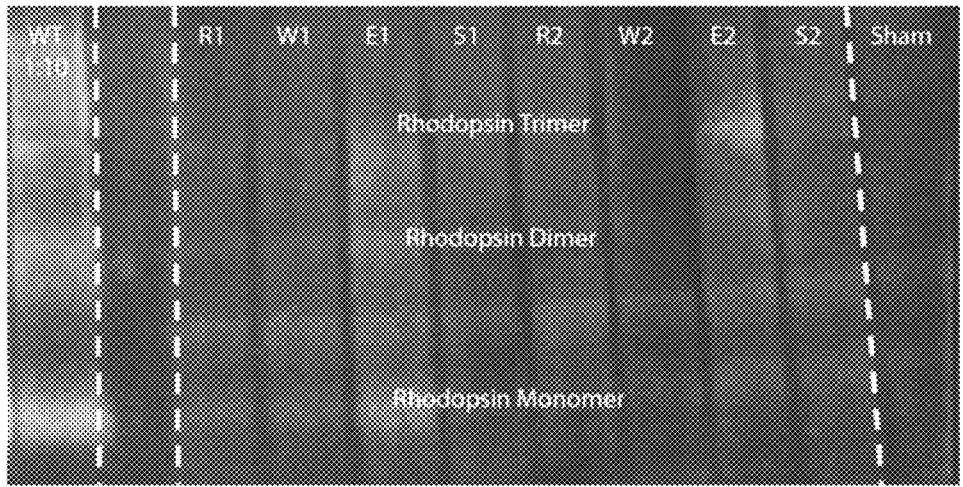
Figure 4B:
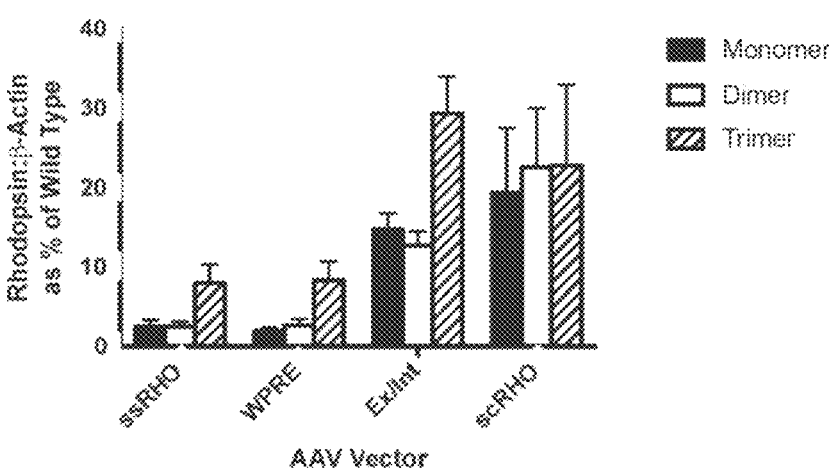

FIGS. 4A-4B Western blot of protein lysates derived from the neural retina of AAV-RHO injected Nrl.GFP/Rho$^{-/-}$ mice. (A) Example of a western blot of transduced retinal lysates stained for rhodopsin. Note that transgenic rhodopsin results in a pattern of bands similar to that derived from an untransduced wild-type mouse, albeit at a much lower level of expression. (B) Band densitometry showed that the greatest level of protein expression was achieved with Ex/Int and SC vectors. Two-way ANOVA p<0.001 for effect of vector. Tukey's multiple comparison test: scRHO vs ssRHO or WPRE, p<0.01; Ex/Int vs ssRHO or WPRE, p<0.05; ssRHO vs WPRE, ns; Ex/Int vs SC, ns.

Figure 5A:
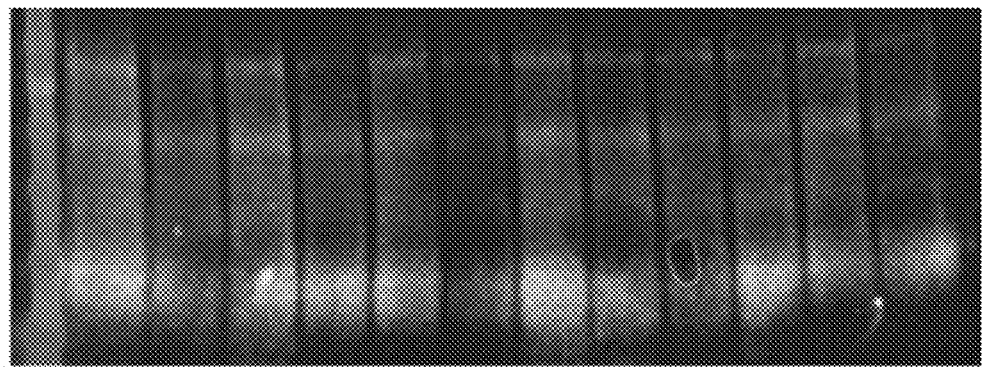
Figure 5B:
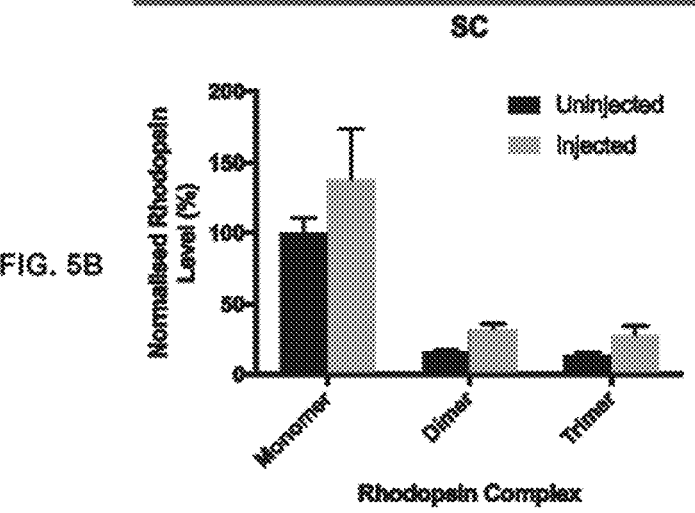
Figure 5C:
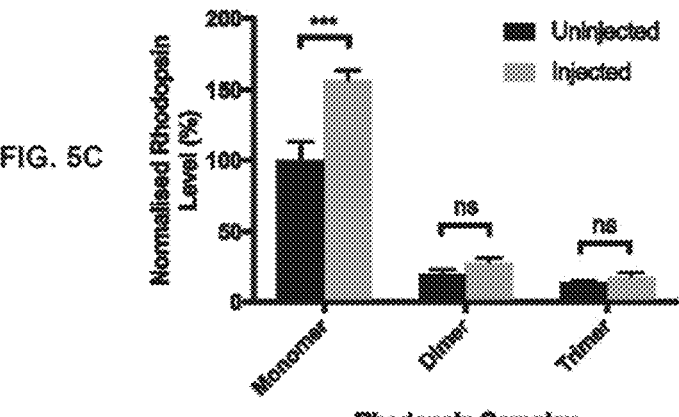

FIGS. 5A-5C Western blots showing overexpression of rhodopsin following subretinal injection of Ex/Int and scRHO vectors. (A) Example western blot showing increased rhodopsin band density (green) in injected right eyes (OD) compared with uninjected left eyes (OS). (B, C) Band densitometry normalised to beta actin. Two-way ANOVA p=0.21 for effect of SC, p=0.023 for effect of Ex/Int.

Figure 6:
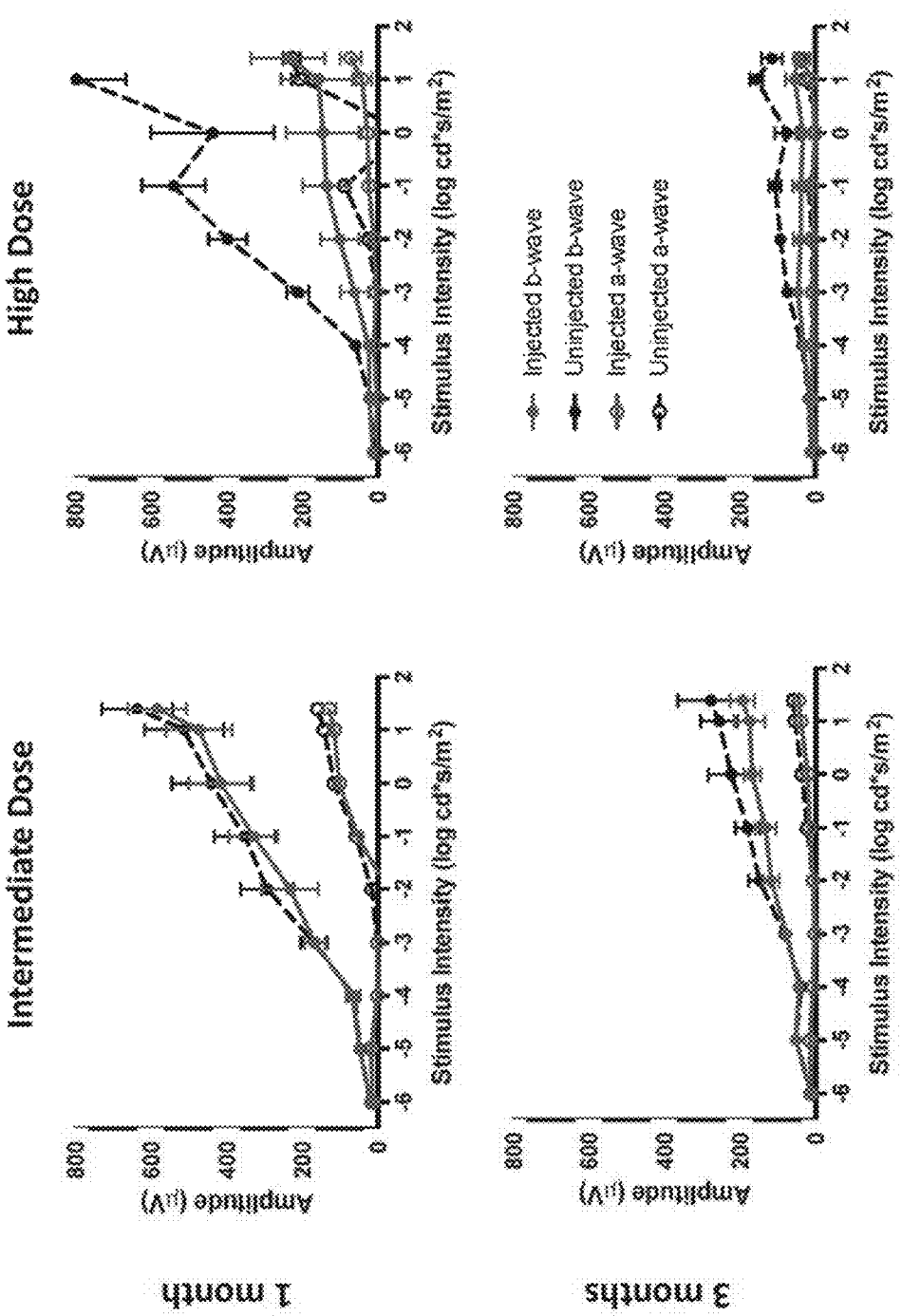

FIG. 6 Intensity response curves derived from dark-adapted electroretinography (ERG) recordings from P23H mice injected unilaterally with AAV-Ex/Int. No difference in responses between eyes was detected in the intermediate dose group at either one or three months post-injection, and no slowing of the degeneration was observed. The high dose of vector appeared toxic.

Figure 7:
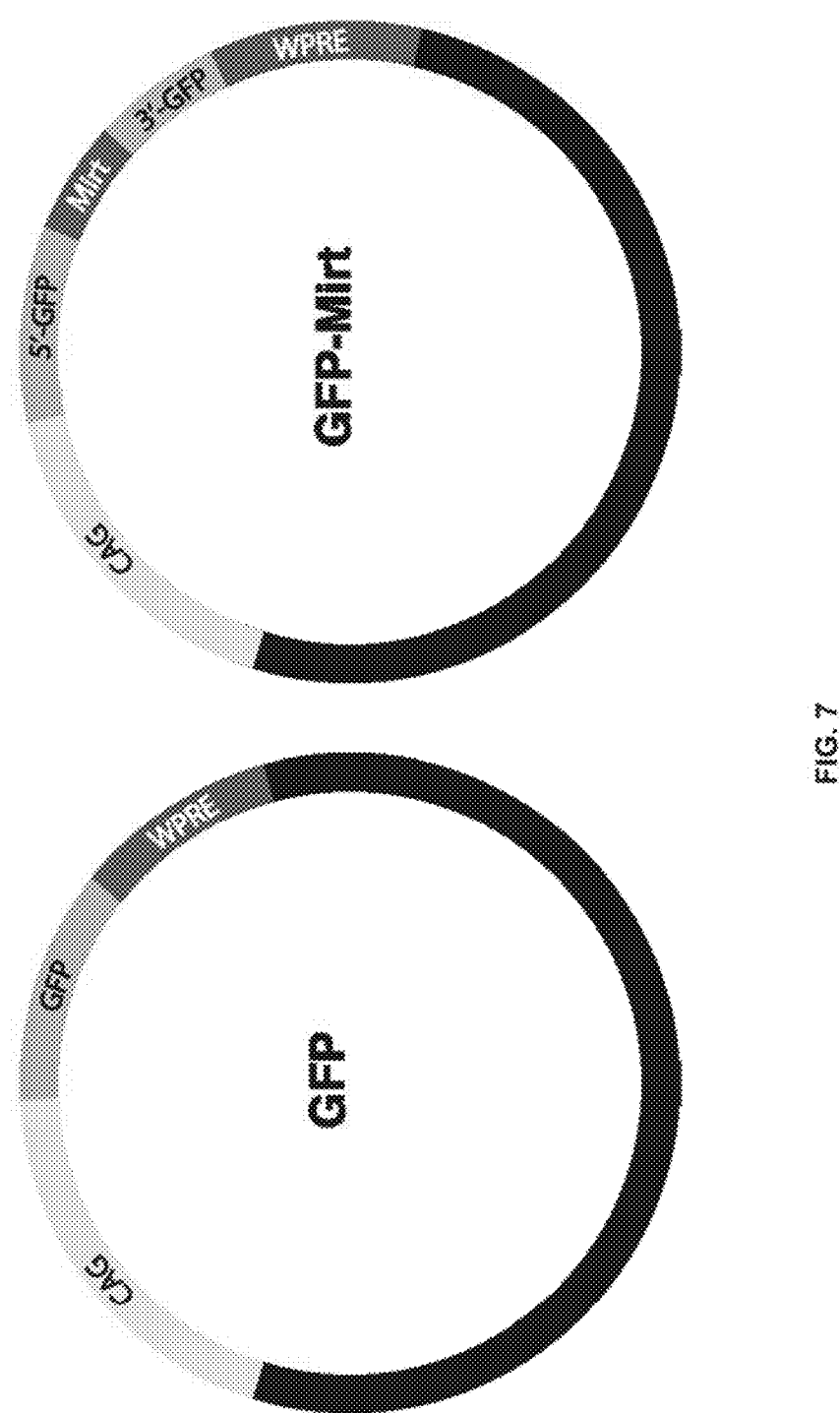

FIG. 7 GFP-Mirtron plasmid maps. The 76 bp mirtron insert at the BstB1 restriction site disrupts the GFP coding sequence and is predicted to cause a frame shift in GFP if not correctly and completely spliced.

Figure 8:
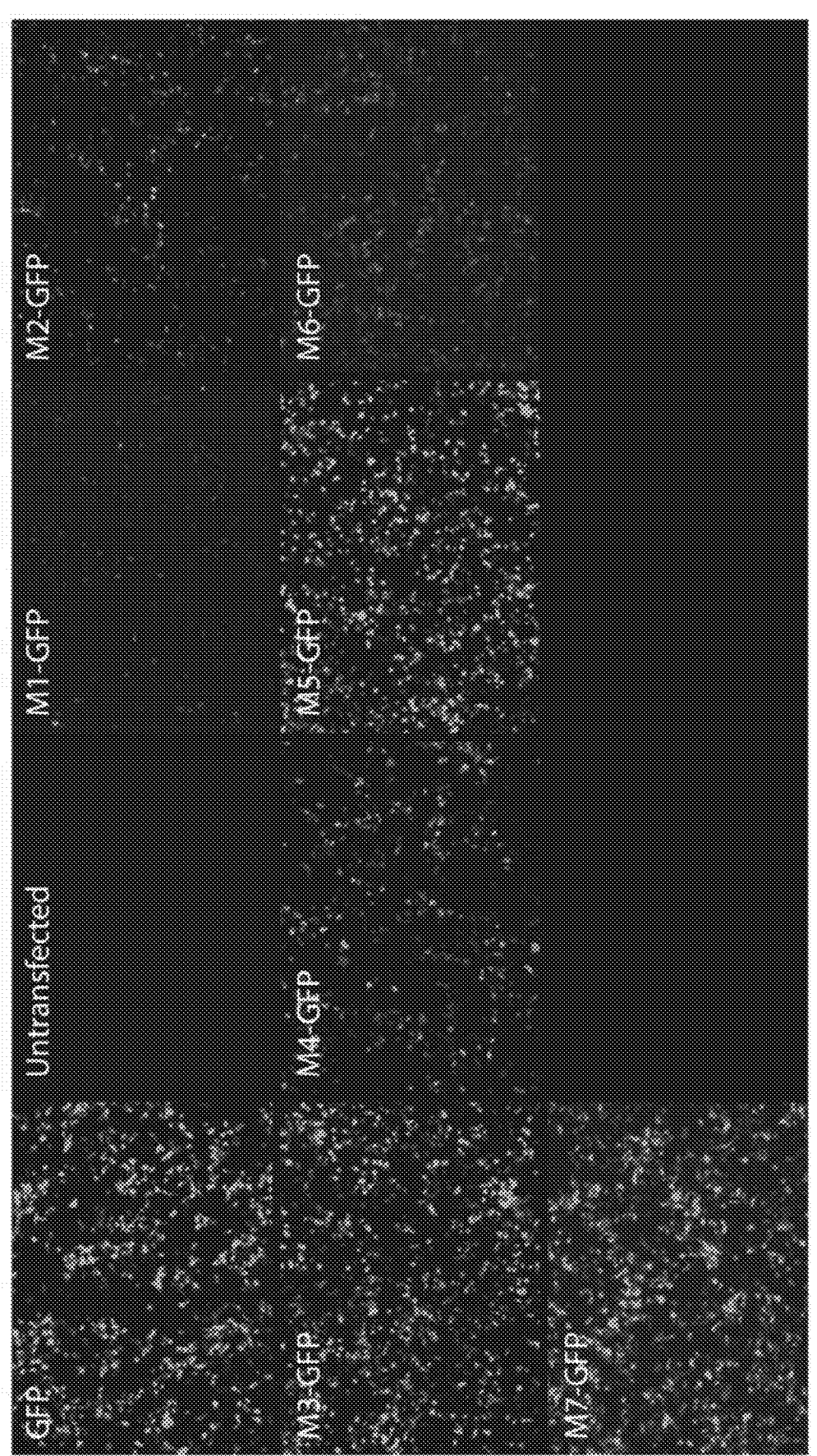

FIG. 8 Transfection of HEK293 cells with GFP-Mirtron plasmids. Differing levels of green fluorescence indicate variation of splicing efficiency between mirtron designs.

Figures 9A, 9B:
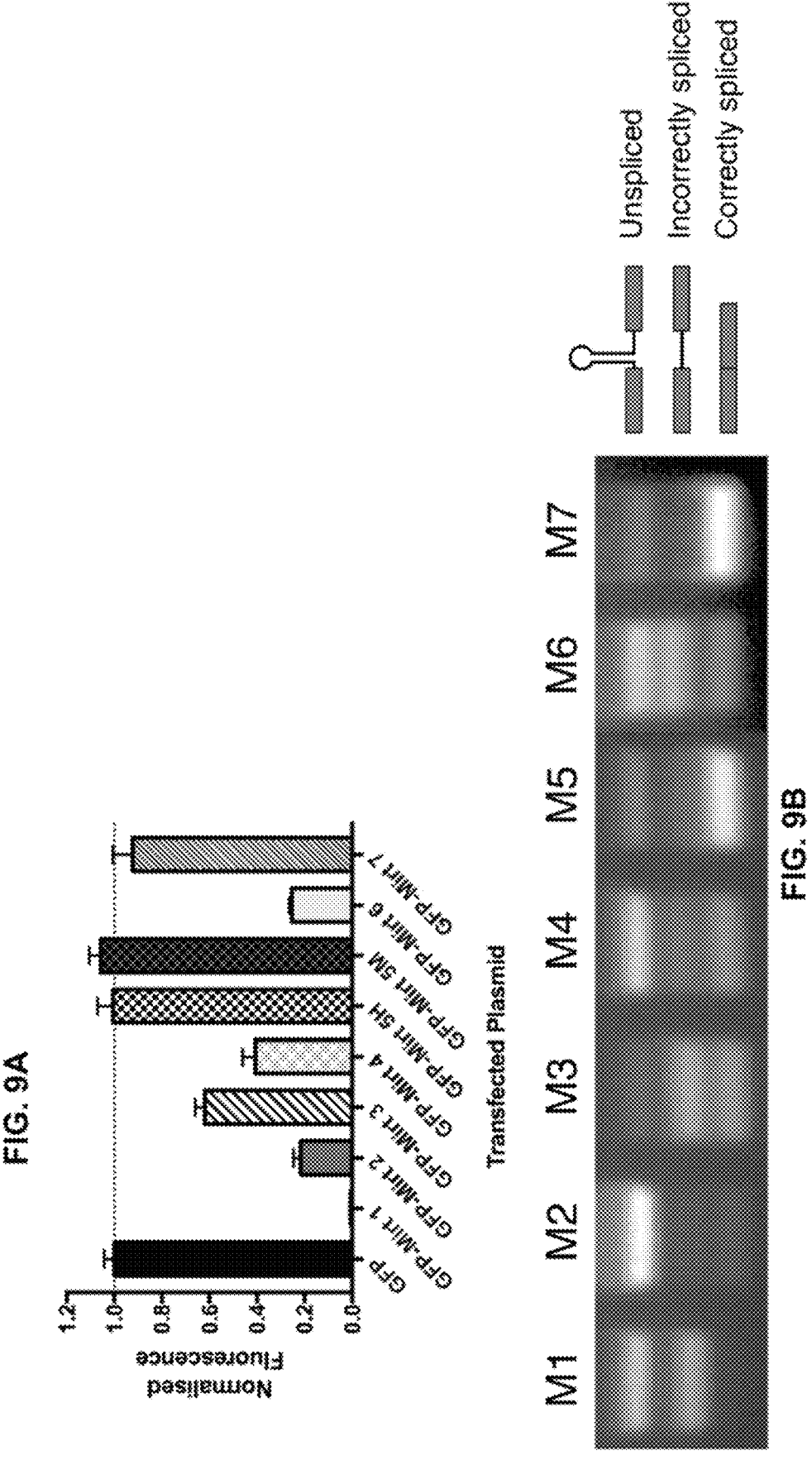

FIGS. 9A-9B Splicing efficiency of mirtrons 1-7. (A) Normalized fluorescence assay based on signal from the lysates of transfected cells shown in FIG. 8. (B) PCR was performed from GFP-mirtron transfected HEK293 cDNA with mirtron-spanning primers. Relative densitometry readings from PCR amplicon bands shown in (B) (data not shown).

Figures 10A, 10B:
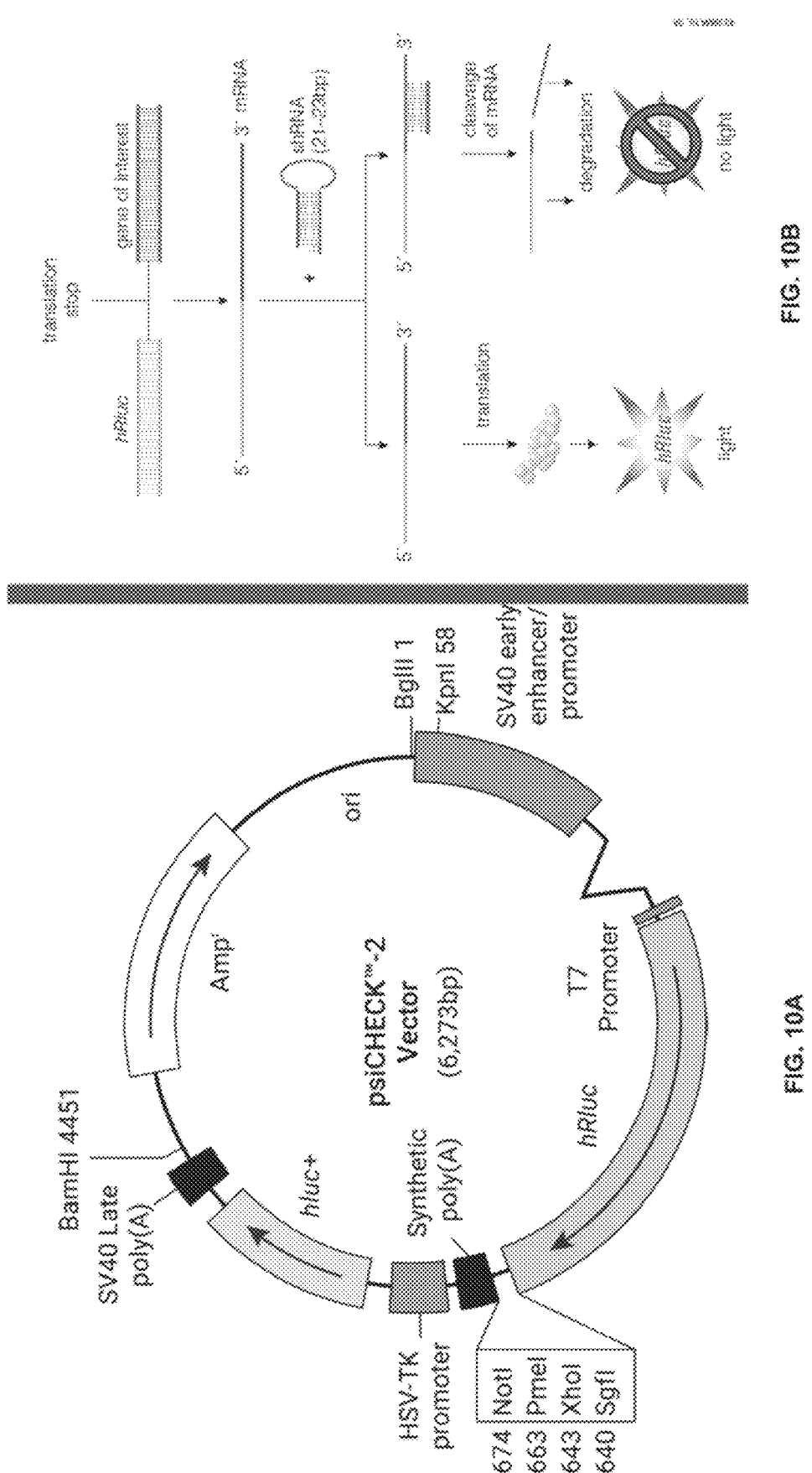

FIG. 10 The PsiCHECK2 plasmid and Dual Glo Luciferase assay (Promega).

FIGS. 11A-11B Rhodopsin knockdown efficiency of mirtrons 1-7 measured with the Dual Glo Luciferase assay against human and mouse coding sequences.****p<0.0001, one-way ANOVA Dunnett's multiple comparison test.

Figure 12A:
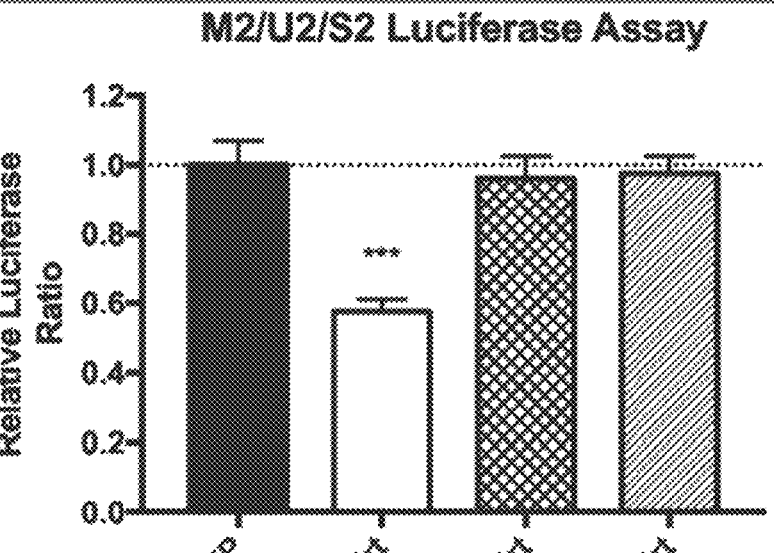
Figure 12B:
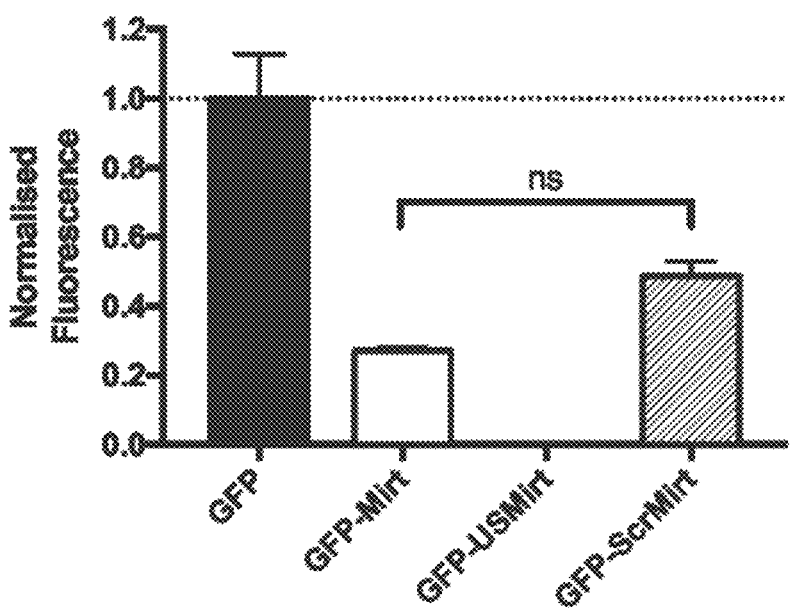

FIGS. 12A-12B Both splicing and a specific target sequence are required to achieve mirtron-mediated rhodopsin knockdown.

Figure 13:
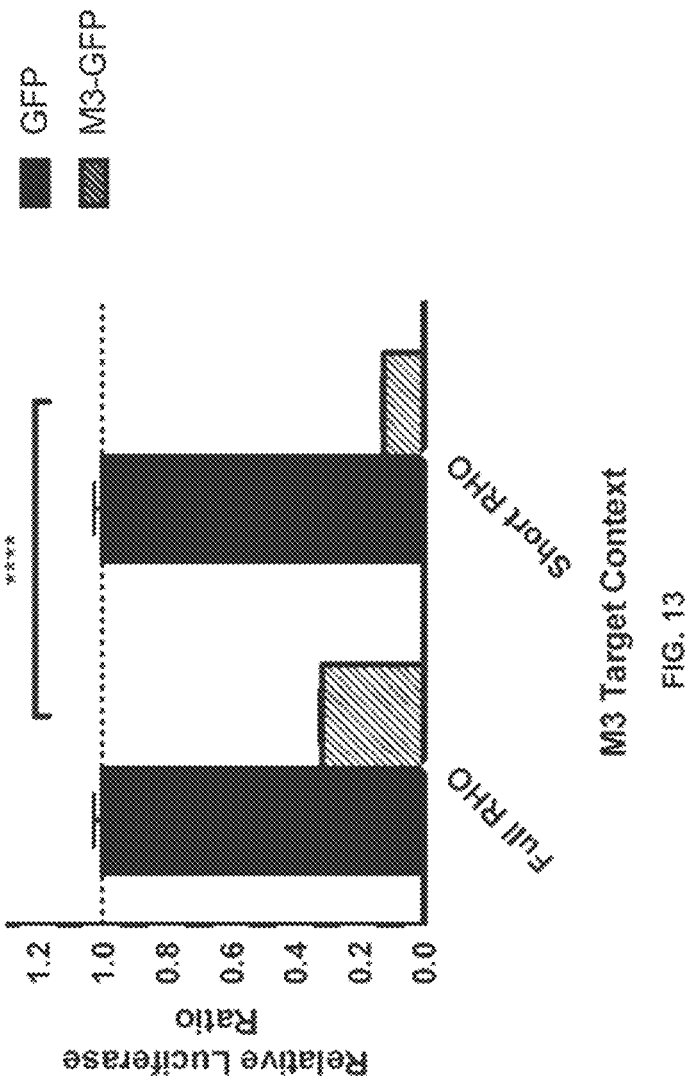

FIG. 13 mRNA target context influences potency of mirtrons. 'Full RHO' corresponds to the PsiCHECK2 vector into which the full length human rhodopsin coding sequence has been cloned. The 'Short RHO' PsiCHECK2 plasmid contains just the region of the human rhodopsin sequence corresponding to the 21 bp M3 target sequence with 25bp of 5' and 3' flanking DNA. ****p<0.0001, 2-way ANOVA, Sidak's multiple comparison test.

Figure 14:
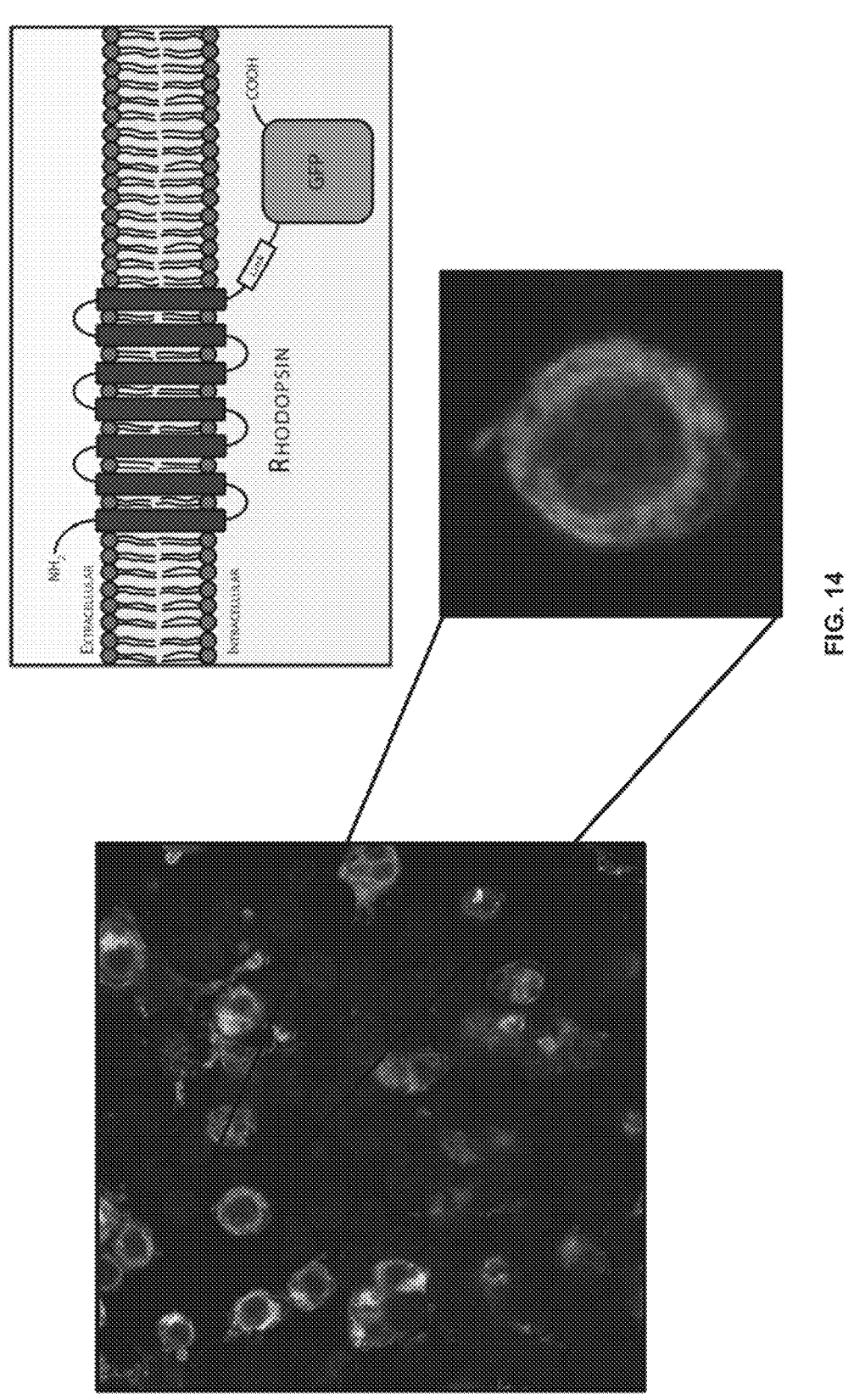

FIG. 14 RHO-GFP traffics to the plasma membrane.

HEK293 cells were transfected with the CAG.RHO-GFP.WPRE plasmid and stained for rhodopsin with the N-terminus directed antibody 4D2.

FIG. 15 RHO-Luc traffics to the plasma membrane. HEK293 cells were transfected with the PsiCHECK2-RHO plasmid (designed for the conventional dual luciferase assay; top row), or the RHO-Luc. PsiCHECK2 plasmid (designed for the dual luciferase fusion assay; bottom row). Schematics of the corresponding proteins are shown to the left.

Figure 16:
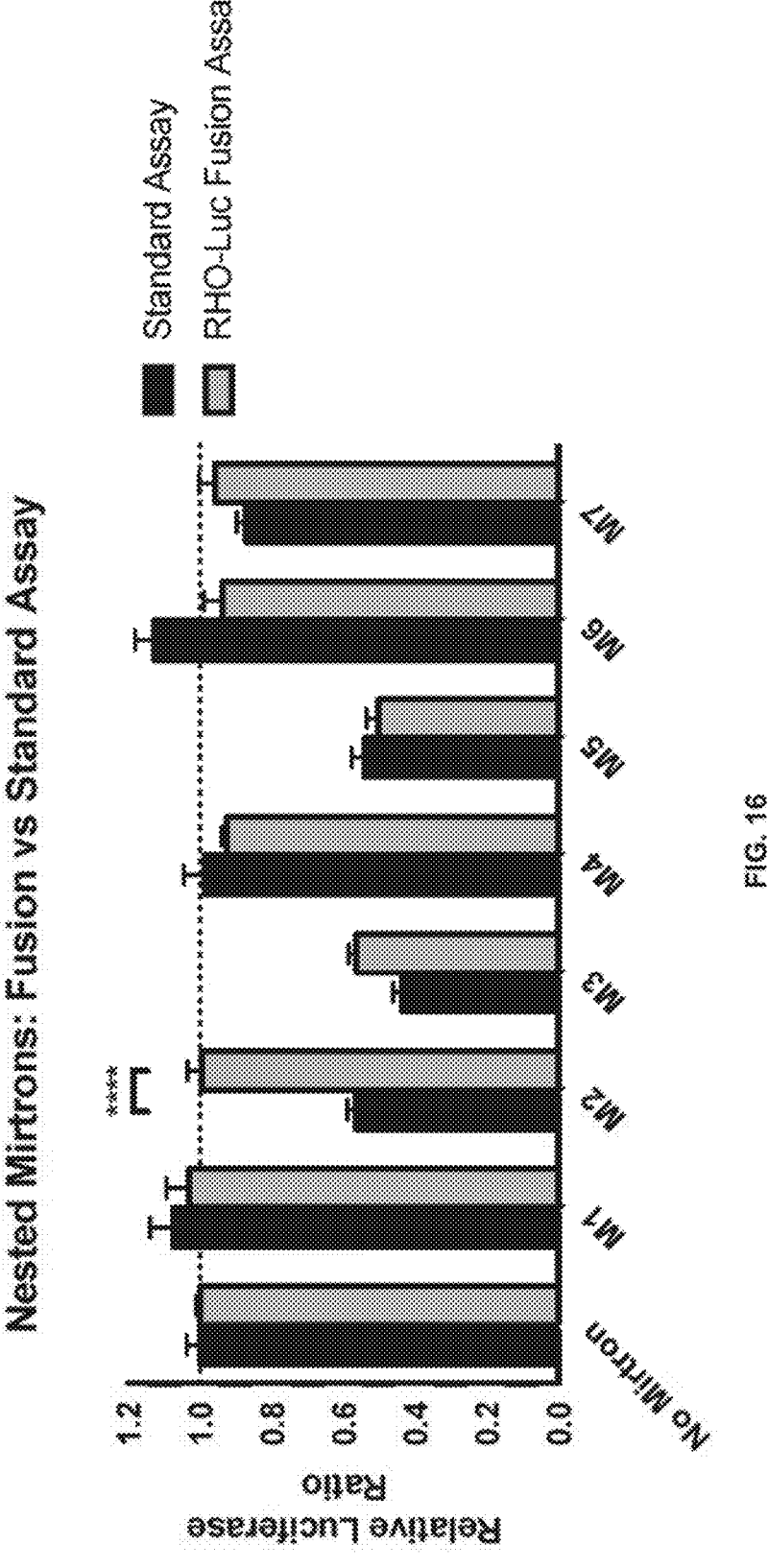

FIG. 16 Mirtron-mediated rhodopsin knock-down using the Dual Glo Luciferase assay in conjunction with Psi-CHECK2-RHO ('standard assay') and RHO-Luc.Psi-CHECK2 ('Fusion Assay'). Note that knock-down effect is similar when measured by the two assays in all cases except for that of Mirtron 2.

Figure 17:
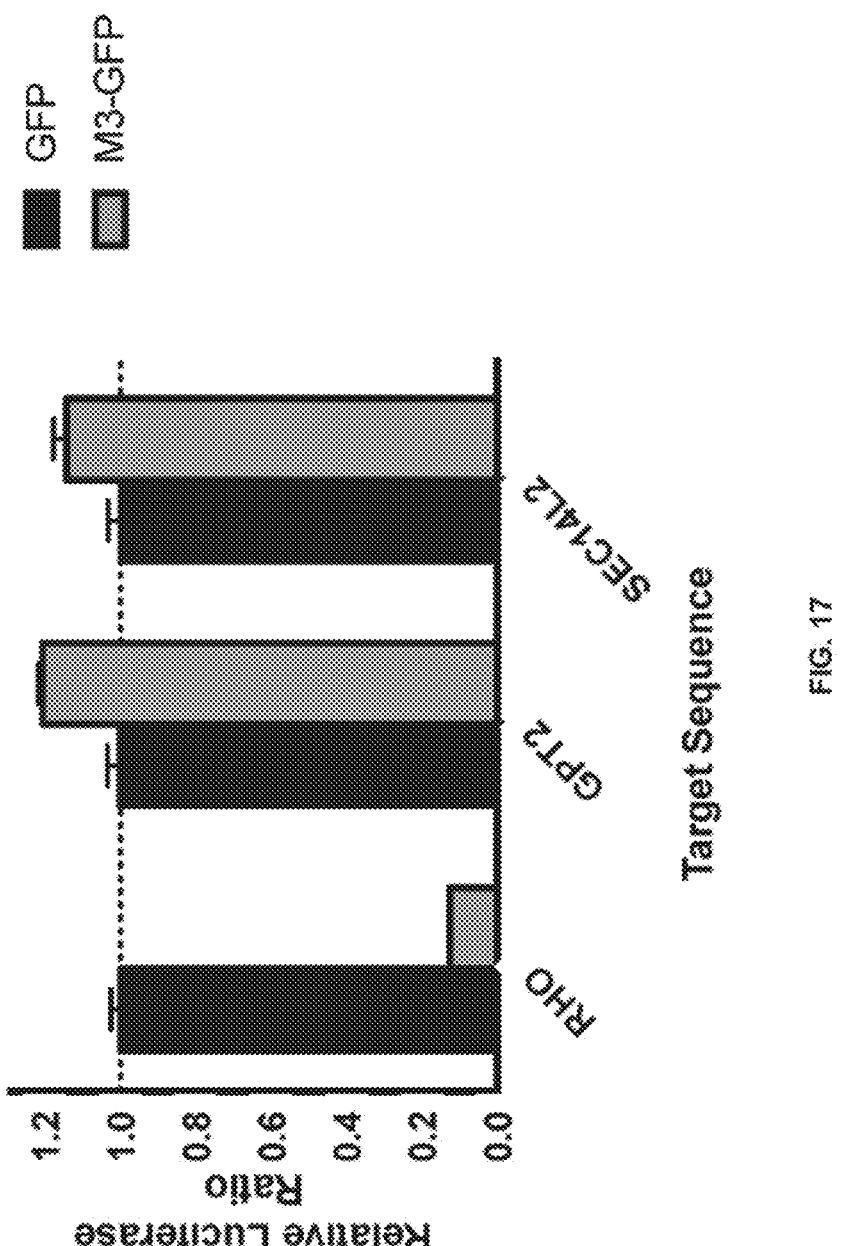
Figures 18A, 18B:
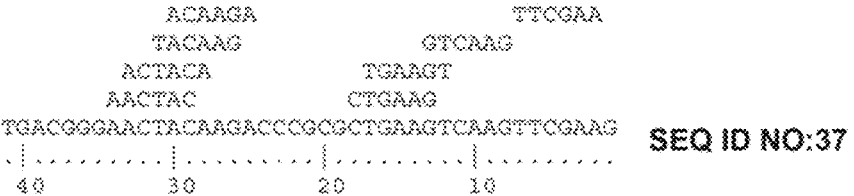

FIG. 17 Predicted 'off targets' are not subject to mirtron-mediated knock-down FIGS. 18A-18B ESE-rich mirtron-flanking eGFP CDS sequences and ESEs. A: 5' sequence. B: 3' sequence. Distances upstream from splice donor motif or downstream of splice acceptor motif of mirtron are indicated.

Figure 19:
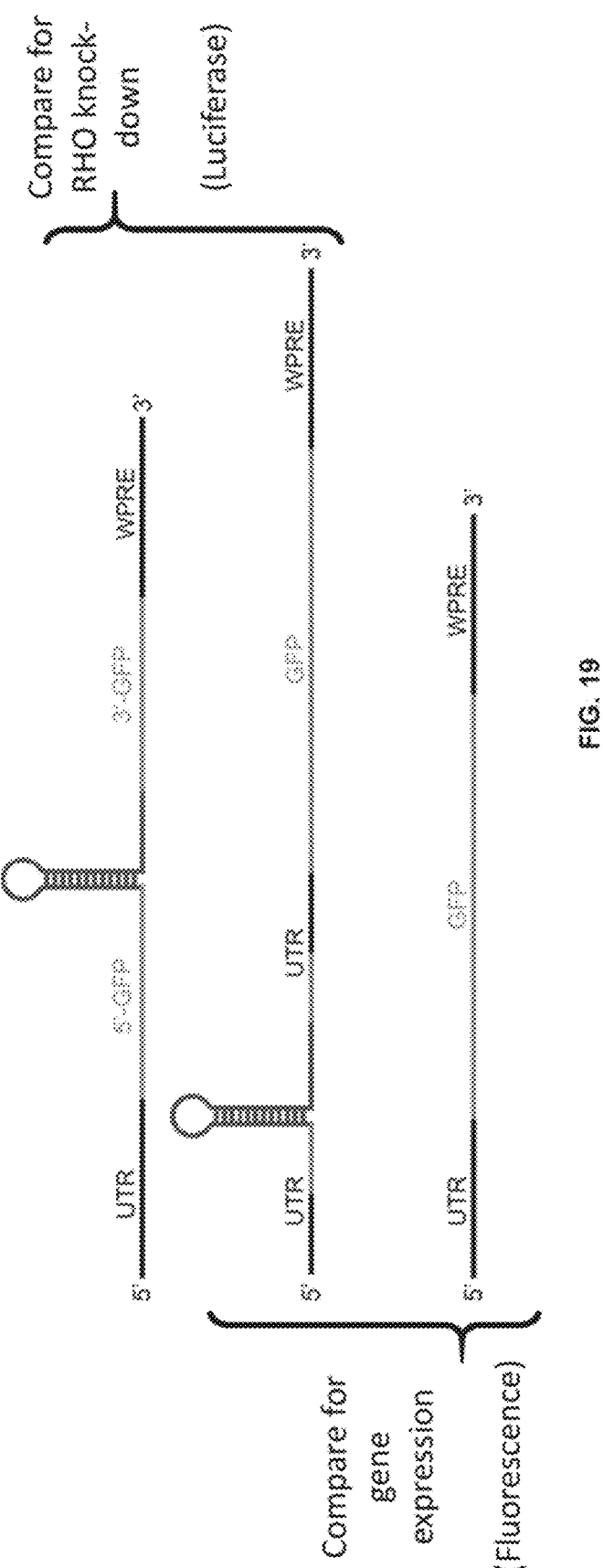
Figure 20A:
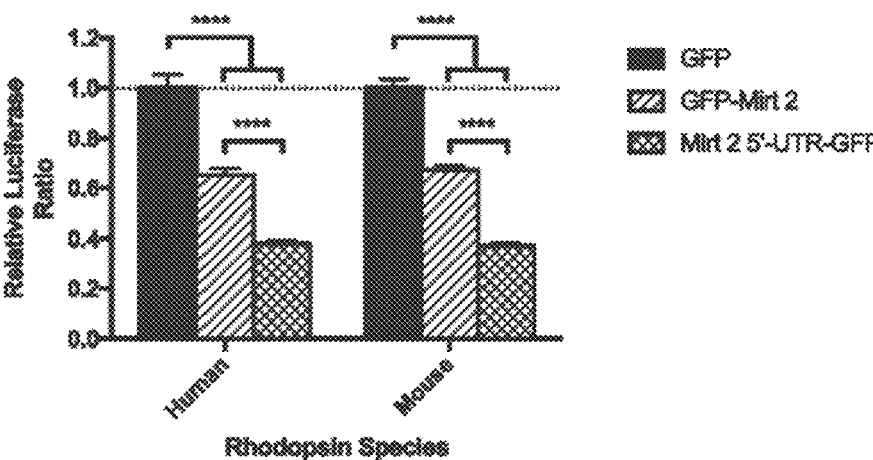
Figure 20B:
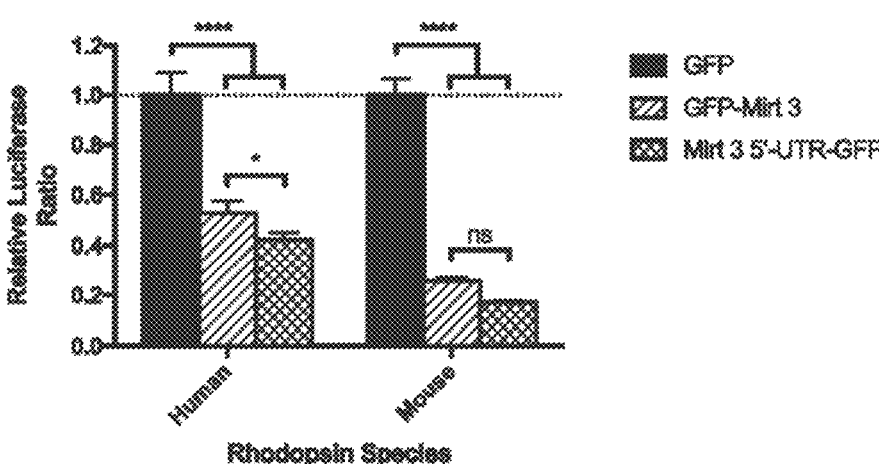
Figure 20C:
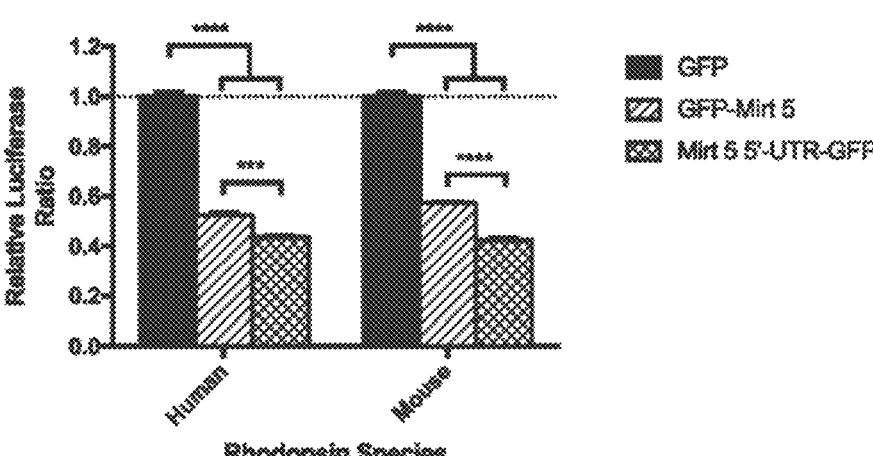

FIG. 19 Experimental design to test the efficacy of 5'-UTR mirtrons and their effect on downstream gene expression FIGS. 20A-20C Mirtrons are more effective when located in the 5'-UTR rather than the CDS of GFP. Dual luciferase assays were performed comparing M2 with M2-UTR (A), M3 with M3-UTR (B), and M5 with M5-UTR (C). n=6 in all cases. ns, not significant; *p<0.05; *p<0.001; **p<0.0001; Two-way ANOVA with correction for multiple comparisons.

Figures 21A, 21B:
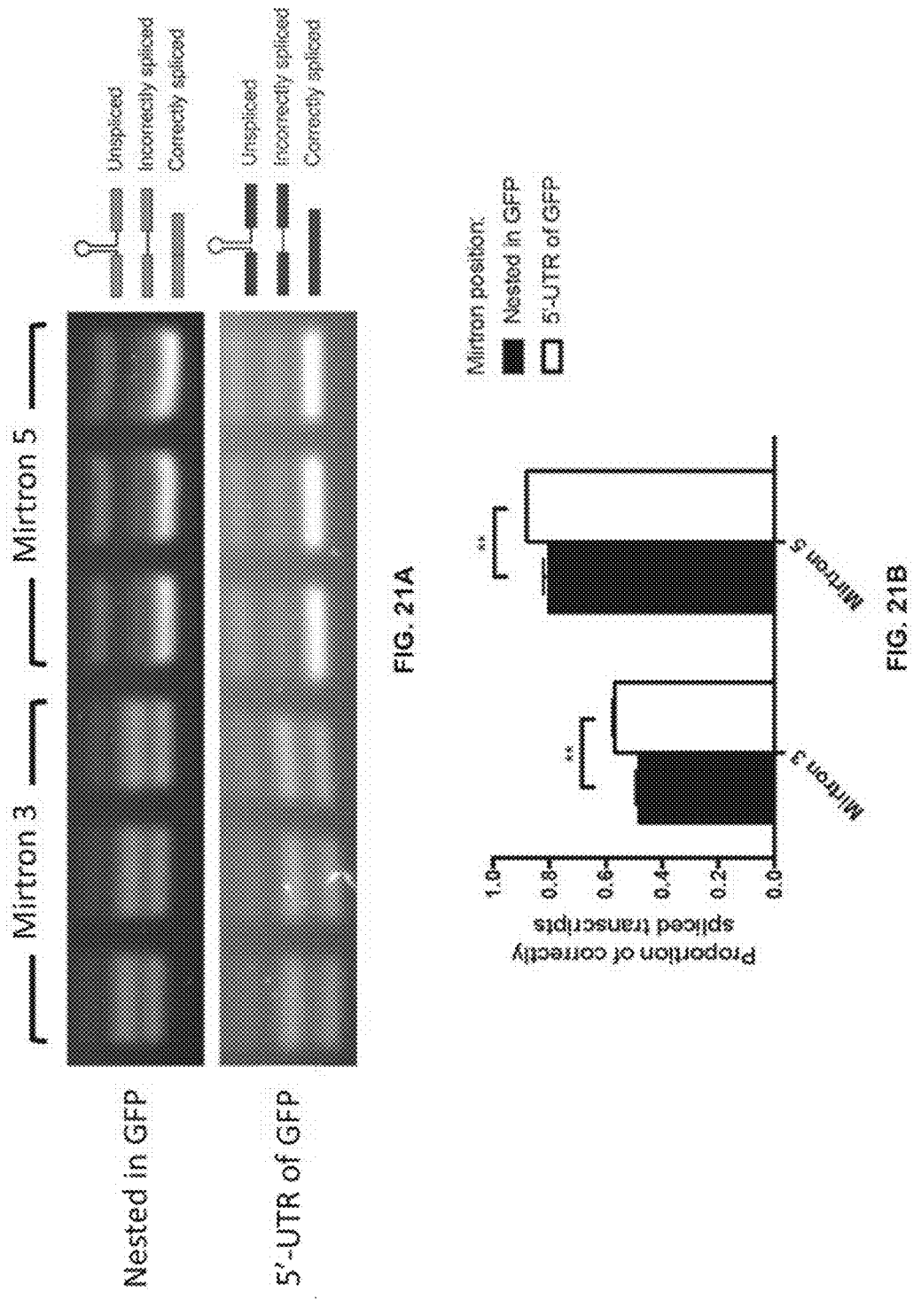

FIGS. 21A-21B Enhanced splicing may explain improved efficacy of 5'-UTR mirtrons. (A) PCR splice product analysis for nested and 5'-UTR mirtrons. (B) band densitometry. n=3, **p<0.01, Two-way ANOVA Sidak's multiple comparison test.

Figure 22A:
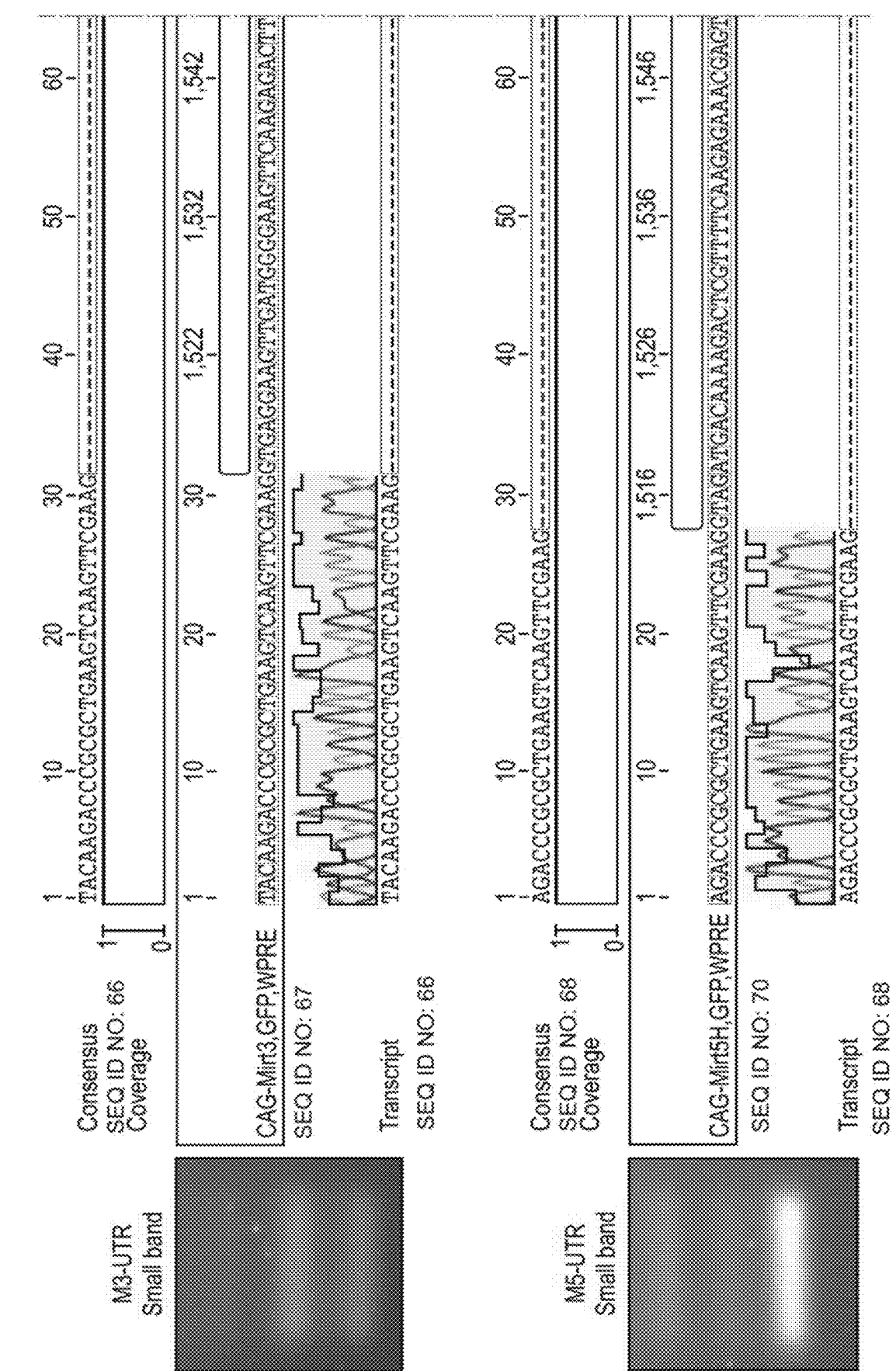
Figure 22B:
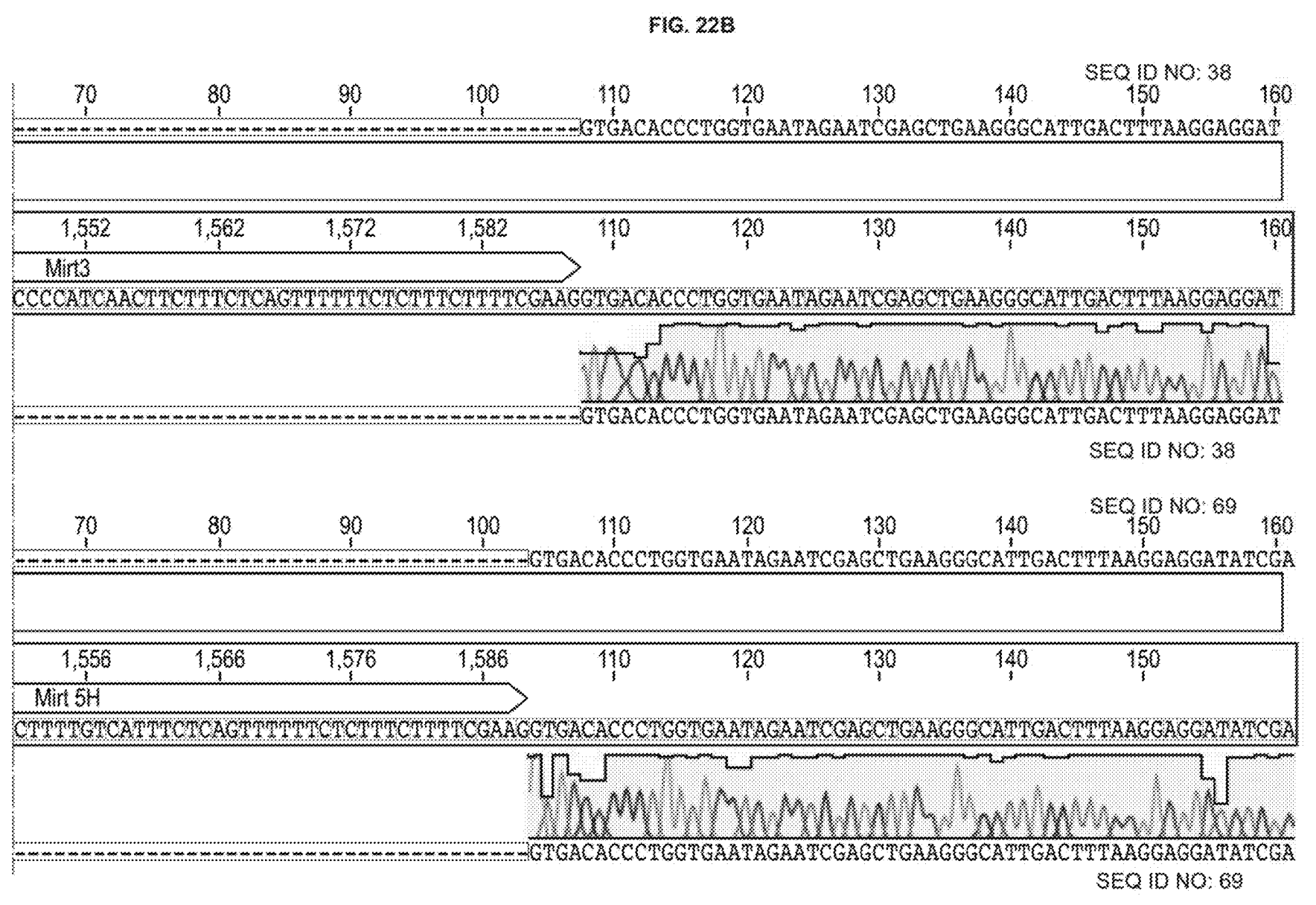

FIGS. 22A-22B Correct splicing of mirtrons 3 and 5 from the 5'-UTR is confirmed by Sanger sequencing of amplified cDNA from transfected HEK293 cells.

FIGS. 23A-23D Mirtrons in tandem result in increased rhodopsin knock-down. (A, B) Two copies of M3 in series within the 5'-UTR is more effective than one. (C, D) One copy of M3 and one copy of M5 in series is more effective than either mirtron alone in the 5'-UTR. Data shown is for the version of M5 (M5H and M5M) directed against its corresponding species. ns=not significant; *p<0.05; p<0.01; **p<0.0001; 2-way ANOVA Sidak's multiple comparison test.

Figure 24:
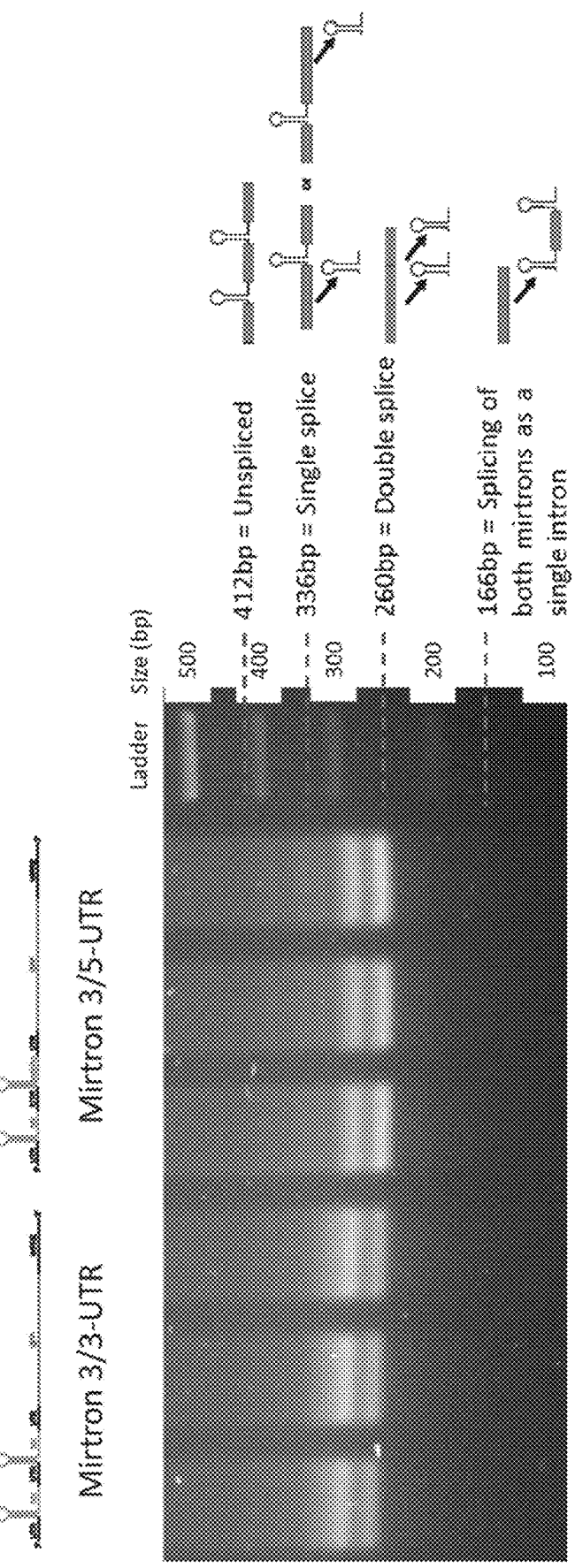

FIG. 24 Splice analysis of tandem 5'-UTR mirtrons. Note that no bands corresponding to those predicted for unspliced (412 bp), single spliced (336 bp) or exon-skipped (166 bp) transcripts were detected.

Figure 25A:
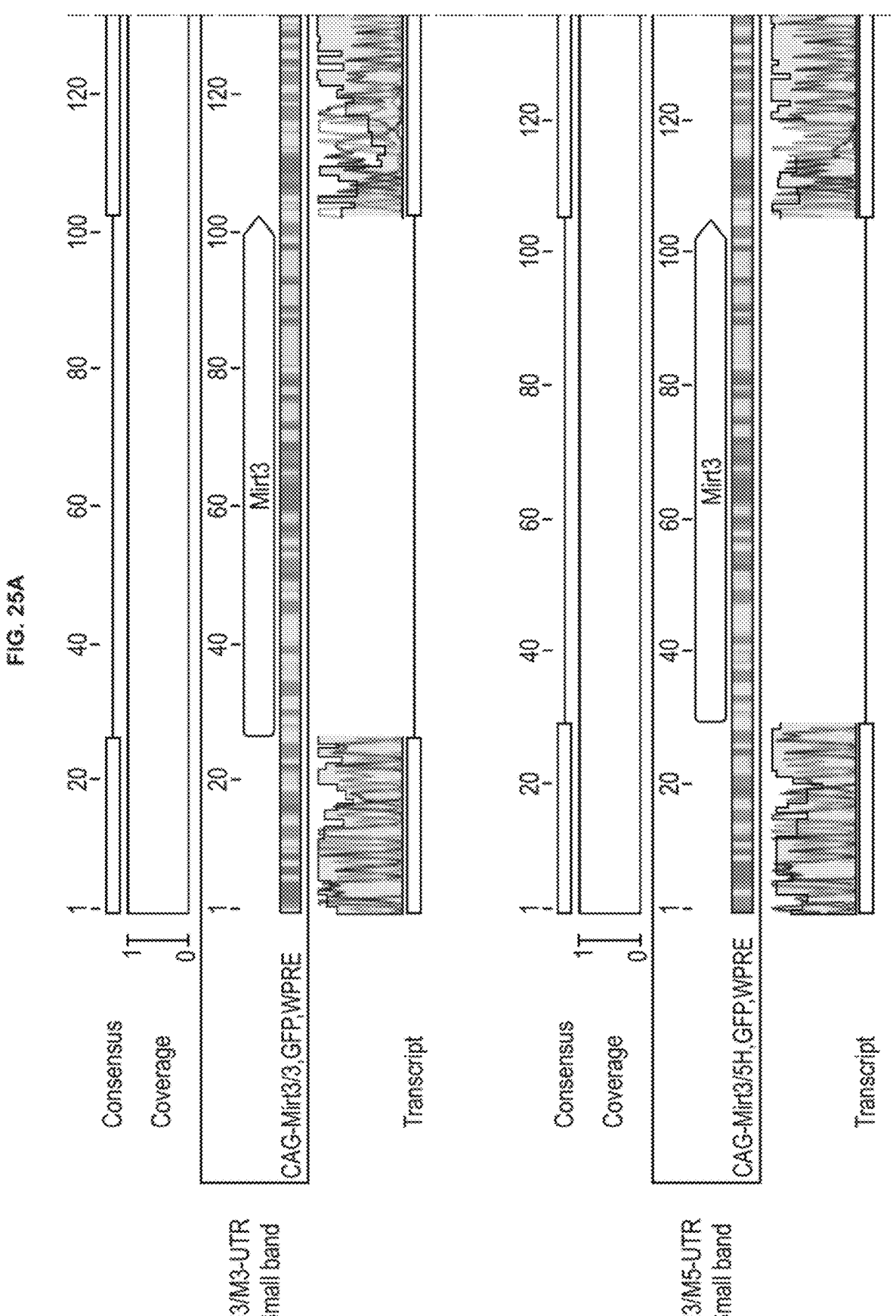
Figure 25B:
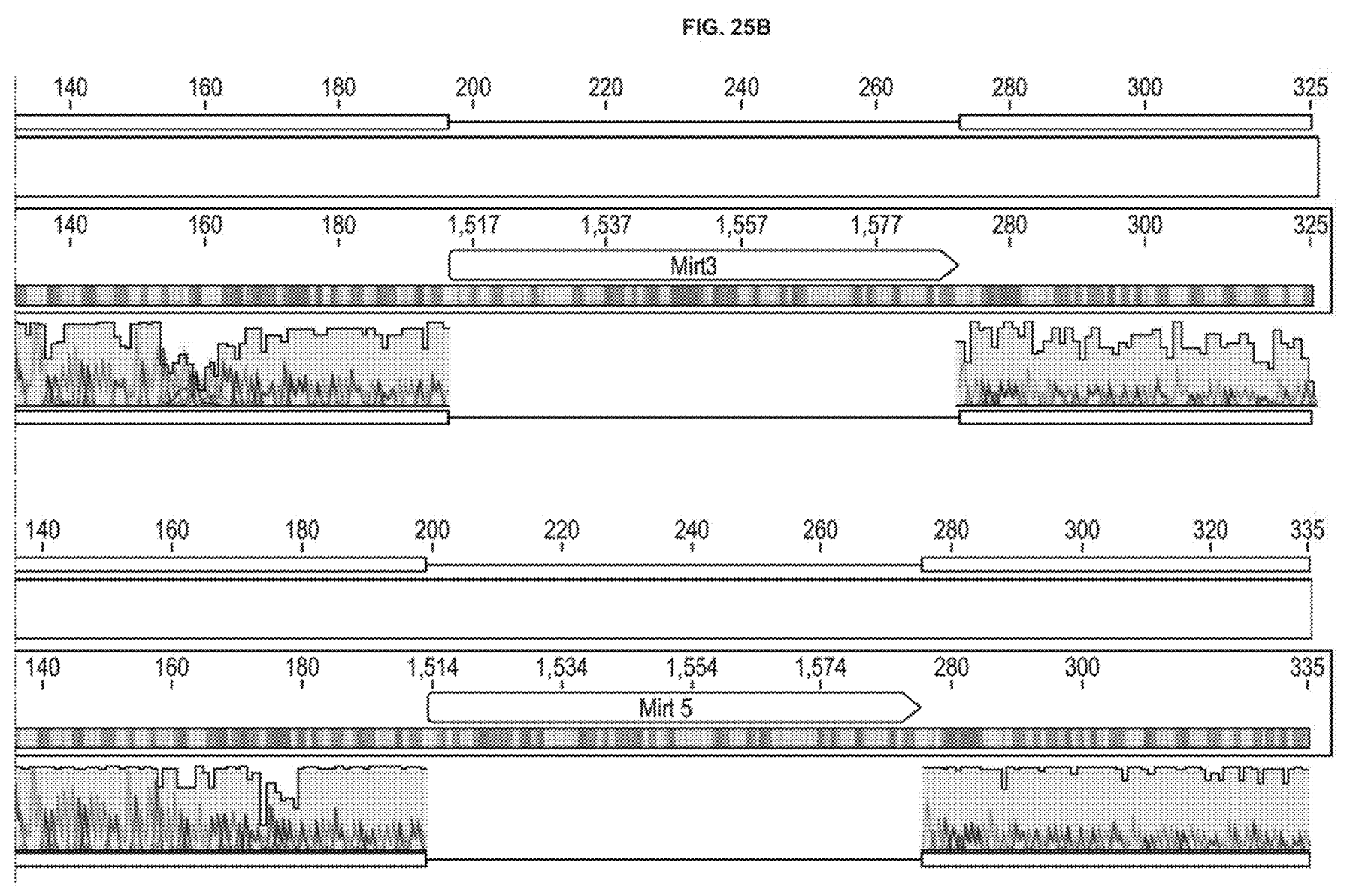

FIGS. 25A-25B Splice analysis of tandem 5'-UTR mirtrons. Sanger sequencing confirmed independent and precise splicing of tandem mirtrons in the 5'-UTR of GFP.

Figure 26:
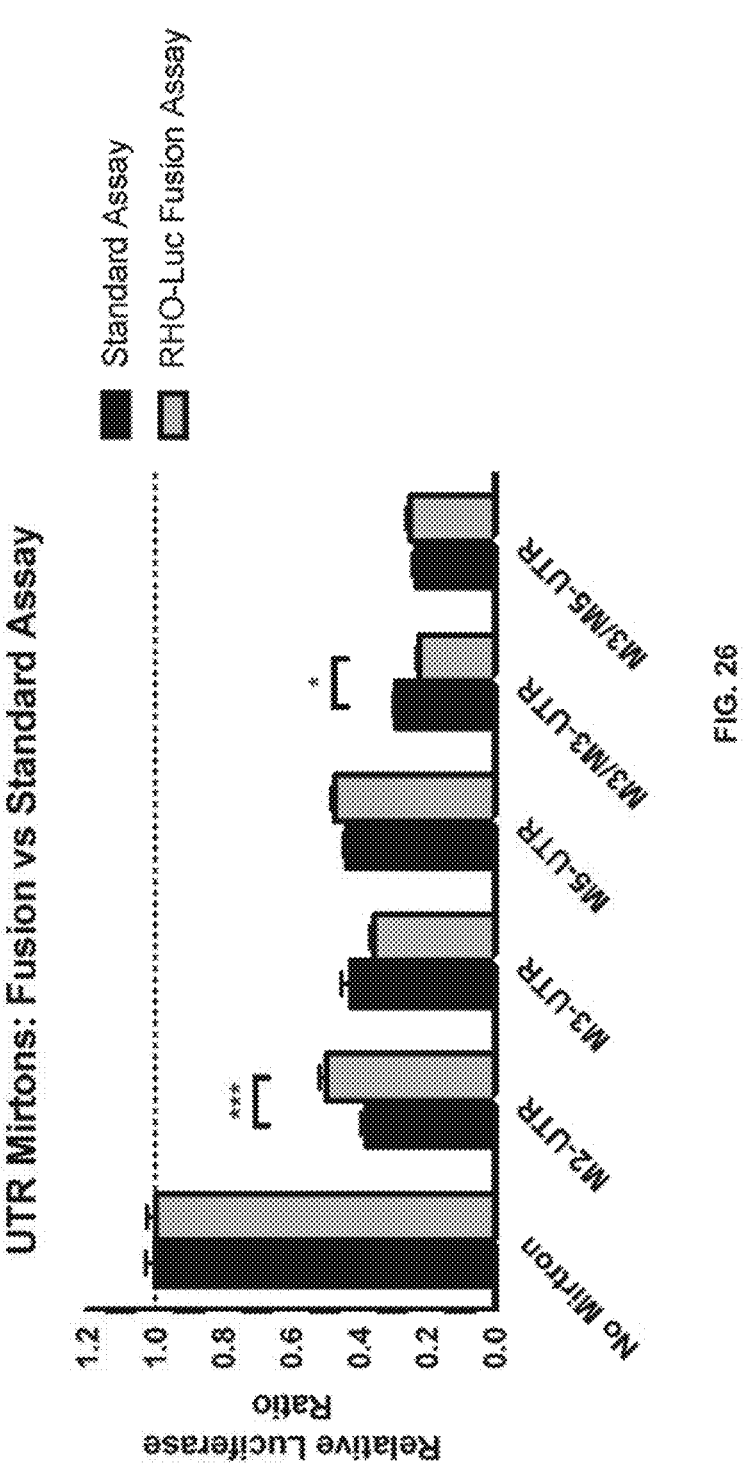

FIG. 26 Mirtrons located within the 5'-UTR of GFP effectively knock down the RHO-Luciferase fusion protein. *p<0.05; ***p<0.001 Two-way ANOVA Sidak's multiple comparison test.

FIG. 27 Reporter gene expression of 5'-UTR mirtrons. HEK293 cells transfected with 5'-UTR mirtron-GFP constructs were compared with that of CAG.GFP.WPRE. n=6; ****p<0.0001, one-way ANOVA Dunnett's multiple comparisons test.

Figure 28:
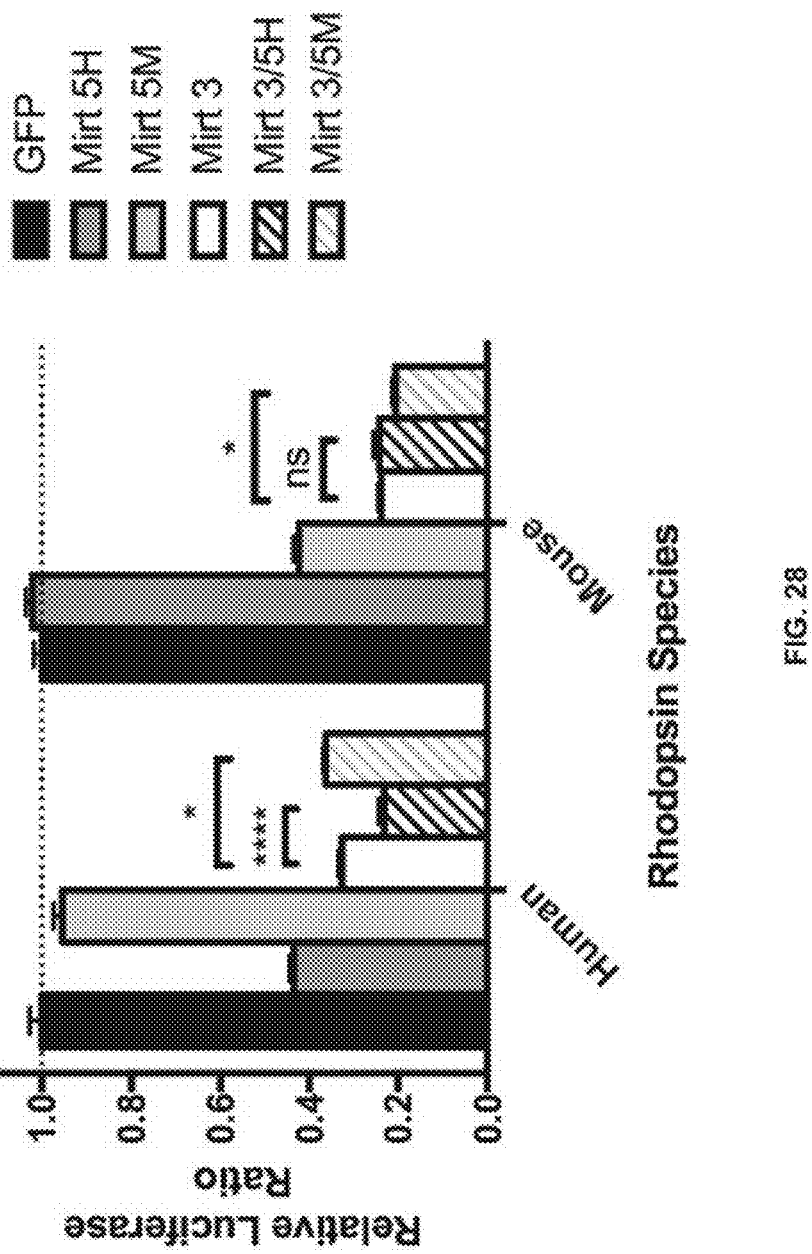

FIG. 28 M3/M5H-UTR (red arrows) achieves>75% knock-down of both human and mouse rhodopsin.

Figure 29:
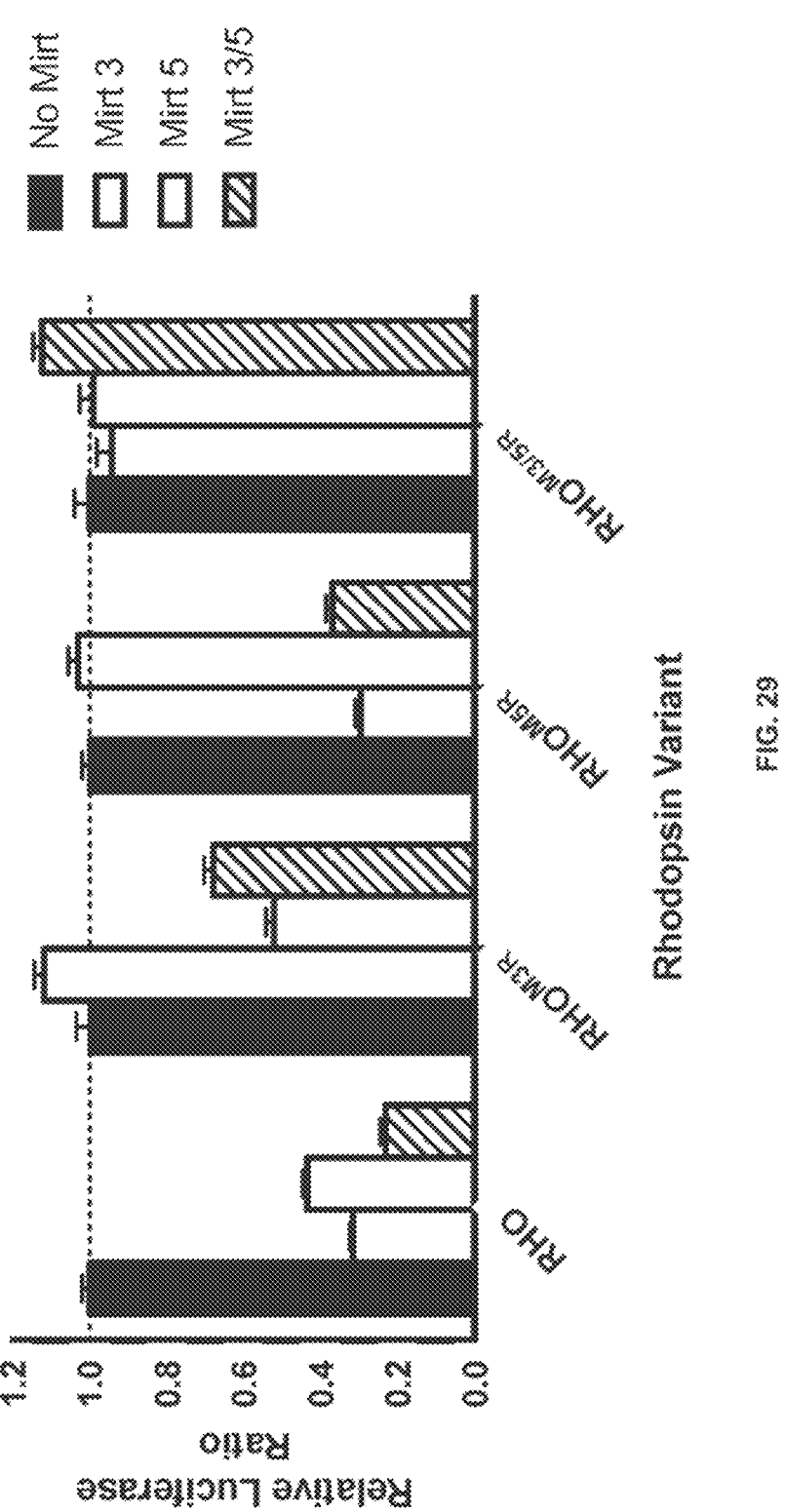

FIG. 29 Codon modification of rhodopsin confers resistance to mirtrons

Figure 30A:
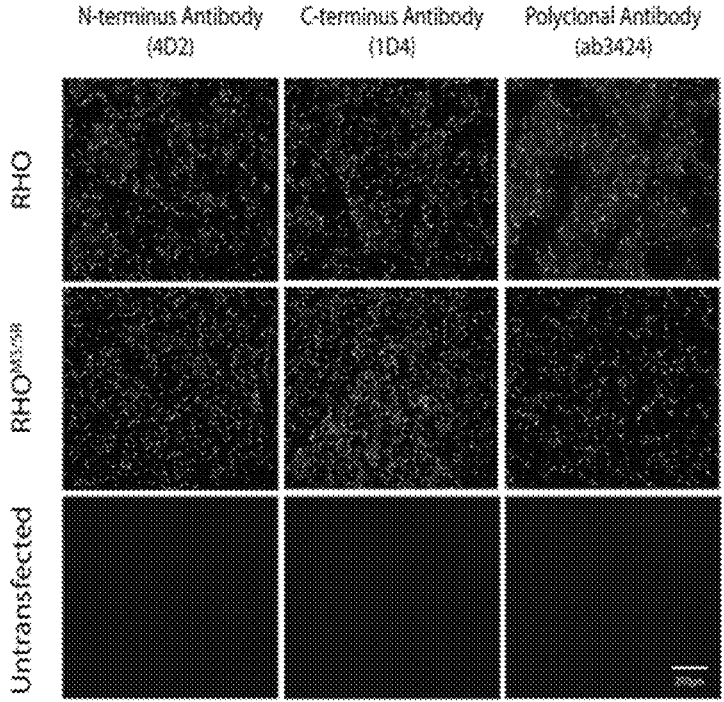
Figure 30B:
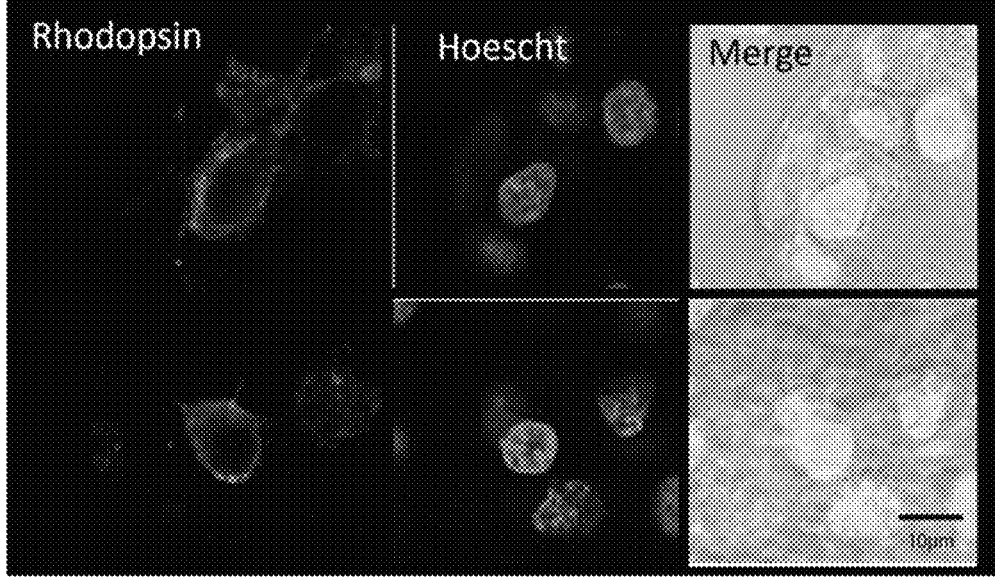

FIGS. 30A-30B The RHO$^{M3/5R}$ sequence leads to expression of rhodopsin in vitro. (A) Rhodopsin protein translated from both RHO and RHO$^{M3/5R}$ is recognised by an N-terminus specific monoclonal antibody (4D2, Abcam), a C-terminus specific antibody (1D4, Abcam) and a polyclonal antibody (ab3424, Abcam). (B) Rhodopsin traffics to the plasma membrane in both instances.

Figure 31:
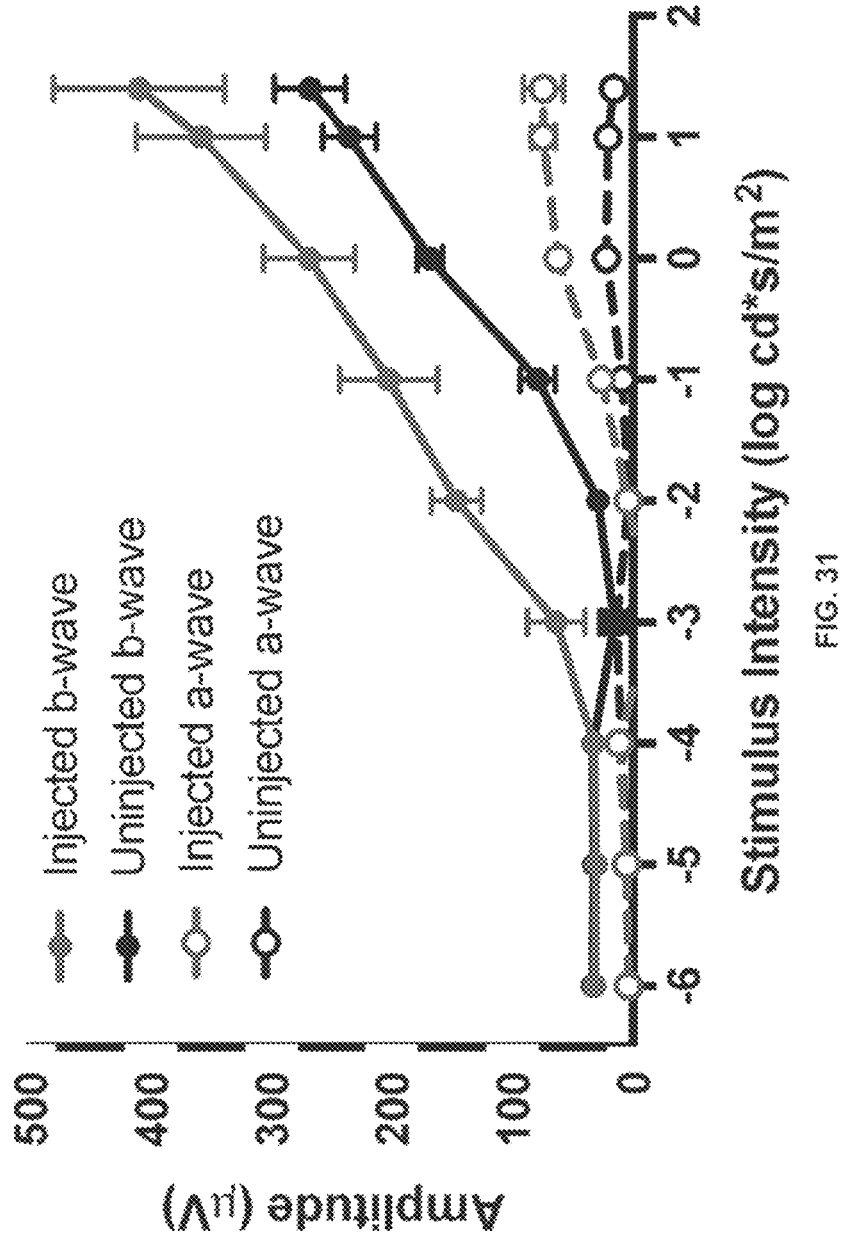

FIG. 31 RHO$^{M3/5R}$ is capable of driving the rod-derived electroretinogram.

Dark-adapted intensity-response curves for a- and b-waves derived from injected right and uninjected left eyes of Rho$^{-/-}$ mice four weeks post injection. Two-way ANOVA for effect of injection p=0.0022 for a-wave and p=0.0043 for b-wave.

Figure 32:
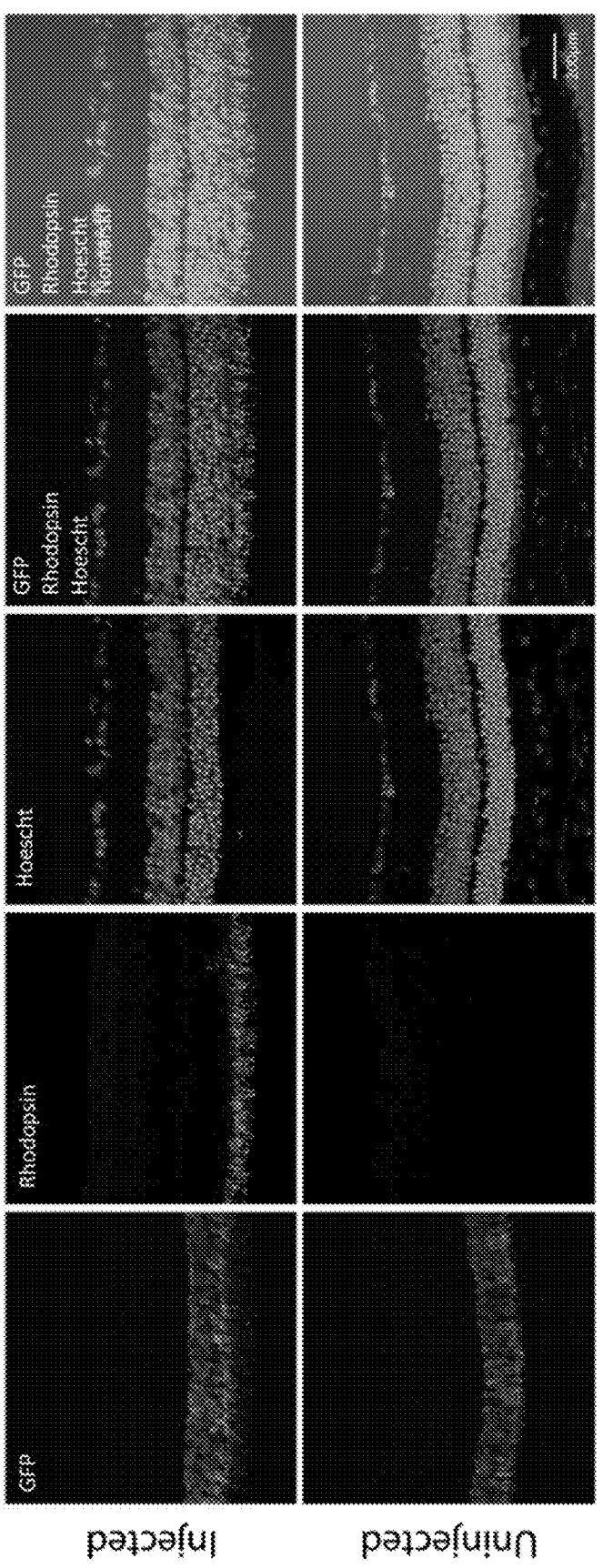

FIG. 32 Rhodopsin translated from the RHO$^{M3/M5R}$ transcript traffics to outer segments. Nrl.GFP/Rho$^{-/-}$ mice (in which rods are labelled with GFP) received unilateral subretinal injections of AAV2/8$^{Y733F}$.RHOp.Ex/Int.M3/M5.RHO$^{M3/5R}$.WPRE. Four weeks later, animals were sacrificed and retinal sections immunostained for rhodopsin (red).

Figure 33:
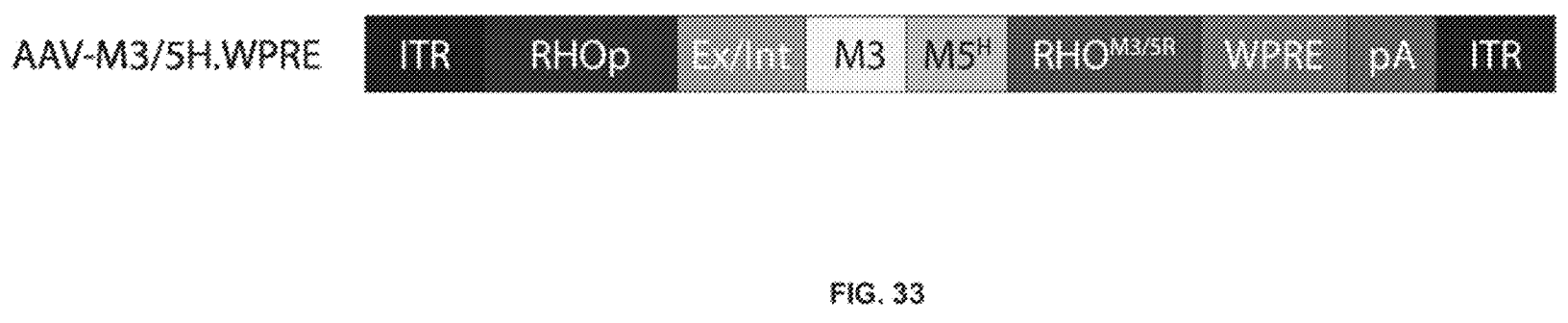

FIG. 33 Genome of the 'block' and replace' AAV vector

FIGS. 34A-34B cDNA derived from AAV-injected Rho$^{P23H/+}$ retinas at low dose (2×10$^8$gc) and high dose (2×10$^9$gc) was used as template for PCR with primers spanning the mirtron regions of the transcript. The gel above shows that the primary PCR product corresponds in size to that expected from transcripts where both mirtrons are individually spliced out: >90% based on band densitometry (left).

FIG. 35 mRNA analysis: Mirtron 3 induces knock-down of mouse rhodopsin in vivo. No significant reduction in mRho was noted at low or high dose after delivery of AAV-Ex/Int which contains no mirtrons. When the mirtron-containing vector was delivered at high dose, a 34% knockdown in total retinal mRho mRNA was evident compared with fellow sham-injected eyes P=0.0024, 2-way ANOVA Sidak's multiple comparison test. No significant knockdown was seen at low dose.

Figure 36:
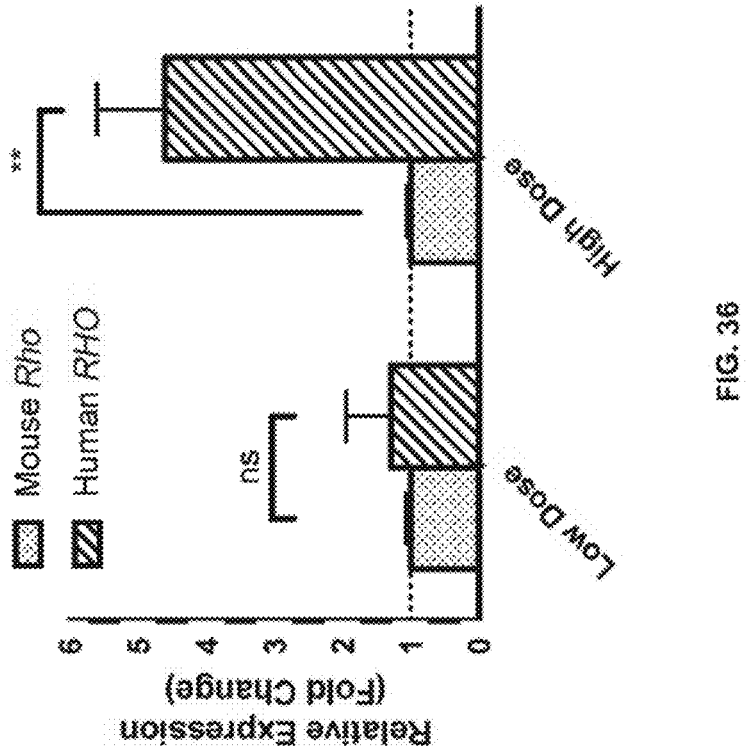

FIG. 36 mRNA analysis continued: human RHO supplementation levels after delivery of AAV-M3/5$^H$. RHO$^{M3/5R}$.WPRE. 'Replacement' with human RHO expressed as a fold change relative to native mouse Rho levels in fellow sham-injected eyes. At low dose, RHO supplementation approximates to native levels. At high dose, a 4.6 fold increase is seen, (P=0.0011, 2-way ANOVA Sidak's multiple comparison test) suggesting a degree of overexpression.

Figure 37:
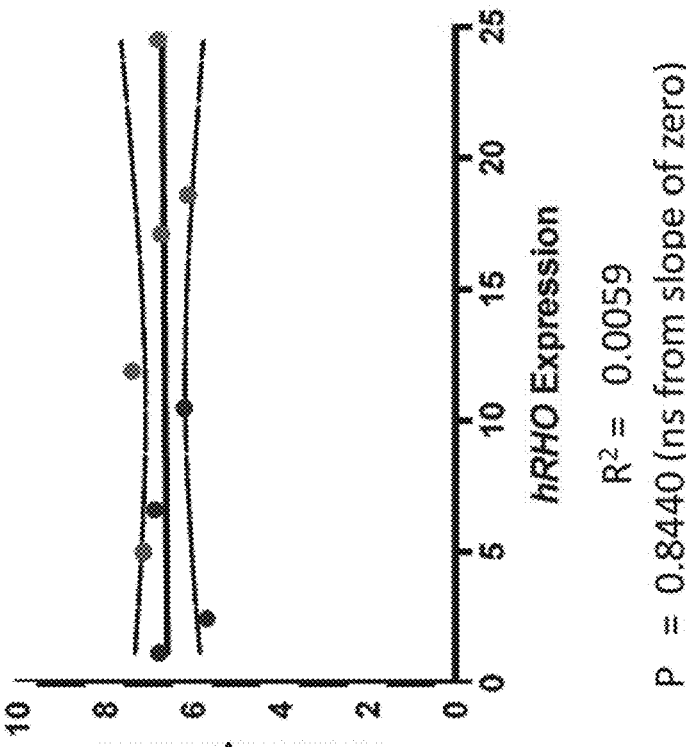

FIG. 37 mRNA analysis continued. Human RHO expression correlates with mRho knockdown in eyes treated with the mirtron-containing vector (right) but not with the AAV without Mirtron 3 (left). Together, this gene expression analysis represents the first demonstration of function of an artificial mirtron in vivo.

Figure 38:
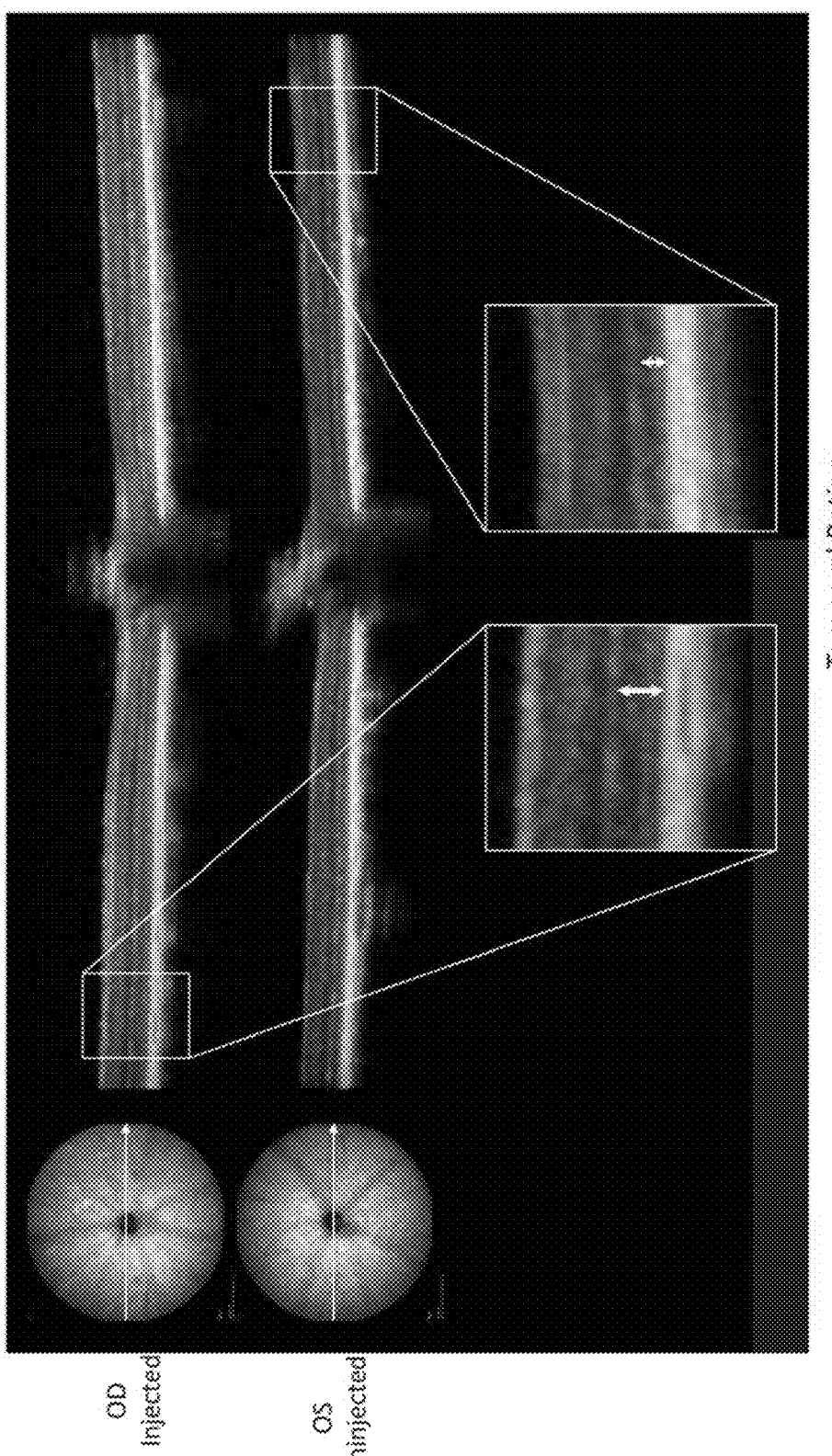

FIG. 38 Relative rescue of photoreceptor layer thickness (yellow arrows) in P23H eyes injected with 2×10$^8$ gc of AAV-M3/5.RHO. Representative SD-OCT images taken along the horizontal meridian in a treated mouse. PRL thickness was greater in injected than in uninjected eyes in the temporal and nasal retina (both p<0.0001 2-way ANOVA, Sidak's multiple comparison test). No significant difference was detected for superior retinal locations (likely due to the effect of retinal detachment) or inferior locations (likely due to insufficient dose).

Figure 39:
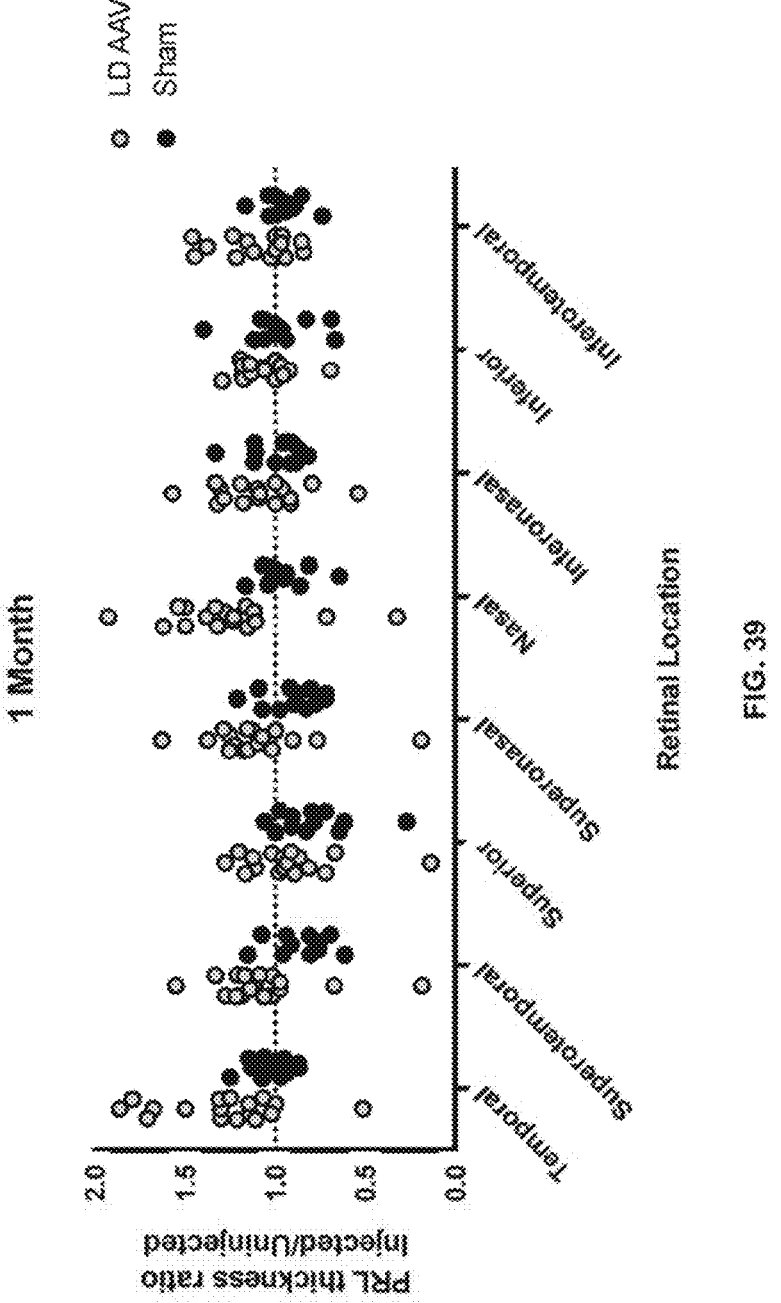

FIG. 39 Early evidence that subretinal delivery of low dose (LD: 2×10$^8$gc) AAV-M3/5.RHO leads to relative preservation of the photoreceptor layer (PRL) as measured in vivo by SD-OCT. The ratio of PRL thickness in injected versus uninjected eyes is shown as a function of retinal location for LD and sham-injected groups 1 month post-injection. Note increased retinal thickness (ratio>1) in LD but not in sham-injected eyes along the horizontal meridian (nasal and temporal retina).

Figure 40:
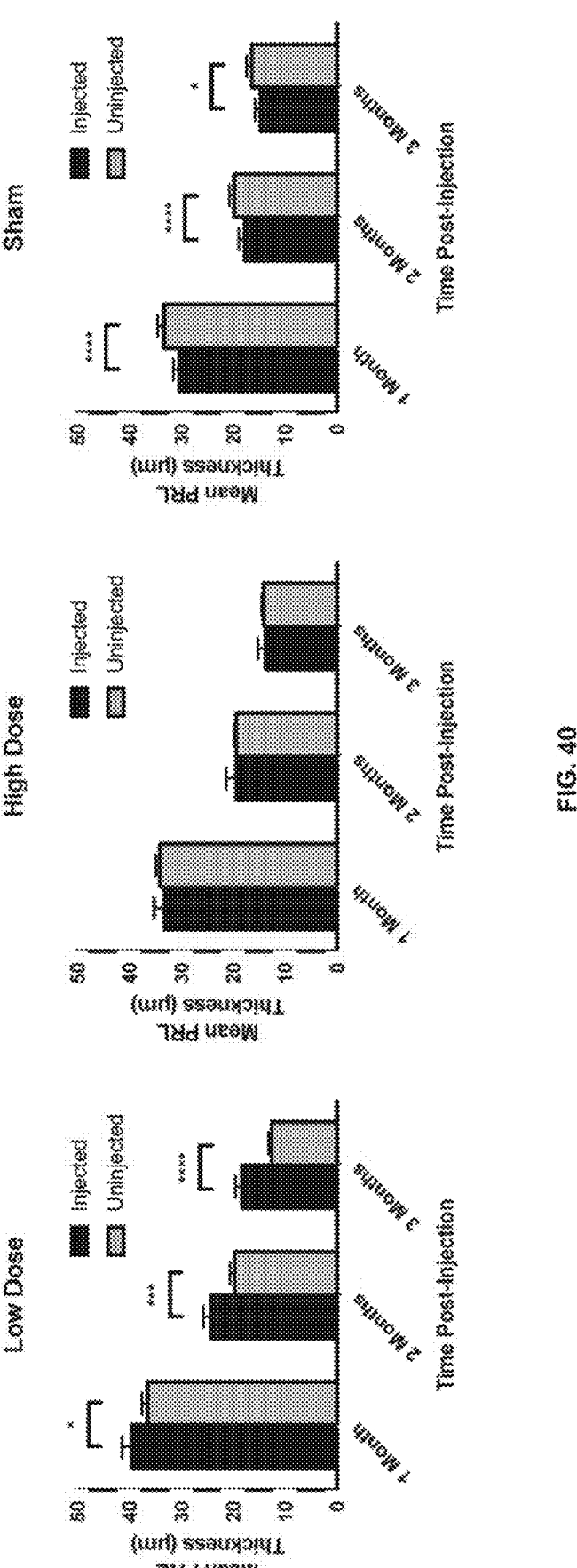
Figure 41:
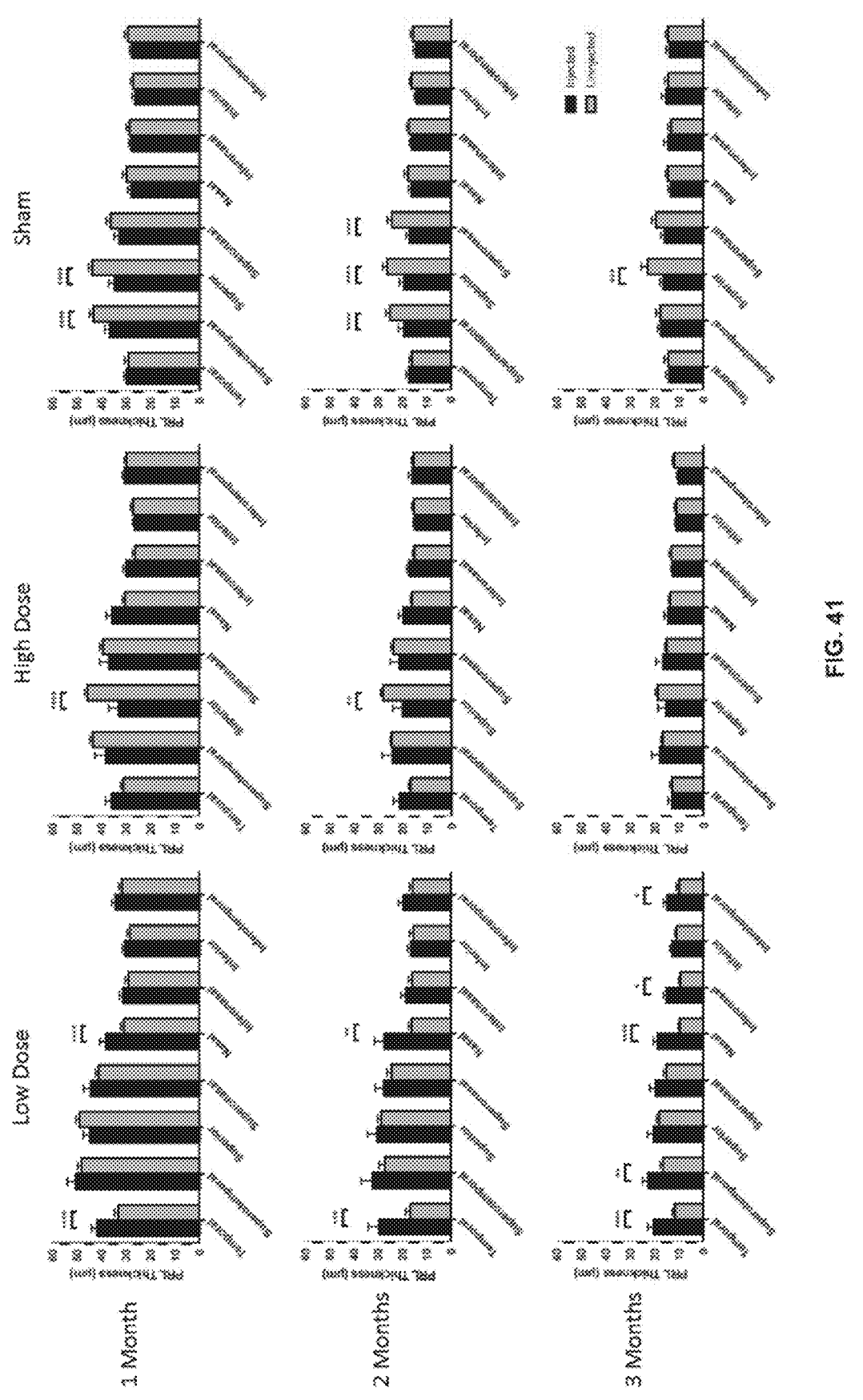
Figure 42:
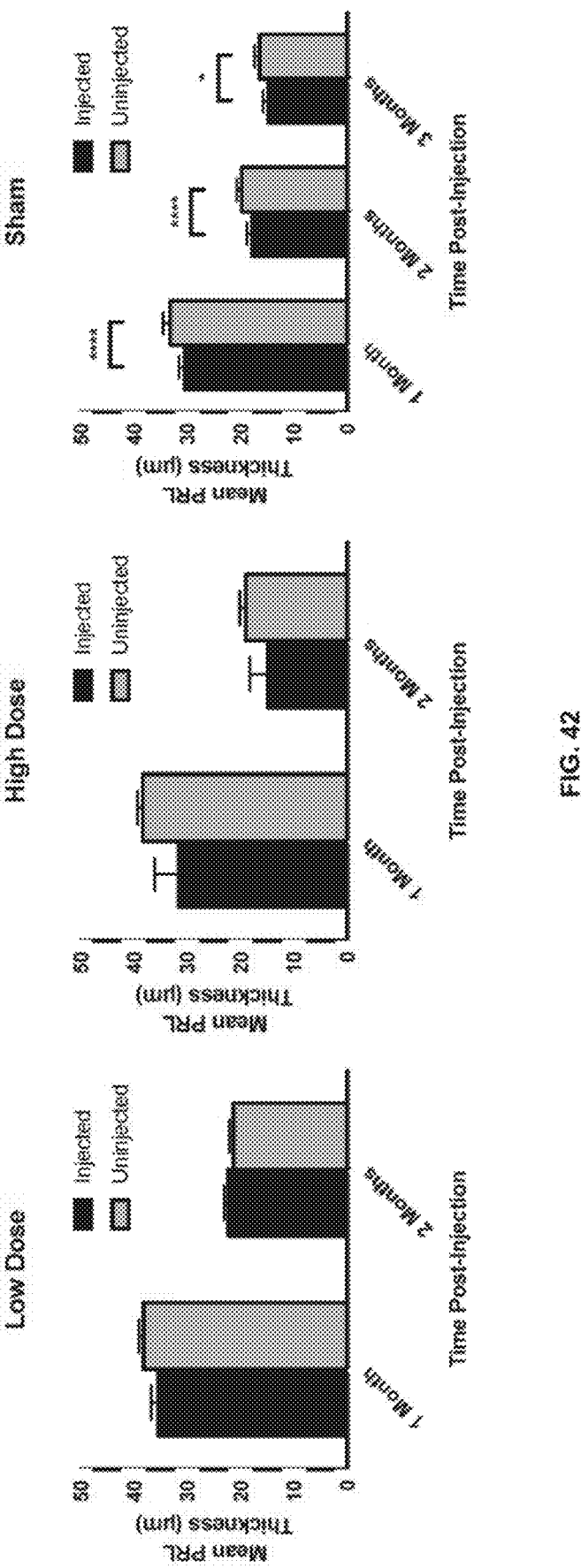

FIG. 40 OCT analysis looking for treatment effect. OCT provides non-invasive in vivo cross-sectional imaging of the retina. For all cohorts, right eyes were injected and left eyes were uninjected as controls. A small but significant positive effect on overall photoreceptor layer (PRL) thickness was seen in the low dose cohort whilst a small but significant damaging effect was seen for the sham group (attributable to surgery). No significant change in overall mean PRL thickness was seen in the high dose injected eyes. Vector=AAV.RHOp.Ex/Int.M3.M5$^H$.RHO$^{M3/5R}$.WPRE FIG. 41 OCT analysis for the three groups by retinal location following superior subretinal injection. Vector=AAV.RHOp.Ex/Int.M3.M5$^H$.RHO$^{M3/5R}$.WPRE FIG. 42 OCT analysis with AAV-Ex/Int vector. Data shown is 1 and 2 months post-injection. Compared with equivalent data from vector with mirtrons (FIG. 7), no benefit is seen at low dose and high dose appears more damaging.

Figure 43:
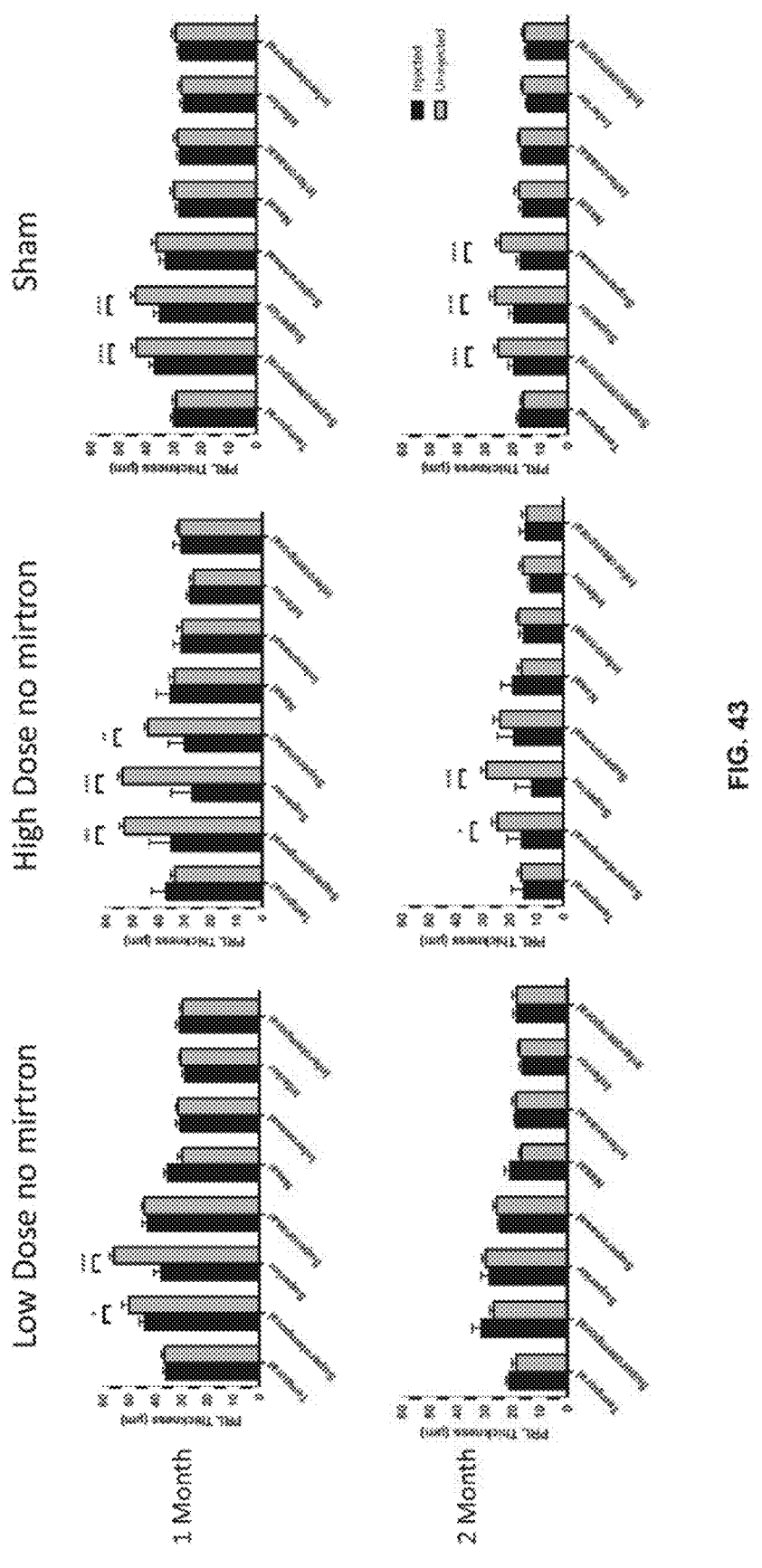

FIG. 43 OCT analysis for the three groups by retinal location following superior subretinal injection. Again, compared with FIG. 8 (data for vector with mirtrons), no benefit seen at low dose and high dose appears more damaging. Vector=AAV.RHOp.Ex/Int. RHO.WPRE FIG. 44 Dark-adapted ERG analysis. ERG measures electrical signal from the retina, a-wave is from photoreceptors, b-wave from inner retina. Small benefit seen at low dose, whilst high dose and sham seem to have small deleterious effects.

Figure 45:
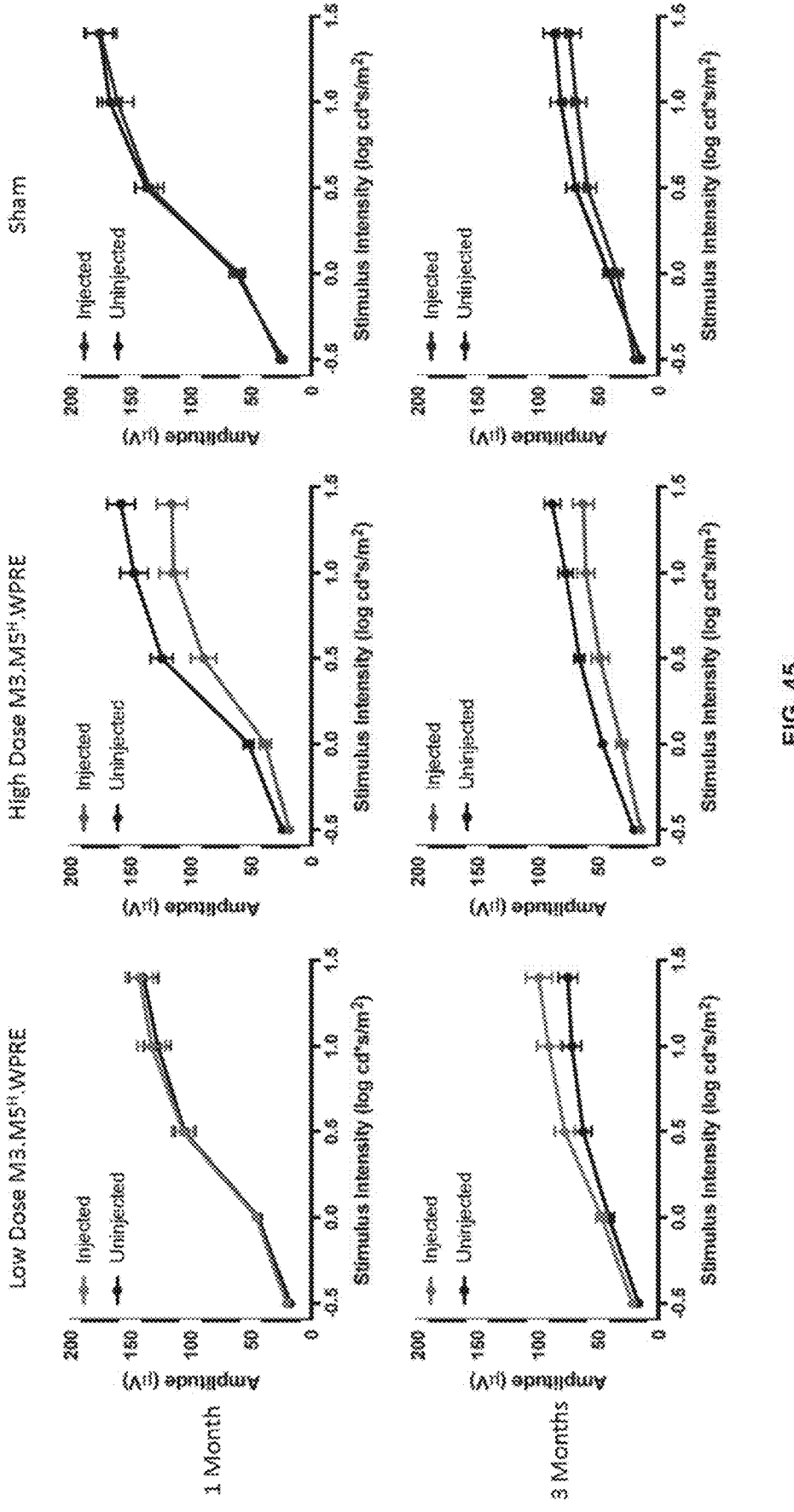

FIG. 45 Light-adapted ERG analysis. Represents signal from cone photoreceptors. Small benefit seen at low dose, whilst high dose and sham seem to have deleterious effects, more so in high dose group.

Figure 46:
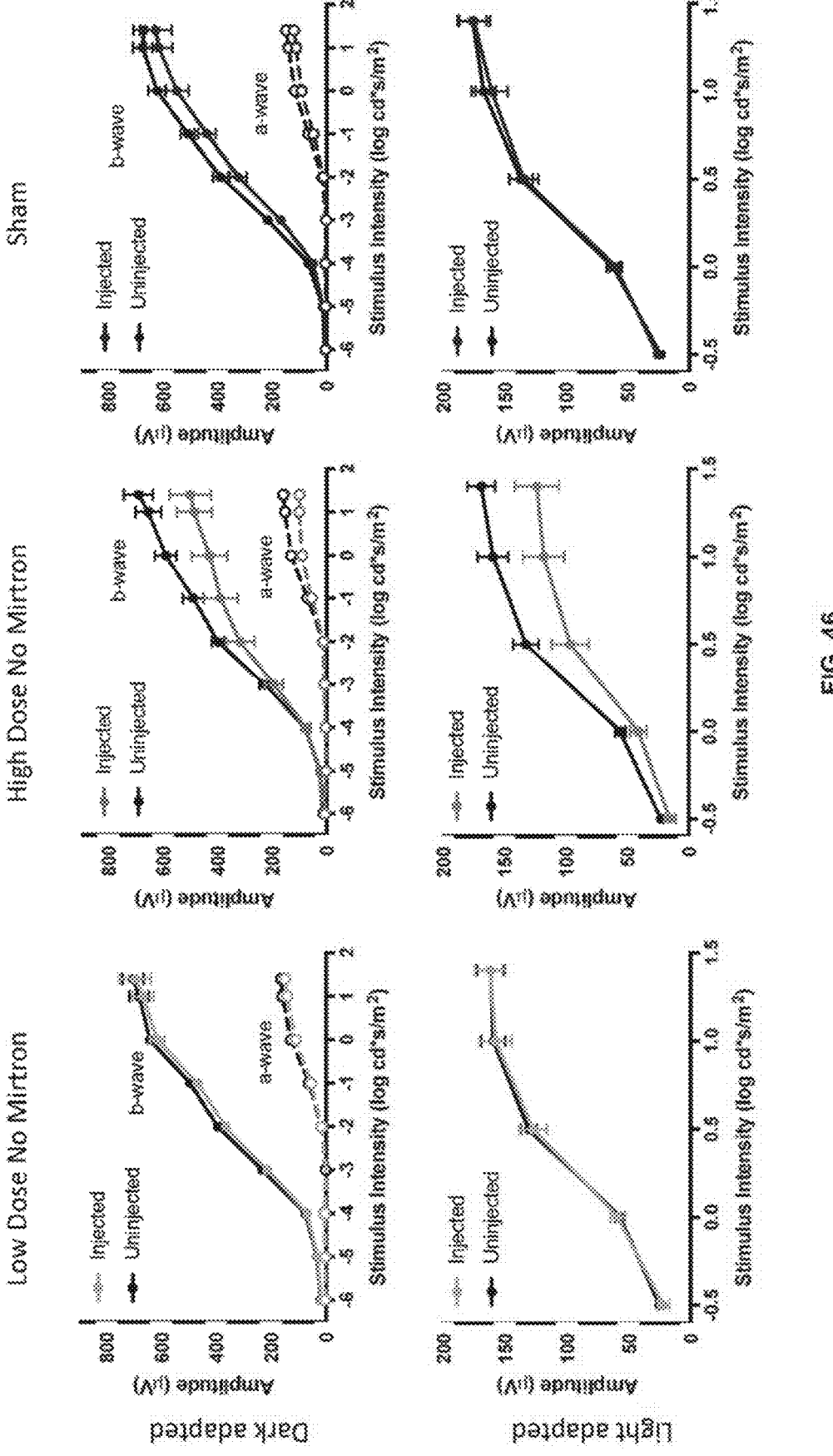

FIG. 46 One month dark- and light-adapted ERG analysis following delivery of AAV.RHOp.Ex/Int. RHO.WPRE.

Figure 47:
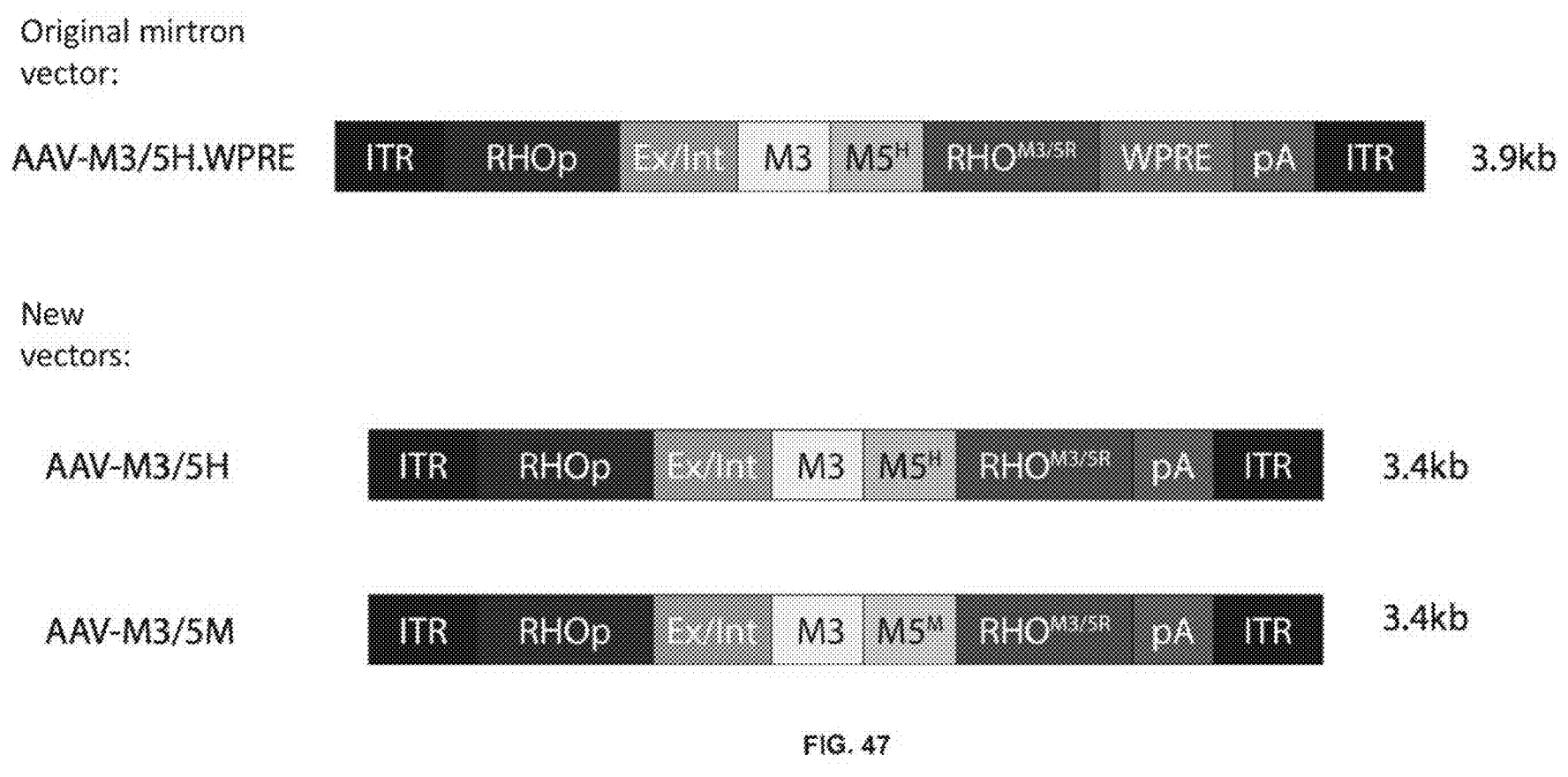

FIG. 47 New AAV vectors without the WPRE.

Description of the Sequences

SEQ ID NOs: 1, 2 set forth human rhodopsin CDS and amino acid sequences.

SEQ ID NOs: 3 to 9 set forth target sequences in rhodopsin gene of mirtrons 1 to 7

SEQ ID NOs 10 to 16 set forth the polynucleotide sequences of mirtrons 1 to 7.

SEQ ID NOs 17 to 23 set forth the guide strand sequences of mirtrons 1 to 7.

SEQ ID NOs: 24, 25 set forth modified target sequences that are resistant to mirtrons 3, 5.

SEQ ID NO: 26 sets forth mirtrons 3 and 5 with 5', 3' and intervening ESE-rich sequences derived from eGFP CDS.

SEQ ID NO: 27 set forth the 5'UTR sequence of vector AAV2/8$^{Y733F}$.RHOp.Ex/Int.M3/M5.RHO$^{M3/5R}$.WPRE.

SEQ ID NO: 28 set forth the ITRs and intervening transgene sequence of vector AAV2/8$^{Y733F}$.RHOp.Ex/Int.M3/M5.RHO$^{M3/5R}$.WPRE.

SEQ ID NO: 29 sets forth the WPRE sequence.

SEQ ID NO: 30 sets forth the BstB1 restriction site and adjacent 3' 'G'

SEQ ID NO: 31 sets the polynucleotide sequence of vector AAV2/8$^{Y733F}$.RHOp.Ex/Int.M3/M5.RHO$^{M3/5R}$. WPRE SEQ ID NOs: 32 and 33 set forth AAv2 forward and reverse ITR sequences SEQ ID NO: 34 sets forth the sequence of the human rhodopsin promoter SEQ ID NOs: 35, 36 set forth eGFP CDS and amino acid sequences.

SEQ ID NO: 37, 38 set forth the ESE-rich 5' and 3' flanking sequences

SEQ ID NO: 39 sets forth a 5'UTR sequence without mirtrons

SEQ ID NO: 40 sets forth an ESE-rich sequence

SEQ ID NOs: 41 to 47 set forward oligonucleotide sequences for mirtrons 1- to 7

SEQ ID NOs: 48 to 54 set reverse oligonucleotide sequences for mirtrons 1- to 7

SEQ ID Nos: 55 to 57 set forth mirtron, forward oligonucleotide and reverse oligonucleotide sequences for mirtron M5$^{M}$.

SEQ ID Nos: 58 to 60 set forth mirtron, forward oligonucleotide and reverse oligonucleotide sequences for mirtron M2U-M2.

SEQ ID Nos: 61 to 63 set forth mirtron, forward oligonucleotide and reverse oligonucleotide sequences for mirtronScr-M2.

SEQ ID NO: 64 sets forth polynucleotide sequence of vector

AAV2/8$^{Y733F}$.RHOp.Ex/Int.M3/M5.RHO$^{M3/5R}$

SEQ ID NO: 65 sets forth polynucleotide sequence of vector

AAV2/8$^{Y733F}$.RHOp.Ex/Int.M3/M5M.RHO$^{M3/5R}$

DETAILED DESCRIPTION

Mirtrons

A mirtron is a hairpin intron that is spliced out and functions as a microRNA. Mirtrons may be capable of inhibiting gene expression of a target mRNA through the process of RNA interference (RNAi). The term "mirtron" as referred to herein includes classical mirtrons, in which the 5' and 3' splice sites are located near the base of the hairpin, and 5' or 3' tailed mirtrons, which may be further processed by exonuclease digestion after splicing.

Considerations that may be taken into account when designing artificial mirtrons have been described previously in, for example, Seow et al. (*RNA* (2012) 18:1328-1337) and Kock et al. (*Nucleic Acids Research* (2015).

Each mirtron begins with the splice donor motif ('GT') and ends with the splice acceptor motif ('AG'). The stem of the hairpin comprises a guide strand and a complementary passenger strand. The guide strand is designed to recognise a target mRNA sequence by complementary Watson-Crick base pairing. Mismatches may be introduced at the base of the hairpin in the passenger strand to facilitate correct strand selection by the RNA-induced silencing complex (RISC), as for examples described in Schwarz et al. (2003, Cell 115 (2): 199-208). To maintain efficacy the guide strand complements the target sequence.

The guide strand may be typically at least 15, 16, 17, 18, 19, 20 or 21 nucleotides in length, and up to 21, 22, 23, 24, 25, 30, 35, 40, 45, 50 or more nucleotides in length. In some cases the guide strand is between 18 and 23 nucleotides in length or 21 nucleotides in length. The guide strand may in some cases be less than 20, 15, 14, 13, 12, 11, 10, 9, 8, 7, 6, 5, 4, 3, 2 or 1 nucleotides from the 5' splice donor motif. The guide strand and/or the passenger strand may comprise a T or more typically an A at position 21. The guide strand and/or the passenger strand may comprise an A position 5. The guide strand and/or the passenger strand may comprise three or more A's or T's in the last 5 nucleotides. The guide strand and/or the passenger strand may comprise an A, C or T at position 15. The guide strand and/or the passenger strand may comprise an A position 8.

In between the guide strand and the passenger strand is a hairpin loop. The hairpin loop may be typically 5, 6, 7, 8 or 9 to 9, 10, 11, 12, 13, 14, 15, 20, 25, 30, 35 or more nucleotides in length. In some cases the hairpin loop is 8 to 12 nucleotides in length. In some cases the hairpin loop is 9 nucleotides in length and/or comprises the sequence TTCAAGAGA (SEQ ID NO: X).

The lariat branch point is located either in the hairpin loop (classical and 5' tailed mirtrons) or near the 3' end of the hairpin structure, typically within 1, 2, 3, 4, 5, 6, 7, 8, 9, 10, 11, 12, 13, 14 or 15 nucleotides 5' or 3' of the end of the hairpin (3' tailed mirtrons). In 3' tailed mirtrons the hairpin may in some cases end within 3, within 2 or within 1 nucleotide of the lariat branch point.

Downstream of the hairpin is a polypyrimidine tract and an AG splice acceptor motif. The polypyrimidine tract may typically comprise at least six uninterrupted polypyrimidines. Further, the polypyrimidine tract may typically comprises a stretch of at least 10 polypyrimidines with at most one purine interruption, or a stretch of at least 13 polypyrimidines with at most two purine interruptions, or a stretch of at least 16 polypyrimidines with at most three purine interruptions.

At a molecular level, a mirtron-based gene therapy strategy offers a number of advantages over other gene knockdown or 'block and replace' approaches taken previously:

a. The mirtron released after splicing is precisely defined by the splice donor and acceptor mRNA sequences which means that the resulting short hairpin RNA is likely to be associated with fewer off-target effects that may arise following aberrant miRNA processing from PolIII class promoters.

b. Mirtron processing is Drosha-independent which may reduce the likelihood of toxicity related to miRNA pathway saturation.

c. As intronic sequences, mirtrons may be co-expressed together with a 'hardened' transgene transcript under the same PolII promoter. This allows for perfect matching of 'blockage' and 'replacement' and avoids any imbalances that may result when different promoters or vectors are used for the knock-down and replacement arms of the treatment, strategies employed by other researchers. Indeed, using separate promoters may in fact make a disease process worse if the promoter driving the replacement transcript were to be silenced with time.

Block and Replace

The present invention is concerned with the design, production and use of gene therapy vectors that comprise mirtrons to knock down the expression of a gene expressed in the retina. Such a gene may be referred to herein as a "target gene" or the "gene targeted by the mirtron". A mirtron can knock down expression of a target gene if the polynucleotide sequence of the guide strand of the mirtron complements (and therefore "recognises") a polynucleotide sequence that is present in the target gene. The polynucleotide sequence in the target gene that complements the guide strand of the mirtron may be referred to herein as a "target sequence". The target gene may be any gene that is expressed in the retina of a subject where the subject would receive therapeutic benefit from a reduction in the expression of the gene in the retina, either alone or in combination with other therapeutic measures, such as co-expression of a transgene as discussed below.

In some cases in accordance with the invention, the target gene is rhodopsin. Rhodopsin is a photosensitive receptor protein expressed in rod photoreceptor cells of the retina. The CDS of human rhodopsin may have the polynucleotide sequence of SEQ ID NO: 1 and encode human rhodopsin protein having the amino acid sequence of SEQ ID NO: 2. Therefore a mirtron in accordance with the present invention for rhodopsin knock down may comprise any suitable guide strand sequence as described above that complements a sequence comprised within the sequence of SEQ ID NO: 1 or any variant or homologue thereof that encodes a functional rhodopsin protein. In some cases the mirtron guide strand may complement a rhodopsin polynucleotide sequence selected from any one of SEQ ID NOs: 3 to 9 or a nucleotide sequence having at least 80%, 85%, 90%, 95%, 98% or 99% sequence identity to any one of SEQ ID NOs: 3 to 9. In some cases in accordance with the present invention the mirtron has the polynucleotide sequence of any one of SEQ ID NOs: 10 to 16 and/or a guide strand sequence comprising or consisting of the polynucleotide sequence of any one of SEQ ID NOs: 17 to 23, and/or complements a target sequence comprising a polynucleotide sequence selected from SEQ ID NOs: 3 to 9.

In some cases the vector further comprises a gene for expression of a protein in the retina. This gene may be referred to herein as a "transgene". The transgene may be any gene the expression of which in the retina would provide therapeutic benefit to a subject, either alone or in combination with other therapeutic measures, such as co-expression of a mirtron.

In some cases the transgene is a variant of the gene that is targeted by the mirtron. Thus if the mirtron is for rhodopsin knock down then the transgene may be a variant rhodopsin gene. Such a vector may be used to both knock down expression of a protein in the retina using the mirtron and to replace it with expression of the variant protein. This may be referred to as "block and replace" treatment or use of a "block and replace" vector. The variant gene is selected to be resistant or "hardened" to knock down by the mirtron. Typically the variant gene differs from the target gene in the polynucleotide target sequence that is recognised by the mirtron guide strand, typically by the substitution of one or more, in some cases 2, 3, 4, 5, 6, 7, 8, 9 or 10 or more nucleotides in the target sequence. For example, in the transgene one or more codons may be substituted compared with the codons in the target sequence recognised by the mirtron with alternative codons that encode the same amino acids. Ideally 'rare' codons are avoided. The transgene is not targeted for knock-down by the mirtron because the guide strand does not complement any sequence in the variant gene.

In some cases in accordance with the present invention the transgene is a variant rhodopsin gene that encodes functional rhodopsin but that does not comprise a sequence that is complementary to any one polynucleotide sequence selected from of SEQ ID NOs: 17 to 23, or does not comprise any specific combination of two or more polynucleotide sequences selected from of SEQ ID NOs: 17 to 23, or does not comprise any one polynucleotide sequence selected from SEQ ID NOs: 3 to 9, or does not comprise any specific combination of two or more polynucleotide sequences selected from of SEQ ID NOs: 3 to 9. In some cases the rhodopsin transgene comprises the polynucleotide sequence of SEQ ID NO: 24 and/or the polynucleotide sequence of SEQ ID NO: 25.

Vectors Comprising Multiple Mirtrons

The inventors have demonstrated successful delivery of two independently functional mirtrons in a single vector, both from the 5'UTR of the same transgene for expressing rhodopsin.

There are several reasons why it might be desirable to have multiple functional mirtrons in the same vector or embedded in the same transgene. Firstly, the inventors have demonstrated that the effect on target gene knock down of multiple mirtrons expressed from the same vector are additive. The mirtron guide strands may recognise the same or different sequences within the target gene. Using multiple mirtrons can thereby result in an increased or more robust knock-down effect on a target gene.

Secondly, including multiple mirtrons that recognise different sequences in the same target gene can ensure that a vector can be used to treat disease caused by mutations in any part of the target gene expressed in a subject in need of treatment. Significant mutational heterogeneity exists for example in the rhodopsin gene, so targeted suppression alone as a strategy is unlikely to be universally successful. However, if more than one mirtron is included in a gene therapy vector, then the vector is likely to be at least partly effective in knocking down expression of the target gene even in subjects that happen to have a mutation within the target sequence of one of the mirtrons.

Thirdly, multiple mirtrons could be used to knock down expression of multiple target genes using the same vector. This is particularly likely to be useful in the treatment of complex diseases in which several different genes are involved.

Fourthly it can be useful to include multiple mirtrons in a single vector for experimental purposes, for example to compare the relative efficacy of the mirtrons.

Accordingly in some cases in accordance with the present invention, the plasmid or vector may comprise two or more copies of the same mirtron, or two or more mirtrons that complement the same target sequence, or two or more different mirtrons that complement the different target sequences in the same or two or more different target genes.

In some cases the two or more mirtrons may each be embedded in the 5'UTR of a transgene for co-expression with the mirtrons. One or more or each of the mirtrons may be flanked by a polynucleotide sequence that comprises ESEs as described above.

In some cases the plasmid or vector comprises two or more mirtrons having one or more guide strand polynucleotide sequences selected from SEQ ID NO: 17 to 23, or two or more mirtrons having guide stands that complement one or more target polynucleotide sequences selected from SEQ ID NOs: 3 to 9, or two or more mirtrons having one or more polynucleotide sequence selected from SEQ ID NOs: 10 to 16. The target gene may be rhodopsin.

In some cases the plasmid or vector comprises a mirtron having a guide strand polynucleotide sequence that comprises or consists of the polynucleotide sequence of SEQ ID NO: 19 and a mirtron having a guide strand polynucleotide sequence that comprises or consists of the polynucleotide sequence of SEQ ID NO: 21; or a mirtron having a guide strand that complements a polynucleotide sequence that comprises or consists of the polynucleotide sequence of SEQ ID NO: 5 and a mirtron having a guide strand that complements a polynucleotide sequence that comprises or consists of the polynucleotide sequence of SEQ ID NO: 7; or a mirtron having the polynucleotide sequence of SEQ ID NO: 12 and a mirtron having the polynucleotide sequence of SEQ ID NO: 14.

In some cases the plasmid or vector comprises the polynucleotide of SEQ ID NO: 26, or a polynucleotide sequence having at least 80%, 85%, 90%, 95%, 95% or 99% sequence identity with SEQ ID NO: 26, provided that the sequence comprises the mirtrons or guide strands and/or the ESE motifs as defined above. In some cases the plasmid or vector comprises a transgene having a 5'UTR comprising or consisting of the polynucleotide sequence of SEQ ID NO: 27 or a sequence having at least 80%, 85%, 90%, 95%, 95% or 99% sequence identity with SEQ ID NO: 27 and provided that the sequence comprises the mirtrons or guide strands and/or the ESE motifs or the sequence of SEQ ID NO: 26. In some cases the plasmid or vector comprises a polynucleotide sequence selected from SEQ ID NO: 28, or a variant of SEQ ID NO: 28 in which the WPRE sequence (SEQ ID NO: 29) is deleted and/or the mirtron of SEQ ID NO: 14 (mirtron M5$^H$) is replaced by a mirtron comprising SEQ ID NO: 49 (mirtron M5M). In some cases the plasmid or vector comprises or consists of the polynucleotide sequence of SEQ ID NO: 31, or a variant of SEQ ID NO: 31 in which the WPRE sequence (SEQ ID NO: 29) is deleted and/or the mirtron of SEQ ID NO: 14 (mirtron M5$^H$) is replaced by a mirtron comprising SEQ ID NO: 49 (mirtron M5$^M$).

Vectors

In some embodiments, the invention relates to plasmids, vectors, or gene therapy vectors. A gene therapy vector is any vector suitable for use in gene therapy, i.e. any vector suitable for the therapeutic delivery of nucleic acid polymers into target cells, such as photoreceptor cells or retinal pigment epithelium (RPE) cells, of the retina of a patient. The vector may be of any type, for example it may be a plasmid vector or a minicircle DNA. Typically, the vector is a viral vector. The viral vector may for example be derived from an adeno-associated virus (AAV), a retrovirus, a lentivirus, a herpes simplex virus, or an adenovirus.

AAV Derived Vectors

The vector may comprise an AAV genome or a derivative thereof. An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly, the AAV genome of the vector of the invention is typically replication-deficient.

The AAV genome may be in single-stranded form, either positive or negative-sense, or in double-stranded form. The use of a double-stranded form allows bypass of the DNA replication step in the target cell and so can accelerate transgene expression.

Typically, the AAV genome of a naturally derived AAV comprises at least one inverted terminal repeat sequence (ITR). An ITR sequence acts in cis to provide a functional origin of replication, and allows for integration and excision of the vector from the genome of a cell. The AAV genome may also comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

A promoter may be operably linked to each of the packaging genes. Specific examples of such promoters include the p5, p19 and p40 promoters (Laughlin et al., 1979, PNAS, 76:5567-5571). For example, the p5 and p19 promoters are generally used to express the rep gene, while the p40 promoter is generally used to express the cap gene.

The AAV genome may be from any naturally derived serotype or isolate or clade of AAV. Thus, the AAV genome may be the full genome of a naturally occurring AAV virus. As is known to the skilled person, AAV viruses occurring in nature may be classified according to various biological systems.

Commonly, AAV viruses are referred to in terms of their serotype. A serotype corresponds to a variant subspecies of AAV which, owing to its profile of expression of capsid surface antigens, has a distinctive reactivity that can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10 and AAV11, also recombinant serotypes, such as Rec2 and Rec3, identified from primate brain. The genome serotype of AAV for use in the invention may, for example, be AAV2. Reviews of AAV serotypes may be found in Choi et al. (*Curr Gene Ther.* 2005; 5(3); 299-310) and Wu et al (*Molecular Therapy.* 2006; 14(3), 316-327).

The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognisably distinct population at a genetic level.

Examples of clades and isolates of AAV that may be used in the invention include:

Clade A: AAV1 NC_002077, AF063497, AAV6 NC_001862, Hu. 48 AY530611, Hu 43 AY530606, Hu 44 AY530607, Hu 46 AY530609

Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29 AY530594, Hu63 AY530624, Hu64 AY530625, Hu13 AY530578, Hu56 AY530618, Hu57 AY530619, Hu49 AY530612, Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377, Clade C: Hu9 AY530629, Hu10 AY530576, Hu11 AY530577, Hu53 AY530615, Hu55 AY530617, Hu54 AY530616, Hu7 AY530628, Hu18 AY530583, Hu15 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623

Clade D: Rh62 AY530573, Rh48 AY530561, Rh54 AY530567, Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013

Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007, Bb1 AY243023, Bb2 AY243022, Rh10 AY243015, Hu17 AY530582, Hu6 AY530621, Rh25 AY530557, Pi2 AY530554, Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556

Clade F: Hu14 (AAV9) AY530579, Hu31 AY530596, Hu32 AY530597, Clonal Isolate AAV5 Y18065, AF085716, AAV 3 NC_001729, AAV 3B NC_001863, AAV4 NC_001829, Rh34 AY243001, Rh33 AY243002, Rh32 AY243003/

The skilled person can select an appropriate serotype, clade, clone or isolate of AAV for use in the present invention on the basis of their common general knowledge. It should be understood however that the invention also encompasses use of an AAV genome of other serotypes that may not yet have been identified or characterised.

The AAV genome used in the invention may be the full genome of a naturally occurring AAV virus. However, while such a vector may in principle be administered to patients, this will be done rarely in practice. The AAV genome may instead be derivatised for the purpose of administration to patients. Such derivatisation is standard in the art and the present invention encompasses the use of any known derivative of an AAV genome, and derivatives which could be generated by applying techniques known in the art. Derivatisation of the AAV genome and of the AAV capsid (discussed below) are reviewed in Coura and Nardi (*Virology Journal,* 2007, 4:99), and in Choi et al. and Wu et al., referenced above.

Derivatives of an AAV genome include any truncated or modified forms of an AAV genome which allow for expression of a mirtron from the vector in vivo in accordance with the present invention. Typically, it is possible to truncate the AAV genome significantly to include minimal viral sequence yet retain the above function. Reducing the size of the AAV genome in this way allows for increased flexibility in incorporating one or more transgenes and other sequence elements such as mirtrons or regulatory elements within the vector. It may also reduce the possibility of integration of the vector into the host cell genome, reduce the risk of recombination of the vector with wild-type virus, and avoid the triggering of a cellular immune response to viral gene proteins in the target cell.

Typically, a derivative will include at least one inverted terminal repeat sequence (ITR), or two ITRs or more. One or more of the ITRs may be derived from AAV genomes having different serotypes, or may be a chimeric or mutant ITR. An example mutant ITR is one having a deletion of a trs (terminal resolution site). This deletion allows for continued replication of the genome to generate a single-stranded genome which contains both coding and complementary sequences i.e. a self-complementary AAV genome. This allows for bypass of DNA replication in the target cell, and so enables accelerated transgene expression.

The one or more ITRs may flank a polynucleotide sequence encoding a mirtron and/or a transgene polypeptide at either end. The inclusion of one or more ITRs may aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo The ITR sequences may, for example, be those of AAV2 having, for example, the sequence of SEQ ID NOs 32 and 33 or variants thereof.

In some embodiments, ITR elements may be the only sequences retained from the native AAV genome in the derivative. Such a derivative will not include the rep and/or cap genes of the native genome or any other sequences of the native genome.

The following portions could therefore be removed in a derivative of the invention: One inverted terminal repeat (ITR) sequence, the replication (rep) and capsid (cap) genes. However, in some embodiments, derivatives may additionally include one or more rep and/or cap genes or other viral sequences of an AAV genome. Naturally occurring AAV virus integrates with a high frequency at a specific site on human chromosome 19, and shows a negligible frequency of random integration, such that retention of an integrative capacity in the vector may be tolerated in a therapeutic setting.

The derivative may be a chimeric, shuffled or capsid modified derivative. Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2, AAV5, AAV6, AAV8 or AAV9. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

AAV Capsid Coat

A vector comprising an adeno-associated virus (AAV) genome or a derivative thereof may have a capsid coat. Such an encapsidated vector may be referred to as an AAV viral particle.

The AAV vectors or particles of the invention include transcapsidated forms wherein an AAV genome or derivative having an ITR of one serotype, for example AAV2, is packaged in the capsid of a different serotype, for example AAV8. The AAV vectors or particles of the invention also include mosaic forms wherein a mixture of unmodified capsid proteins from two or more different serotypes makes up the viral coat. The coat may also comprise modified capsid proteins or variants. The invention encompasses the provision of capsid protein sequences from different serotypes, clades, clones, or isolates of AAV within the same vector or AVV viral particle, i.e. pseudotyping.

The AAV capsid may determine the tissue specificity of infection (or tropism) of an AAV virus. Accordingly, the AAV capsid serotypes for use in the invention may be those which have natural tropism for or a high efficiency of infection of the target cells, for example photoreceptor cells or RPE cells of the retina, such as AAV8. Further, one or more of the capsid proteins may be a variant of a capsid protein, such as a chimeric, shuffled, or modified variant capsid protein.

Chimeric capsid proteins include those generated by recombination between two or more capsid coding sequences of naturally occurring AAV serotypes. This may be performed for example by a marker rescue approach in which non-infectious capsid sequences of one serotype are cotransfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type. It may thereby confer improved binding to a target cell or improve targeting or the specificity of targeting of the vector to a particular target cell population, for example, photoreceptor cells or RPE cells of the retina. Alternatively the unrelated protein may be one which assists purification of the viral particle as part of the production process i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al., referenced above. The AAV vector or particle also includes chemically modified forms bearing ligands adsorbed to the capsid surface. For example, such ligands may include antibodies for targeting a particular cell surface receptor.

Relevant sections of the description relating the AAV derived vectors also apply in the case of vectors derived from other sources, such as those discussed further below.

Retrovirus Derived Vectors

The vector may comprise a retrovirus genome or a derivative thereof. Derivatives of a retrovirus genome include any truncated or modified forms of a retrovirus genome which allow for expression of a mirtron from the vector in vivo in accordance with the present invention.

As with AAV derived vectors, a retrovirus derived vector will typically comprise a derivative of a retroviral genome comprising the minimal viral sequences required for packaging and subsequent integration into a host. For retrovirus derived vectors, one or more long terminal repeats (LTRs) are the minimum element required for replication and packaging of the vectors and subsequent integration into the target cell to provide permanent transgene expression. However, other elements may also be present. For example, a human immuno deficiency virus (HIV) derived vector will typically comprises the HIV 5' LTR, which is necessary for integration into the host cell genome, the Psi signal, which is necessary for packaging of viral RNA into virions, a promoter for the transgene, and the 3' LTR. Other suitable retroviral vectors may for example be derived from murine leukemia virus (MuLV), gibbon ape leukemia virus (GaLV), Simian Immuno deficiency virus (SIV), and combinations thereof.

The tropism of a retrovirus derived vector is determined by the viral envelope proteins. Targeting of the appropriate cells, for example photoreceptor cells or RPE cells of the retina, may be enhanced by incorporating ligands for the target cells into the viral envelope.

Adenovirus Derived Vector

The vector may comprise an adenovirus genome or a derivative thereof. Derivatives of an adenovirus genome include any truncated or modified forms of an adenovirus genome which allow for expression of a mirtron from the vector in vivo in accordance with the present invention.

A large number of human adenoviral serotypes have been identified and they are categorized into six subgenera (A through F) based on nucleic acid comparisons, fibre protein characteristics, and biological properties. For example, group A includes serotypes 12 and 31, group B includes serotypes 3 and 7, group C includes serotypes 2 and 5, group D includes serotypes 8 and 30, group E includes serotype 4, and group F includes serotypes 40 and 41.

The core of an adenovirus virion contains the linear double-stranded DNA genome and associated proteins V, VII, X (mu), IVa2, and terminal protein (TP). The genome organization of different adenoviruses is conserved and has been proposed to have a timing function, wherein the ends of the genome are transcribed first (the immediate early genes E1 and E4 are located at opposite ends of the linear genome). Early transcription of E1 and E4 leads to the opening of the central region of the genome, allowing transcription of the central region.

Adenoviral genomes typically comprise eight RNA polymerase II transcriptional units: five early units, E1A, E1B, E2A-E2B, E3, and E4; two delayed early units, IX and IVa2; and the Major Late transcriptional unit. The Major Late transcriptional unit is further subdivided into L1-L5 regions based upon the use of alternative splicing sites. The transcriptional units often express proteins of similar function. For example, the E1A unit codes for two proteins responsible for activation of transcription and induction of S-phase upon cellular infection; the E1B transcription unit encodes two proteins that inhibit cellular apoptosis; the E3 transcriptional unit is involved in evasion of the immune response; and the Major Late transcriptional unit encodes structural proteins necessary for assembly of the capsid.

Heterologous mirtron and/or transgene sequences may be inserted into adenoviral genomes, for example in the early transcriptional units and in the coding regions of various structural proteins, such as hexon, penton, and fiber. Deletions may have been made in the adenoviral genome (e.g., in the E1 regions) to create replication-defective adenoviral vectors, which have generally been considered safer for administration to human subjects.

In the present invention, the adenovirus may be any adenovirus or derivative suitable for delivery of the transgene to target cells. The adenovirus may be any serotype but is typically Ad5 or Ad2. An adenovirus derived vector of the invention may comprise all or part of the genome of any adenoviral serotype, as well as combinations thereof (i.e., hybrid genomes).

The adenoviral vector used in the invention may be either replication incompetent or replication competent. Such vectors are well known. For example, in a replication incompetent vector the E1 region may be deleted and replaced with an expression cassette with an exogenous promoter driving expression of the heterologous transgene. Usually, the E3 region is also deleted. Deletion of E3 allows for larger inserts into the E1 region. Such vectors may be propagated in appropriate cell lines such as HEK 293 cells which retain and express the E1A and E1B proteins. Other vectors also lack the E4 region, and some vectors further lack the E2 region. E2 and E4 vectors must be grown on cell lines that complement the E1, E4 and E2 deletions.

Vectors may also be helper dependent vectors, which lack most or all of the adenoviral genes but retain cis-acting sequences such as the inverted terminal repeats as well as packaging sequences that are required for the genome to be packaged and replicated. These vectors are propagated in the presence of a helper adenovirus, which must be eliminated from the vector stocks. Once again, such systems are well known in the art.

The capsid is composed of seven structural proteins: II (hexon), III (penton), IIIa, IV (fiber), VI, VII, and IX. The capsid comprises 252 capsomeres, of which 240 are hexon capsomeres and 12 are penton capsomeres. Hexon capsomeres, which are trimers of the hexon protein, make up about 75% of the protein of the capsid. Penton capsomeres, which are pentamers of the penton protein, are situated at each of the 12 vertices of the virion. Each penton capsomer is bound to six adjacent hexon capsomeres and a fiber. The fiber, which is usually a trimer of the fiber protein, projects from the penton capsomer. The hexon protein and, to a lesser extent, the fiber protein comprise the main antigenic determinants of an adenovirus and also determine serotype specificity.

An adenovirus derived vector is particularly suitable for use in the invention when a transient expression of a mirtron and/or transgene is preferred.

Herpes Simplex Virus Derived Vectors

The vector may comprise an herpes simplex virus (HSV) genome or a derivative thereof. Derivatives of an HSV genome include any truncated or modified forms of a HSV genome which allow for expression of a mirtron from the vector in vivo in accordance with the present invention.

Herpes simplex virus (HSV) naturally establishes a lifelong latent infection of human peripheral sensory neurons. Recombinant HSV vectors are genetically modified to be incapable of replication, but establish a latent-like state in neurons in vitro and in vivo.

Promoters and Other Regulatory Elements

In the plasmid or vector, the nucleic acid encoding the mirtron and/or transgene is typically operably linked to a promoter. Any suitable promoter may be used as are well known in the art. The promoter may be constitutive i.e. operational in any host cell background. The promoter may for example be the ubiquitous CAG promoter. Alternatively, the promoter may be a cell-specific promoter, which drives expression a particular target cell type. For example, in some embodiments, the target cells are rod photoreceptor cells of the retina. In some cases the promoter may be human rhodopsin promoter, which may have the sequence of SEQ ID NO: 34, or a functional variant thereof. This ensures that virally delivered gene products, such as a mirtron for knocking down expression of rhodopsin and/or a replacement rhodopsin gene, are expressed only in rod photoreceptor cells.

One or more other regulatory elements, such as enhancers, postregulatory elements and polyadenylation sites may also be present in addition to the promoter. A regulatory sequence that is operably linked to the transgene and/or mirtron is any sequences that facilitates or controls expression of the transgene, for example by promoting or otherwise regulating transcription, processing, nuclear export of mRNA or stability. The term "operably linked" refers to a juxtaposition wherein the components described are in a relationship permitting them to function in their intended manner. A control sequence (e.g. a promoter) "operably linked" to a mirtron or transgene is ligated in such a way that expression of the mirtron or transgene is achieved under conditions compatible with the control sequences.

Preparation of Vector

A vector of the invention may be prepared by standard means known in the art for provision of vectors for gene therapy. Thus, well established public domain transfection, packaging and purification methods can be used to prepare a suitable vector.

Viral vectors used in gene therapy are typically generated by producing a cell line that packages a nucleic acid vector into a viral particle. The vectors typically contain the minimal viral sequences required for packaging and subsequent integration into a host, as exemplified above, other viral sequences being deleted, leaving capacity for an expression cassette for the polynucleotide(s) to be expressed, such as a mirtron or transgene. The missing viral functions are typically supplied in trans by the packaging cell line.

Packaging cells are typically used to form virus particles that are capable of infecting a host cell. The packaging cells may be any suitable cell type known in the art. The packaging cells are typically human or human derived cells. Suitable cells include Human Embryonic Kidney (HEK) 293 cells, or HEK 293 derived cell clones (for example to package adenovirus derived vectors), Hela cells (for example to package HIV or other lentivirus derived vectors) and ψ2 cells or PA317 cells (for example to package retrovirus derived vectors).

AAV derived vectors of the invention may comprise the full genome of a naturally occurring AAV virus in addition to the elements for gene therapy such as a mirtron or transgene. However, commonly a derivatised genome will be used, for instance a derivative which has at least one inverted terminal repeat sequence (ITR), but which may lack any AAV genes such as rep or cap.

In such embodiments, in order to provide for assembly of the derivatised genome into an AAV viral particle, additional genetic constructs providing AAV and/or helper virus functions will be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

AAV viruses are replication incompetent and so helper virus functions, preferably adenovirus helper functions will typically also be provided on one or more additional constructs to allow for AAV replication.

The additional constructs may be provided as plasmids or other episomal elements in the host cell, or alternatively one or more constructs may be integrated into the genome of the host cell.

Mirtron Insertion

When designing and/or cloning a plasmid or vector for expressing a mirtron it is usually beneficial to maximise the efficiency and accuracy of splicing out of the mirtron. The following may be taken into account when choosing a location for insertion of a mirtron in a plasmid, vector or transgene therein.

It is beneficial to choose a position that is rich in exonic splice enhancer motifs (ESEs) to facilitate splicing. ESE's are discussed further below. A 'MAG' (where 'M'='A' or 'C') motif at the end of the 5' exon and a 'G' at the beginning of the 3' exon are usually required for an intron to be recognised (as well as the splice donor and acceptor motifs within the intron/mirtron itself). Therefore a suitable insertion site could be identified by searching for a 'MAGG' motif in an ESE rich region of the relevant sequence such as the 5'UTR of a transgene for co-expression with the mirtron.

A mirtron may be cloned into the selected site using appropriate restriction enzymes or any other suitable alternative approach known in the art, such as overlap extension PCR. Particularly advantageous is to identify a BstB1 restriction site in a suitable region of sequence. The BstB1 restriction site is preferably followed by a 'G' residue, to provide the sequence 'TTCGAAG'. The last three bases 'AAG' provides the 'MAG' motif. The mirtron, beginning with the splice donor motif 'GT', is inserted immediately downstream.

A mirtron having appropriate "sticky ends" that complement those made by cutting the reporter gene CDS with BstB1 can be made, for example by annealing complementary oligonucleotides having sequence overhangs at the 5' and 3' ends. The forward oligonucleotide has an 5' 'CGAAG' motif compared to the sequence of the desired mirtron and correspondingly omits a 'CGAAG' motif at the 3' end. This includes the 'AG' splice acceptor motif designed to be at the 3' end of the mirtron once inserted. The reverse oligonucleotide omits a 'CTT' motif at the 5' end compared to the reverse complement of the desired mirtron, and correspondingly includes an additional 'CTT' at the 3' end. By taking this approach, the mirtrons can be inserted at the BstB1 restriction site in such a way that the gene (for example a reporter gene) is reformed when the mirtron is spliced out.

A similar approach could in principal be applied using other suitable restriction enzymes. Suitable restriction enzymes may also be used to excise a suitable fragment of a gene comprising a mirtron from a donor plasmid or vector for transfer to a new location, for example in the 5'UTR of a transgene, in a recipient plasmid or vector. In other cases a fragment may be amplified, for example by PCR amplification. Alternatively any other suitable cloning method may be used as are well known in the art.

5'UTR and Exonic Splice Enhancers (ESEs)

Exonic splice enhancers (ESEs) are certain 6 base DNA sequence motifs within an exon that are known in the art to be capable of directing or enhancing accurate and efficient splicing out of an intron. It has been suggested in the art to select an insertion site for a mirtron in the coding region of a transgene that is rich in ESE's to promote efficient splicing out of a mirtron.

According to the present invention, it is advantageous to locate a mirtron in the 5'UTR of a transgene for co-expression with the mirtron. The inventors reasoned that by placing a mirtron upstream of a transgene start codon, expression of the transgene should be less disrupted than if the mirtron is located in the CDS. There is no risk of mutant protein production (provided that no ATG motifs are introduced into the 5'UTR that could act as alternative start codons) as the transgene CDS is not interrupted. Location of the mirtron in the 5' UTR should also not increase nonsense mediated decay of the transgenic transcript, which may occur if the mirtron is located in the 3'UTR.

Furthermore, the inventors realised that by locating the mirtron in the 5'UTR it becomes unnecessary to rely upon ESEs that occur naturally in the CDS, as has been proposed previously, or that could perhaps be engineered using alternative codons into the CDS without disrupting expression of the transgene. Instead additional ESEs as described below may be introduced into the 5'UTR to promote or maintain efficient mirtron splicing. The 5'UTR of the transgene may be modified by the insertion of both a mirtron and one or more additional or exogenous sequences comprising one or more ESEs, and that are not part of the un-modified consecutive sequence of the 5'UTR. However, additional or exogenous sequences will typically not comprise any 'ATG' motifs that could act as an alternative translation start site.

The additional sequence(s) may be upstream and/or downstream of the mirtron in the modified 5'UTR. The 5'UTR and/or the additional or exogenous sequence may comprise (at least) 1, 2, 3, 4, 5, 6, 7, 8, 9, 10, 11, 12 or more ESEs. The one or more ESE(s) may be fully within 6, 7, 8, 9, 10, 11, 12, 13, 14, 15, 16, 17, 18, 19, 20, 25, 30, 35, 40, 45, 50, 55, 60, 80 or 100 nucleotides 5' of the splice donor motif or 3' of the splice acceptor motif of the mirtron. ESEs may be identified using the RESCUE-ESE online tool (http://genes.mit.edu/burgelab/rescue-ese/). An ESE may have any one of the sequences in Table 1.

TABLE 1

| ESE sequences |
| --- |

AAAACC AAGATC AGAAGA ATGCAA GAAACA GAGGAT TGAAGA

ACTGGA AAAAGA AAGATG AGAAGC ATGGAA GAAACC GATATC

TABLE 1-continued

ESE sequences

```
TGAAGC AGTGAC AAAAGC AAGCAA AGAAGG ATGGCG GAAACG

GATATG TGAAGG ATCTTC AAACAG AAGCAG AGAAGT ATTCAG

GAAACT GATCAA TGAAGT ATGAAA AAACCA AAGCCA AGAATG

ATTGGA GAAAGA GATCAT TGAGAA ATGGAT AAACCT AAGCTA

AGACAA CAAAAC GAAAGC GATGAA TGATGA ATCCTC AAACGA

AAGGAA AGACAT CAAAAG GAAATC GATGAG TGCAAC CAAACA

AAAGAA AAGGAC AGACGA CAAAGA GAACAA GATGAT TGGAAA

CAGATC AAAGAC AAGGAT AGAGAA CAACTT GAACAT GATGCA

TGGAAG CATCAG AAAGAG AATCAA AGAGAT CAAGAA GAACTG

GATGGA TGGAAT CGAATG AAAGAT AATCCA AGAGGA CAAGAT

GAACTT GATTCA TGGATC CGTCGC AAAGCA AATGAC AGATGA

CAAGTA GAAGAA GCAAAA TTCAGA CTACAT AAAGCT AATGGA

AGATGC CAATCA GAAGAC GCAAGA TTCGAA CTCCAT AAAGGA

ACAAAG AGATGT CAGAAA GAAGAG GCAGAA TTGAAG GAAAAT

AAATCC ACAACG AGCAAA CAGAAG GAAGAT GGAAAA TTGCGA

GAACCA AACAAC ACAACT AGCAGA CAGAAT GAAGCA GGAAAC

TTGGAA GCGAAT AACAAG ACAAGA AGGAAA CAGAGG GAAGGA

GGAAGA TTGGAT GGAGAT AACAGA ACAGAA AGGAAC CAGGAA

GAAGTA GGAGAA TTTGGA GTCGAC AACCAA ACCTGA AGGAAG

CCTGAA GAAGTT GGAGGA AAAAAG GTGTCG AACGAA ACGAAA

AGGACA CGAAAA GAATCA GGATCA AAACTC GTTGGA AACTGG

ACGAAG AGGAGA CGAACA GACAAA GTCAAG AACATG TATGAA

AACTTC ACGACT AGTGAA CGAAGA GACAAT GTGAAG AACCAG

TCAACG AAGAAA ACTGAA ATCAAA CGACGA GACGAA TACAAG

AACTAC TCATCA AAGAAC ACTTCA ATCAAG CGTATG GACGAC

TACAGA AAGGAG TCGTCG AAGAAG ACTTCG ATCAAT CTGAAA

GAGAAA TATGGA AATACG TCTTCA AAGAAT AGAAAA ATCAGA

CTGAAG GAGAAG TCAAGA AATCAG TGACTG AAGACA AGAAAC

ATCCAA CTTCAG GAGAGA TCAGAA AATGAA TGGAAC AAGACT

AGAAAG ATGAAG GAAAAA GAGATG TCAGGA ACATGA TGTGGA

AAGAGA AGAACA ATGAGA GAAAAC GAGGAA TGAAAC ACGCAA

AAGAGG AGAACT ATGATG GAAAAG GAGGAG TGAAAG ACTACA
```

In some cases in accordance with the present invention the one or more mirtrons may be located in the 5'UTR of a transgene for co-expression with the mirtron and flanked at the 5' and/or 3' end by a fragment of the CDS of an eGFP (enhanced green fluorescent protein) reporter gene. The eGFP CDS may have the polynucleotide sequence of SEQ ID NO: 35 or be a variant thereof, such as a variant that encodes fluorescent protein. In some case the fragment is 5' of the mirtron ends at position 346 of an eGFP sequence aligned with SEQ ID NO: 35. In some cases the fragment is 3' of the mirtron and starts at position 347 of an eGFP sequence aligned with SEQ ID NO: 35. The fragment may have at least 80%, 85%, 90%, 95%, 98% 99% or 100% sequence identity to the polynucleotide sequence of SEQ ID NO: 35 over the length of the fragment.

In 5 In some cases the fragment comprises an ESE at any or the first 1, 2, 3, 4, 5, 6, 7 or all 8 of the following positions in an eGFP sequence aligned with SEQ ID NO: 35 and/or at the following position relative to the splice donor motif of the mirtron:

positions 340-345 and/or 1 nucleotide upstream, optionally a TTCGAA motif;

positions 334-339 and/or 7 nucleotides upstream, optionally a GTCAAG motif;

positions 330-335 and/or 11 nucleotides upstream, optionally a TGAAGT motif;

positions 329-334 and/or 12 nucleotides upstream, optionally a CTGAAG motif;

positions 317-322 and/or 24 nucleotides upstream, optionally a ACAAGA motif;

positions 316-321 and/or 25 nucleotides upstream, optionally a TTCGAA motif;

positions 314-319 and/or 27 nucleotides upstream, optionally a TTCGAA motif;

positions 313-318 and/or 28 nucleotides upstream, optionally a TTCGAA motif.

In some cases the fragment comprises an ESE at any or the first 1, 2, 3, 4 or all 5 of the following positions in an eGFP sequence aligned with SEQ ID NO: 35 and/or at the following position relative to the splice acceptor motif of the mirtron:

positions 373-378 and/or 27 nucleotide downstream, optionally a CTGAAG motif;

positions 374-379 and/or 28 nucleotides downstream, optionally a TGAAGG motif;

positions 391-396 and/or 46 nucleotides downstream, optionally a AAGGAG motif;

positions 329-334 and/or 47 nucleotides downstream, optionally a GAGGAT motif;

positions 317-322 and/or 48 nucleotides downstream, optionally a GGAGGA motif.

In some cases the mirtron is flanked at the 5'end by a sequence that comprises or consists of the polynucleotide sequence of SEQ ID NO: 37 or a sequence having at least 80%, 82%, 84%, 86%, 88%, 90%, 92%, 94%, 96%, 98%, 99% or 100% sequence identity to SEQ ID NO: 37. In some cases the mirtron is flanked at the 3' end by a sequence that comprises or consists of the nucleotide sequence of SEQ ID NO: 38 or a sequence having at least 80%, 82%, 84%, 86%, 88%, 90%, 92%, 94%, 96%, 98%, 99% or 100% sequence identity to SEQ ID NO: 38.

In some cases the mirtron, or two or more mirtrons and optionally any intervening sequence between the two or more mirtrons, are embedded between positions 423 and 424 of a 5'UTR sequence aligned with the polynucleotide sequence of SEQ ID NO: 39. The 5'UTR sequence, excluding the embedded mirtron and any intervening sequences, may have at least 80%, 85%, 90%, 95%, 98% 99% or 100% sequence identity with the polynucleotide sequence of SEQ ID NO: 39. The sequence between any two mirtrons in the 5'UTR may have the polynucleotide sequence of SEQ ID NO: 40, or a polynucleotide sequence having at least 80%, 85%, 90%, 95%, 98% 99% or 100% sequence identity with the polynucleotide sequence of SEQ ID NO:40. The sequence may comprise one or more of the ESEs in the positions discussed above.

In some cases in accordance with the present invention the target gene is rhodopsin and the vector comprises the polynucleotide sequence of SEQ ID NO: 26, or a polynucleotide sequence having at least 80%, 85%, 90%, 95%, 98%, 99% or 99.5% sequence identity to a polynucleotide sequence of SEQ ID NO: 26. The sequence may comprise any suitable combination of the mirtrons and other sequence elements discussed herein. The sequence may be located in the 5'UTR of a transgene for co-expression with the mirtrons in the sequence.

The transgene may encode a "hardened" version of rhodopsin that is resistant to knock down by the mirtrons, for example any of the variant rhodopsin genes discussed herein. The 5'UTR may have the sequence of SEQ ID NO: 27, or a polynucleotide sequence having at least 80%, 85%, 90%, 95%, 98%, 99% or 99.5% sequence identity to a polynucleotide sequence of SEQ ID NO: 27 across the full sequence of the 5'UTR or the 5'UTR excluding the mirtrons of SEQ ID NOs: 12 and 14, or the 5'UTR excluding the part of the sequence consisting of the polynucleotide sequence of SEQ ID NO: 26, or a polynucleotide sequence having at least 80%, 85%, 90%, 95%, 98%, 99% or 99.5% sequence identity inserted between positions 423 and 424 of a 5'UTR sequence aligned with the polynucleotide sequence of SEQ ID NO: 39. In some cases the vector comprises the polynucleotide sequence of any one of SEQ ID NOs: 31, 64 or 65.

Homology or sequence identity as referred to anywhere herein can be measured using known methods. For example the UWGCG Package provides the BESTFIT program which can be used to calculate homology (for example used on its default settings) (Devereux et al (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (http://www.ncbi.nlm.nih.gov/).

The terms "fragment" or "fragment of the coding region of a reporter gene" as used herein refer to a string of amino acids or an amino acid sequence typically of reduced length relative to the or a reference polypeptide and comprising, over the common portion, an amino acid sequence identical to the reference polypeptide. Such a fragment according to the disclosure may be, where appropriate, included in a larger polypeptide of which it is a constituent. The fragments referred to herein may be between 5, 6, 7, 8, 9, 10, 11, 12, 13, 14, 15, 20, 25, 30, 35, 40, 41 amino acids in length and up to 41, 45, 50, 55, 60, 65, 70, 75, 80, 85, 90, 95, 100, 120, 140, 160, 180, 200, 250, 300 or more amino acids in length.

Methods of Therapy and Medical Uses

The invention concerns methods for the treatment of a retinal disease and vectors for use in such methods. The method may be a method of gene therapy. The term "gene therapy" means the therapeutic delivery of nucleic acid polymers into a patient's cells. In some cases of gene therapy, copies of one or more genes that encode a protein that is therapeutic to a subject are introduced to cells of the subject. Such a gene for introduction to the cells may be referred to herein as a transgene. In some cases the gene therapy introduces to the cells one or more genes that are normally expressed in a healthy individual but that are missing or defective in the subject. In other cases of gene therapy a nucleic acid polymer may be introduced to knock down expression of a gene in the subject, that is to reduce expression of a gene product. According to the present invention the gene therapy comprises administration of a vector that expresses a mirtron that can knock down expression of a gene that is expressed in cells of the retina. The gene that is targeted for knock down by the mirtron may be referred to herein as an endogenous gene or target gene.

The retinal disease may be any disease, condition or disorder that is caused by or exacerbated by the expression or over-expression of a gene in cells of the retina. In some cases the disease may be caused by a mutation in the gene compared to a wild-type healthy gene. The disease may be dominant genetic (or autosomal dominant) in which a mutation in one of the two copies of the gene in a subject can be sufficient for the subject to be affected by the disease or for the disease to be exacerbated. In other cases the disease may be recessive genetic (or autosomal recessive), in which a subject must have mutations in both copies of the gene to be affected or for the disease to be exacerbated. In some cases the disease is caused by or primarily caused or triggered by mutation in a single gene. In other cases the present invention may be used to treat complex genetic diseases, in which multiple genes may be involved, possibly in combination with lifestyle or environmental contributory factors.

Examples of retinal diseases that may be treated in accordance with methods of the present invention include retinitis pigmentosa, Autosomal dominant Stargardt-like macular dystrophy, autosomal dominant and autosomal recessive Best disease, Pattern dystrophy, Doyne honeycomb dystrophy, autosomal dominant drusen, progressive bifocal chorioretinal atrophy, Sorsby fundus dystrophy and age-related macular degeneration. In some cases the retinal disease is a disease, condition or disorder that is caused by or exacerbated by the expression or over-expression of a gene in photoreceptor cells or rod photoreceptor cells of the retina. In some cases the gene that is targeted for knock down by the mirtron and/or the transgene is rhodopsin. In some cases the retinal disease is dominant or recessive retinitis pigmentosa.

The subject may be a human or a non-human animal. Non-human animals include, but are not limited to, rodents (including mice and rats), and other common laboratory, domestic and agricultural animals, including rabbits, dogs, cats, horses, cows, sheep, goats, pigs, chickens, amphibians, reptiles etc.

Pharmaceutical Compositions and Modes of Administration

The one or more vectors of the invention may be formulated into pharmaceutical compositions. These compositions may comprise, in addition to the vector(s), a pharmaceutically acceptable excipient, carrier, buffer, stabiliser or other materials well known to those skilled in the art. Such materials should be non-toxic and should not interfere with the efficacy of the active ingredient. Examples of suitable compositions and methods of administration are provided in Esseku and Adeyeye (2011) and Van den Mooter G. (2006). The precise nature of the carrier or other material may be determined by the skilled person according to the route of administration. Examples of techniques and protocols can be found in Remington's Pharmaceutical Sciences, 20th Edition, 2000, pub. Lippincott, Williams & Wilkins.

The vectors of the invention may be administered by any suitable route and means that allows for transduction of the target cells. The target cells are cells of the retina, such as photoreceptor cells, rod photoreceptor cells, or RPE cells. Typically delivery is subretinal or intravitreal. The vector may be delivered surgically beneath the retina, for example by sub-retinal injection.

Dosages and dosage regimes can be determined within the normal skill of the medical practitioner responsible for administration of the composition. The dose of a vector of the invention may be determined according to various parameters, especially according to the age, weight and condition of the patient to be treated; the route of administration; and the required regimen. A physician will be able to determine the required route of administration and dosage for any particular patient.

Administration is typically in a "prophylactically effective amount" or a "therapeutically effective amount" (as the case may be, although prophylaxis may be considered therapy), this being sufficient to show benefit to the individual. For example, a therapeutically effective amount of a vector of the invention or an effective method of treatment in accordance with invention may result in reduced expression of the target gene of the mirtron and in some cases also expression of the transgene in target cells of the retina. The treatment is sufficient to result in a clinical response or to show clinical benefit to the individual, for example to cure the disease, prevent or delay onset or progression of the disease or condition or one or more symptoms, to ameliorate or alleviate one or more symptom, to induce or prolong remission, or to delay relapse or recurrence. In some cases the treatment is sufficient to improve the subject's eyesight, which may in some cases include slowing down, reducing or prevent degeneration of the subject's sight over time. More specifically the treatment may in some cases improve vision for such patients in low light conditions.

A typical single dose of the one or more vectors of the invention may between $10^8$, or $10^9$ and $10^{15}$, or $10^{14}$, or $10^{13}$, or $10^{12}$, or $10^{10}$ viral genomes (vg), or any range thereof, such as $10^9$-$10^{13}$ vg. A dose at the lower end of the range will typically be used for administration direct to the retina, whilst a dose at the higher end of the range will typically be needed for systemic administration.

A single AAV capsid that contains a single stranded DNA molecule is a single viral genome (vg). Vg can be quantified by any suitable method as well known in the art, for example real-time PCR. The one or more vectors are preferably administered only once, resulting, depending on the vector used, in permanent or transient knock down of the target gene, but repeat administrations, for example in future years and/or with different serotypes may be considered.

A composition of the invention may be administered alone or in combination with other therapeutic compositions or treatments.

EXAMPLES

Example 1—Design of Transgene Cassettes for Expressing Rhodopsin In Vivo

Figure 1:
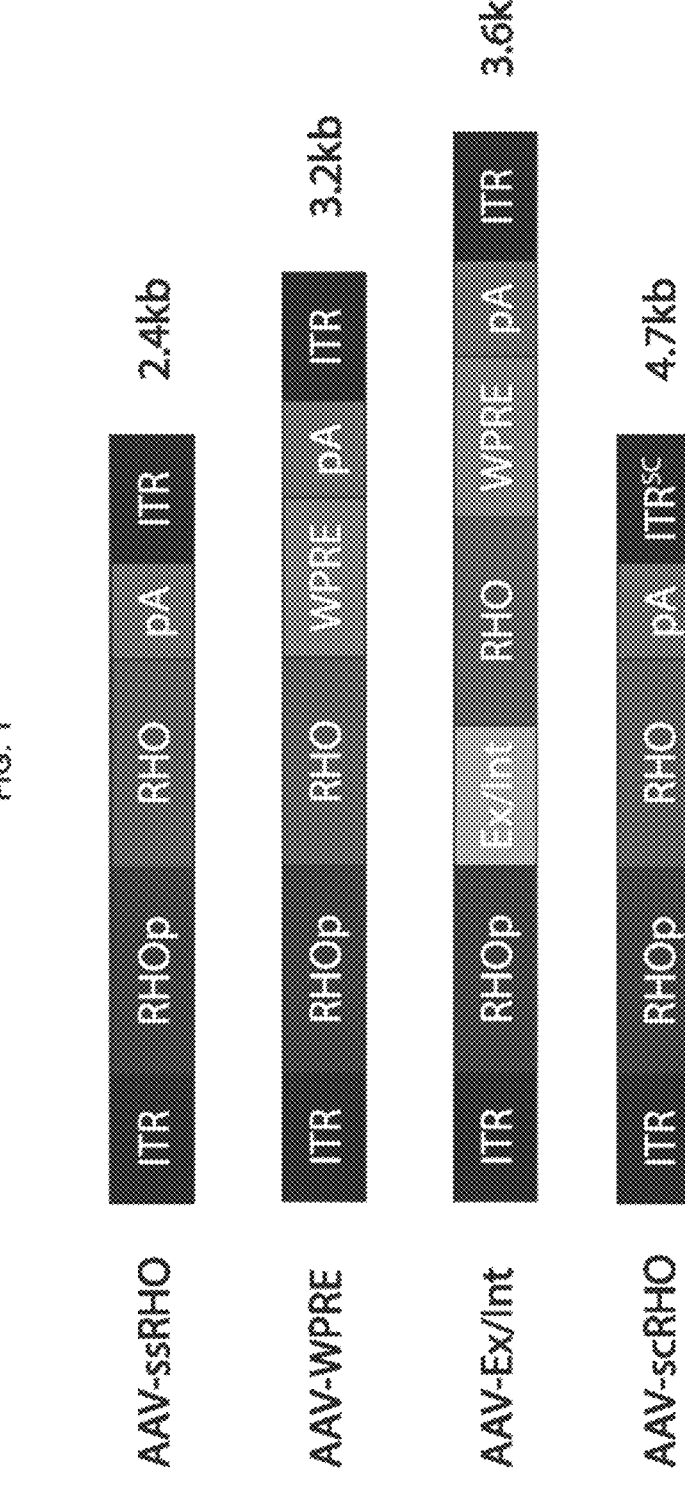
FIG. 1 Schematic of rhodopsin AAV transgenes together with effective size in kb. ITR, inverted terminal repeat; RHOp, human rhodopsin promoter; Ex/Int, first exon and intron from the chicken beta actin gene together with the splice acceptor from rabbit beta globin; RHO, human rhodopsin coding sequence; WPRE, woodchuck hepatitis virus post-transcriptional regulatory element; pA, bovine growth hormone poly-adenylation sequence; ITR$^{sc}$, mutated inverted terminal repeat (resulting in self-complementarity).

Four human rhodopsin expressing AAV2/8$^{Y733F}$ vectors were designed and manufactured (FIG. 1). All four contained the human rhodopsin cDNA sequence (RHO; SEQ ID NO: 1) downstream of the human rhodopsin promoter (RHOp; SEQ ID NO: 34):

1. AAV-ssRHO (AAV2/8$^{Y733F}$.RHOp.RHO): a single-stranded AAV genome containing the human rhodopsin CDS under the control of the human rhodopsin promoter.
2. AAV-WPRE (AAV2/8$^{Y733F}$.RHOp.RHO.WPRE): as for AAV-ssRHO but with the addition of a 3' Woodchuck Hepatitis Post-transcriptional Regulatory Element (WPRE) sequence (SEQ ID NO: 29). This sequence has been shown to improve transgene expression following retinal gene therapy in mice and humans (Patricio et al. (2017), *Mol. Ther.-Nucleic Acids* 6:198-208).

3. AAV-Ex/Int (AAV2/8$^{Y733F}$.RHOp.Ex/Int.RHO.W-PRE): as for AAV-WPRE but with the addition of the first exon and intron of the chicken beta-actin gene together with the splice acceptor from the rabbit beta-globin gene located between the RHOp sequence and Kozak consensus.
4. AAV-scRHO (scAAV2/8$^{Y733F}$.RHOp.RHO): a self-complementary (sc) version of AAV-ssRHO. Self-complementary vectors lead to increased vector efficiency as they bypass intracellular second-strand synthesis, a step that is thought to be rate-limiting in the process of AAV transduction. One major drawback of sc vectors is that they have a packaging capacity that is effectively half that of their single-stranded (ss) counterparts. This vector is very close to capacity and so self-complementarity has to be an alternative to the additional elements included in vectors 2 and 3 above.

Example 2—Ex Vivo Validation of Rhodopsin Expression Cassettes

Figure 2B:
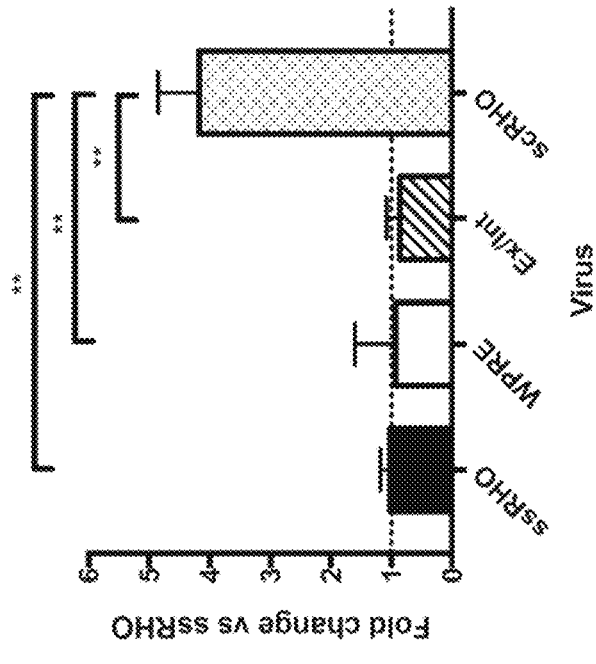
FIGS. 2A-2B Rescue of rhodopsin expression in dissociated Nrl.GFP/Rho$^{-/-}$ retinal cells following transduction with ssRHO, WPRE, Ex/Int and scRHO AAVs.
Figure 2A:
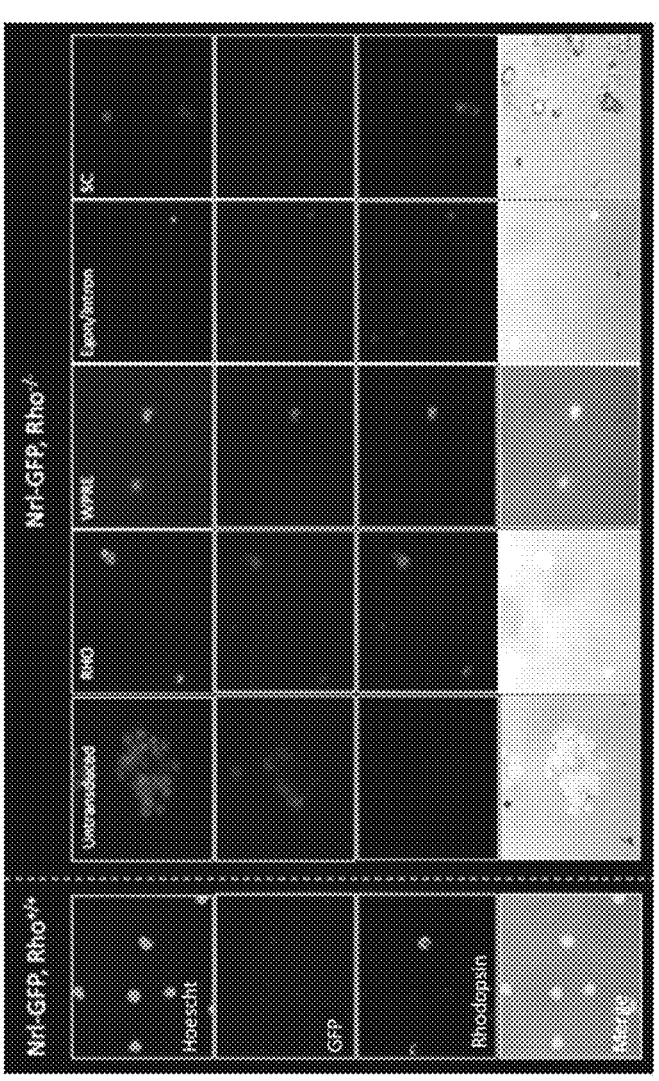

The four viruses were validated ex vivo using dissociated retinal cells from post-natal day (PND) 3 Nrl.GFP/Rho$^{-/-}$ mice. These animals carry a homozygous null mutation in rhodopsin and express GFP under the neural retina leucine zipper (Nrl) promoter. Rod cells are thus fluorescence labelled green and express no native rhodopsin. Rescue of rhodopsin expression was noted following transduction with all four viruses and immunofluorescence staining for RHO protein (FIG. 2A). RNA was also extracted from dissociated transduced PND3 retinal cells and converted to cDNA. Quantitative PCR (qPCR) analysis revealed a fourfold increase in the number of rhodopsin transcripts for AAV-scRHO transduced cells compared with those transduced with the other three viruses (FIG. 2B).

Example 3—In Vivo Validation of Rhodopsin Expression Cassettes

An in vivo comparison of the four vectors was subsequently undertaken. Subretinal injections of $2 \times 10^9$ genome copies (gc) of each virus in 1.5 μl were performed in Nrl.GFP/Rho$^{-/-}$ mice. Four weeks later, live mice were subject to spectral domain optical coherence tomography (SD-OCT) from which mean photoreceptor layer (PRL) thickness was calculated. Mice were then sacrificed and eyes extracted. Some were fixed, embedded and sectioned for immunohistochemistry, whilst others were processed for western blot analysis of rhodopsin protein levels. FIG. 3A shows retinal cryosections from such mice stained for rhodopsin. All four viruses were capable of driving human rhodopsin protein expression in the murine retina. Transduced rods elaborated outer segments packed with rhodopsin that were absent in untransduced eyes. Rhodopsin expression was confined to this layer mimicking the wild type state and confirming promoter specificity. Rhodopsin expression appeared greatest in AAV-Ex/Int and AAV-scRHO injected eyes. Analysis of SD-OCT images from injected animals confirmed that these two vectors resulted in the greatest mean photoreceptor layer (PRL) thickness (p<0.05 for each versus AAV-RHO and AAV-WPRE, one-way ANOVA Holm-Sidak multiple comparison test; FIG. 3B). Similarly, these two vectors resulted in the greatest level of rhodopsin protein expression as measured by Western blot band densitometry (FIG. 4).

Taken together, the above data suggest that the addition of WPRE and the chicken beta-actin/rabbit beta-globin exonintron-exon sequence can allow similar levels of rod-specific transgene expression to be achieved as that associated with a self-complementary vector. The advantage of the optimized single-stranded construct is that additional packaging capacity remains to allow the additional inclusion of miRNA suppression elements (such as mirtrons).

Example 4—Overexpression of Rhodopsin Alone does not Reduce Retinal Degeneration Next, it was important to establish whether overexpression of rhodopsin alone was sufficient to rescue the degenerative phenotype in a mouse model of rhodopsin dominant retinitis pigmentosa. The P23H rhodopsin knock-in mouse (Jackson laboratories) was used for this and for subsequent vector testing as this represents the most biologically relevant mouse model available. Homozygous Rho$^{P23H/P23H}$ mice were mated with homozygous Nrl.GFP mice to create offspring heterozygous for both alleles. These mice (which have rods labelled with GFP that degenerate over time) were used for all further testing and are henceforth simply referred to as 'P23H' mice.

To test whether rhodopsin overexpression was achievable, P23H mice were injected with the two most successful rhodopsin supplementation vectors developed above, AAV-scRHO and AAV-Ex/Int. Subretinal injections of $2\times10^9$ genome copies in 1.5 µl were performed in the right eyes of 3-week-old P23H mice (n=6 for each vector). Four weeks later, retinas were harvested and rhodopsin expression compared between injected right and uninjected left eyes by western blot band densitometry. This showed overexpression of rhodopsin of the order of 50% for both vectors (FIGS. 5A-5C).

Next, pilot studies were performed to establish whether rhodopsin overexpression alone was sufficient to slow retinal degeneration in P23H mice. New cohorts of P23H mice were thus injected unilaterally with either AAV-scRHO at doses of $2\times10^8$ gc ('low dose') or $2\times10^9$ ('intermediate dose') or AAV-Ex/Int at doses of $2\times10^9$ ('intermediate dose') or $2\times10^{10}$ gc ('high dose'). Electroretinography performed at one and three months post-injection showed that these treatments had no effect on the rate of retinal degeneration (FIG. 6).

Example 5—Design of Mirtrons to Knock-Down Rhodopsin Expression

Having optimized the 'replace' arm of the 'block and replace' paradigm in vivo, laboratory studies were undertaken to design and manufacture a construct capable of knocking-down rhodopsin. Seven mirtrons were designed designated M1-M7, SEQ ID NO: 10 to 16). Each mirtron was engineered to target the human and/or mouse rhodopsin genes.

Double stranded mirtrons were engineered by annealing complementary oligonucleotides. Forward oligonucleotides had the general structure 5'-P-CGAAG- (shortened mirtron sequence) where P represents a phosphate group and the shortened mirtron sequence represents that of the 76 bp mirtron design minus the 3' CGAAG motif (SEQ ID NOs: 41 to 47). Reverse oligonucleotides had the general structure 5'-P- (shortened reverse mirtron sequence)-CTT, where the shortened reverse mirtron sequence represents the reverse complement of the 76 bp mirtron sequence minus the 5' CTT motif SEQ ID NOs: 48-54). Oligonucleotides were manufactured by Sigma-Aldrich, UK and reconstituted to a concentration of 10 µM upon receipt. 10 µl forward and 10 µl reverse solution was thoroughly mixed and heated to a temperature of 95° C. using a PCR thermocycler (Multigene, Labnet International Inc.). Samples were then slowly cooled in a stepwise manner to room temperature over a period of 30 minutes to facilitate efficient annealing.

The resulting double stranded mirtron sequences (which by design already had BstB1 sticky ends) were each individually ligated into BstB1/shrimp alkaline phosphatase (both New England Biolabs, UK) treated CAG.eGFP.WPRE plasmid (FIG. 7). Correct orientation of the mirtron between nucleotides 346 and 347 of the eGFP coding region (SEQ ID NO: 35) within the construct was confirmed by commercial Sanger sequencing (Source Biosciences, UK).

Example 6—Quantification of Correct Mirtron Splicing

Each of the plasmids described in Example 5 were individually transfected into HEK293 cells. In each case, green fluorescence indicated successful and precise splicing out of the mirtron, as failure to splice would result in a frame shift of the GFP CDS downstream of the mirtron site. In this way, the degree of correct splicing for each mirtron design could be readily established in vitro and was measured using a quantitative fluorescence assay (fluorescence plate reading of GFP-mirtron transfected cell lysate normalised to that of GFP transfected cell lysate) (FIGS. 8 & 9A).

Example 7—Determination of Mirtron Splice Variants

Splice variants for GFP-mirtron constructs were also determined. RNA from GFP-mirtron transfected cells was extracted and reverse transcribed into cDNA. A set of mirtron-spanning primers directed against the flanking GFP sequence was used to amplify the spliced region. The resulting PCR products were run through a 2% agarose gel by electrophoresis. Each resulting band corresponded to a different splice product. The proportion of correctly spliced product as determined by band densitometry corresponded to that predicted by the fluorescence splice assay outlined above (FIG. 9B).

Example 8—In Vitro Determination of Mirtron-Mediated Knock Down: Target Sequence in 3'UTR Rhodopsin knockdown efficiency for all seven mirtrons was determined in vitro using the Dual Glo luciferase assay in conjunction with the PsiCHECK2 vector system (both Promega) according to manufacturer's instructions. Briefly, the PsiCHECK2 plasmid contains two luciferase genes (Renilla and Firefly) which are independently under the control of ubiquitous promoters. Each luciferase sequentially catalyses a reaction that produces light which may be quantified with a luminometer (Dual Glo assay) (FIG. 10). The Renilla luciferase has a multiple cloning site located between its stop codon and poly A sequence into which rhodopsin coding sequences were cloned. HEK293 cells were co-transfected with this vector and each GFP-mirtron plasmid. An effective mirtron would be expected to cleave its target sequence thus deadenylating the Renilla luciferase transcript and reducing the Renilla luminescent signal. Mirtrons should not however affect the Firefly signal which acts as an internal transfection control in the assay. In this way, the relative luciferase ratio (Renilla: Firefly), which is normalised to a no-mirtron GFP control reading, quantifies mirtron mediated knockdown efficiency. All seven mirtron designs were tested against PsiCHECK2 vectors for both human and mouse rhodopsin. The guide strands of mirtrons M1-4 and M6 were perfect antisense matches for both mouse and human rhodopsin mRNA. Separate human and mouse versions of mirtron 5 (designated 'M5H' and 'M5M', SEQ ID NO: 55; forward oligo: SEQ ID NO: 56; reverse oligo: SEQ ID NO: 57) were cloned which differed by 2 of the 21 guide strand nucleotides according to corresponding differences in the target nucleotide sequence of the two species. Mirtron 7 was a perfect antisense match with the human rhodopsin sequence but had a single nucleotide mismatch with the corresponding target in mouse. Results are shown in FIG. 11. Mirtrons 2, 3 and 5 induced a significant knock-down of rhodopsin of 40-70%. Note that M5H and M5M were only effective when targeting their corresponding species of rhodopsin.

Example 9—Both Splicing and a Specific Antisense Sequence are Required for Mirtron-Induced RNA Knock-Down The requirement of correct splicing and a specific antisense sequence for mirtron-mediated rhodopsin knockdown was investigated by cloning two alternative versions of Mirtron 2 (M2). The first was a so-called 'unspliceable' version (M2U, SEQ ID NO: 58; forward oligo: SEQ ID NO: 59; reverse oligo: SEQ ID NO: 60). M2 and M2U were identical in all but the first nucleotide (the 'G' at position 1 of the canonical splice donor site) which was substituted for an adenine nucleotide in M2U. The second was a 'scrambled' version (M2S, SEQ ID NO: 61; forward oligo: SEQ ID NO: 62; reverse oligo: SEQ ID NO: 63) where the nucleotides of the guide strand not predicted to be involved in splicing (positions 7-21) were randomly re-ordered. FIGS. 12A-B show that M2U did not splice out of GFP (indicated by lack of green fluorescence) and was incapable of mediating rhodopsin knock-down. Although M2S spliced out to a similar degree to M2, it too did not induce rhodopsin knockdown. Thus, both splicing and a specific antisense sequence are required for mirtron-induced RNA knockdown.

Example 10—Effect of Target Sequence Context on Mirtron Potency

To investigate the effect of target sequence context on mirtron potency, a 'short' version of the human rhodopsin target comprising the 21 bp mirtron 3 (M3) target sequence with 25 bp of upstream and downstream DNA was cloned into the multiple cloning site of the PsiCHECK2 vector. M3 efficacy against this construct was compared with that measured against the full-length sequence (FIG. 13). Interestingly, M3 was significantly more effective against the RHO target with shorter flanking sequence. Context of the target site can thus have a significant impact on the potency of mirtrons. This is likely attributable to local differences in mRNA secondary structure which may variously allow or restrict access of the RISC to the transcript target site, and may explain the differences observed between human and mouse targets for mirtrons with identical target sequences (see FIG. 11).

Example 11—In Vitro Determination of Mirtron-Mediated Knock Down: Target Sequence in Coding Region The Dual Glo luciferase assay quantifies efficacy of RNAi effectors which target the gene of interest cloned into the 3'

UTR of Renilla luciferase. It does not necessarily follow that mRNA cleavage will occur to the same extent in vivo where the target site is located within a CDS that is being actively translated. Indeed, it is thought that native miRNAs that target coding sequences may exert their effect more through translational inhibition rather than mRNA cleavage, and such miRNAs seem to have a smaller influence on target protein levels.

To investigate the efficacy of mirtrons directed against a translated sequence, the human rhodopsin gene was cloned into the PsiCHECK2 vector so as to create a RHO-Renilla luciferase fusion protein with the luciferase being tagged to the cytosolic C-terminus of rhodopsin via an APVAT link peptide (SEQ ID NO:71). The validity of this approach was first established by cloning a rhodopsin-link peptide-GFP sequence into the CAG/WPRE plasmid backbone. This was used to transfect HEK293 cells that were subsequently immunostained using the 4D2 anti-rhodopsin antibody which targets the extracellular N-terminus of the protein. Confocal fluorescence microscopy revealed the RHO-GFP fusion protein to be localised to the plasma membrane, the protein being visible as a double ring of fluorescence (FIG. 14). HEK293 cells were then transfected with the RHO-Renilla luciferase fusion PsiCHECK2 plasmid and stained for rhodopsin and luciferase. Fluorescence from the two antibodies co-localization to the plasma membrane. By contrast, staining of cells transfected with PsciCHECK2-RHO (where the human rhodopsin sequence had been cloned into the multiple cloning site of the Renilla luciferase 3' UTR) showed luciferase localization within the cytosol and no rhodopsin signal (FIG. 15).

Having confirmed that the mirtron target sequences within RHO-Luc.PsiCHECK2 are indeed translated into protein, the plasmid was used to test mirtrons 1-7 in a further Dual Glo luciferase assay. Results of this fusion assay were comparable to that of the standard assay in all cases except for that of mirtron 2 which appeared ineffective when tested using the fusion assay (FIG. 16).

This supports the hypothesis that RNAi efficacy may, for some effectors, differ when a CDS rather than a 3' UTR is targeted. This assay suggested that mirtrons 3 and 5 are likely to be the most effective of the seven candidate designs for downstream in vivo application. To our knowledge, this is the first time the Dual Luciferase assay has been applied to a fusion vector. This approach may be useful for in vitro testing of all RNA interference effectors that are designed to target coding sequences.

Example 12—BLAST Search for Off-Target Homologous Sequences

If mirtrons are to be used for the treatment of patients with retinitis pigmentosa, it is important that off-target effects within transduced rods are minimal. The data presented above for M5H and M5M would suggest that small differences in the target sequence of mirtrons may not be well tolerated.

To investigate this further, the 21 bp target sequences for the three most effective mirtrons (2, 3 and 5) were subjected to a BLAST search (www.endembl.org) for homology within the mouse and human transcriptomes. All matches with an E-value (the calculated probability of the alignment between the input and subject sequences being due to chance) of less than 10 were considered (Table 2). The longest match was an 18 bp complementary sequence (with one internal mismatch) within the GPT2 CDS (E-value=5.5). Several 14 bp alignments within the human transcriptome were also identified for mirtrons 3 and 5H which included a match between the M3 guide sequence and the 3'-UTR of the SEC14L2 gene (E-value=5.5). This potential target (along with GPT2) was explored further as nonsense mutations in SEC14L2 have been associated with a rare form of recessive retinitis pigmentosa, RP41/Stargardt disease type 4. To quantify the extent to which these predicted sequences are true off-targets for M3, the target sequence for each (along with 25 bp of upstream and downstream flanking DNA) was ligated into the multiple cloning site of the PsiCHECK2 vector. The subsequent Dual Glo assay performed against mirtron 3 suggested that mRNA levels for GPT2 and SEC14L2 are not affected by the mirtron (FIG. 17).

TABLE 2

Potential off-targets of mirtrons. A BLAST search was performed of the human and mouse transcriptomes with all targets with E-value <10 being considered)

| | Human | Match (bp) | E-value | Mouse | Match (bp) | E-value |
|---|---|---|---|---|---|---|
| Mirtron 2 | RHO | 21 | 0.0004 | Rho | 21 | 0.0002 |
| | | | | Tenm2 | 14 | 3.7 |
| Mirtron 3 | RHO | 21 | 0.0004 | Rho | 21 | 0.0002 |
| | GPT2 | 18 (1 mismatch) | 5.5 | Ctsc | 14 | 3.7 |
| | IL34 | 14 | 5.5 | Lgals4 | 14 | 3.7 |
| | PTF1A | 14 | 5.5 | Tenm2 | 14 | 3.7 |
| | SEC14L2* | 14 | 5.5 | | | |
| | GOLGA8B | 14 | 5.5 | | | |
| | AKNA | 14 | 5.5 | | | |
| | INPL1 | 14 | 5.5 | | | |
| Mirtron 5H | RHO | 21 | 0.0004 | Rho | 21 | 0.0002 |
| | ZBTB10 | 14 | 5.5 | Ptprb | 15 | 0.94 |
| | RHPT1 | 14 | 5.5 | Tgm7 | 14 | 3.7 |
| | C11orf40 | 14 | 5.5 | Mtm | 14 | 3.7 |
| | | | | Mfsd8 | 14 | 3.7 |
| | | | | Ikbkap | 14 | 3.7 |

Example 13—Insertion of Mirtrons and ESEs in the 5'UTR of a Reporter Gene

Mirtrons 2, 3 and 5 were cloned into the 5'-UTR of the CAG.GFP.WPRE plasmid. The inventors sought to promote efficient splicing of the mirtrons by also including additional sequences containing exonic splice enhancer (ESE) motifs immediately upstream and downstream of the mirtron as follows.

ESE's were identified in the sequences 5' (SEQ ID NO: 37) and 3' (SEQ ID NO: 38) of the mirtron insertion site (1 nucleotide downstream of the BstB1 restriction site) in the eGFP CDS (FIG. 18) using RESCUE-ESE (http://genes.mit-.edu/burgelab/rescue-ese/). These sequences advantageously correspond to the sequences that flank the mirtron in the reporter plasmids used to determine the accuracy and efficiency of the mirtron splicing, as described above. This simplified the process of introducing both the mirtron and additional ESE(s) into the 5'UTR, and helps to maintain the splicing accuracy and efficiency already achieved in the reporter constructs (plasmids described in Example 5). An in silico splice analysis was performed using online software (Spliceport, http://spliceport.cbcb.umd.edu) to identify the optimal 5' and 3' flank length around the mirtron insertion site (Table 3). The longest 5' and 3' flanking sequences up to but excluding the next 5' or 3' ATG motifs (which may otherwise act as cryptic translational start sites) were selected to flank the mirtrons in the new constructs. The entire sequence (5'flank-mirtron-3'flank) was amplified from the reporter constructs and cloned into a restriction site within the 5'-UTR of the transgene, at an EcoRV blunt restriction site (GAT|ATC). This is ideal for the purpose as once the construct has been inserted, the EcoRV restriction site is reformed at the 3' end. This allows multiple similar constructs (containing the same or different mirtrons) to be inserted sequentially in tandem (see Example 15 below).

Table 3-In silico splice analysis

| Upstream flank | Donor site score | Downstream flank | Acceptor site score |
|---|---|---|---|
| 0 | −1.01 | 0 | 2.41 |
| 5 | 0.8 | 5 | 3.02 |

-continued

| Upstream flank | Donor site score | Downstream flank | Acceptor site score |
|---|---|---|---|
| 10 | 0.59 | 10 | 2.65 |
| 15 | 0.4 | 15 | 2.51 |
| 20 | 1.07 | 20 | 2.32 |
| 25 | 1.21 | 25 | 2.26 |
| 30 | 0.92 | 30 | 2.1 |
| 35 | 1.56 | 35 | 2.47 |
| 41 | 1.73 | 40 | 2.27 |
| | | 45 | 2.06 |
| | | 50 | 2.35 |
| | | 53 | 2.55 |

Locating a "knock-down" mirtron in the 5'UTR of a "replacement" transgene has a number of potential advantages. Since the mirtron is upstream of the transgene start codon, expression of the transgene may be less disrupted than if the mirtron is located as an intron within the CDS. There is no risk of mutant protein production (provided that no ATG motifs are introduced into the 5'UTR that could act as alternative start codons) as the transgene CDS is not interrupted. Location of the mirtron in the 5' UTR should also not increase nonsense mediated decay of the transgenic transcript, which may occur if the mirtron is located in the 3'UTR. Furthermore, locating the mirtron in the 5'UTR allows additional sequences including ESEs to be inserted adjacent to the mirtron to promote efficient and accurate splicing out of the mirtron without disrupting expression of the transgene.

Example 14—Mirtrons in the 5'UTR are More Effective than Mirtrons in the CDS

The new constructs, known as M2-UTR, M3-UTR and M5-UTR, were compared to the mirtronless GFP plasmid for rhodopsin knockdown using the dual luciferase assay, and for downstream gene expression by the fluorescence assay as described above (FIG. 19). Mirtrons were found to be more effective when located in the 5'-UTR than when nested inside the GFP coding sequence for both human and mouse rhodopsin targets (FIG. 20). A PCR splice analysis using cDNA from transfected cells as template was performed as described above. Band densitometry performed on the subsequent gel revealed that a greater proportion of transcripts were correctly spliced for 5'UTR mirtrons when compared with that of their CDS nested counterparts (FIG. 21). Confirmation that the lowest band did indeed represent correctly spliced mRNA was achieved by Sanger sequencing of extracted DNA (FIGS. 22A-22B).

Example 15—Two Mirtrons in Tandem Knock Down Expression More Efficiently: Target Sequence in 3'UTR Having established that mirtrons remain effective when spliced out of the 5'-UTR of the supplemental transcript, the effect of multiple mirtrons in tandem within the 5'-UTR was investigated. The following plasmids were cloned:
1. M3/M3-UTR: Two copies of M3 in series, each with their own ESE flanking sequences as described above, cloned into the 5'-UTR of the CAG.GFP.WPRE plasmid.
2. M3/M5-UTR: One copy of M3 and one copy of M5 in series, each with their own ESE flanking sequences as described above, cloned into the 5'-UTR of the CAG.GFP.WPRE plasmid.

Comparison for knockdown of human and mouse rhodopsin against single 5'-UTR mirtrons using the dual luciferase assay showed superior efficacy of the tandem construct in both instances (FIG. 23). PCR splice analysis and Sanger sequencing confirmed that tandem mirtrons are independently and precisely spliced (FIGS. 24 & 25A-25B).

Example 16—Two Mirtrons in Tandem Remain Effective when the Target Sequence is in the CDS All 5'UTR mirtrons tested remained effective when directed against the RHO-Luciferase fusion protein described above (FIG. 26). Interestingly, the potency of M2-UTR was lower, and that of M3/M3-UTR was higher, in this assay than when measured using the standard dual luciferase assay.

Example 17—Two Mirtrons in Tandem Slightly Reduce Reporter Gene Expression

A fluorescence assay was performed on all 5'UTR mirtrons to elucidate their effect on downstream gene expression. FIG. 27 shows representative images of HEK293 cells transfected with these plasmids along with the results of a quantitative fluorescence assay performed on protein lysates from these cells. In summary, single 5'UTR mirtrons had no adverse effect on eventual protein levels whilst tandem mirtrons resulted in a small but significant reduction in reporter gene expression (23% and 24% reduction for M3/M3 and M3/M5 respectively).

FIG. 28 shows the knock-down effect of M3-UTR, M5H-UTR, M5M-UTR, M3/M3-UTR, M3/M5H-UTR and M3/M5M against both human and mouse rhodopsin. Although M3 alone is effective in both species, the knock-down effect is significantly greater against the mouse transcript. For this reason, the combination of M3 with M5H was chosen for the block and replace vector as this combination achieved a similar level of efficient knockdown (>75%) in both species (red arrows).

Example 18—Design of Gene for "Replacement" Rhodopsin

For an effective 'block and replace' vector, the CDS of human rhodopsin included in the AAV construct must be resistant to co-expressed mirtrons. To achieve this, codons that constitute the target sites for mirtrons 3 and 5 were changed where possible to alternative sequences that encode the same amino acids (avoiding 'rare' codons). The resulting mRNA sequence will not be complementary to these mirtrons, should not be subject to degradation, but should nonetheless result in translation of normal human rhodopsin protein.

To test this, codon-modified versions of human rhodopsin resistant to M3 (RHO$^{M3R}$), M5 (RHO$^{M5R}$) and both (RHO$^{M3/5R}$) were individually cloned into the multiple cloning site of the psiCHECK2 vector. Resistance of these transcripts to degradation by their corresponding mirtrons was then established by the Dual Glo assay (FIG. 29). The target sequences of RHO (SEQ ID NO: 1) complemented by each guide strand and the corresponding sequence in "replacement" rhodopsin genes are as follows:

```
M3 target site in RHO (nucleotides 153-173):
                                    (SEQ ID NO: 5)
CTTCCCCATCAACTTCCTCAC M3 target site in RHO^M3/5R (nucleotides 153-173):
                                    (SEQ ID NO: 24)
ATTTCCAATTAATTTTCTGAC M5 target site in RHO (nucleotides 598-618):
                                    (SEQ ID NO: 7)
ATCTACATGTTCGTGGTCCAC M5 target site in RHO^M3/5R (nucleotides 598-618):
                                    (SEQ ID NO: 25)
AATGAATCCTTCGTGATTTAT
```

Example 20—RHO$^{M3/5R}$ CDS Expresses Normally in HEK293 Cells

To confirm that the RHO$^{M3/5R}$ CDS expresses normal rhodopsin protein, the sequence was cloned into a plasmid under the control of the CAG promoter with a 3' WPRE (CAG.RHO$^{M3/5R}$.WPRE). This plasmid was then used to transfect HEK293 cells which were subsequently stained for rhodopsin by immunocytochemistry using three different antibodies. No difference in staining was observed in these cells compared to cells that had been transfected with a CAG.RHO.WPRE plasmid, and both versions trafficked to the plasma membrane (FIG. 30).

Example 21—RHO$^{M3/5R}$ CDS Expresses and Functions Normally In Vivo

To test for appropriate expression and function of RHO$^{M3/}$$_{5R}$ in vivo, 2×10⁹ gc of the vector in a total volume of 1.5 μl were injected subretinally into the right eyes of 10 Nrl.GFP/ Rho$^{-/-}$ mice. Four weeks later, dark-adapted electroretinography (ERG) was performed after which animals were sacrificed and cryosections of their eyes stained for rhodopsin by immunohistochemistry (IHC). A dark-adapted intensity-response curve (IRC) was constructed for injected right and uninjected left eyes which confirmed rescue of rod-derived responses of the electroretinogram (FIG. 31). IHC of retinal sections revealed presence of outer segments that were absent in uninjected eyes. These were packed with rhodopsin. No ectopic rhodopsin expression (i.e. outside of the outer segments) was identified in any case (FIG. 32). Thus, rhodopsin protein translated from an mRNA transcript that is resistant to both mirtrons 3 and 5 traffics to the outer segment of rods and is capable of driving the dark adapted light response.

Example 22—Design and Manufacture of Vector "AAV-M3/5.RHO"

AAV2/8$^{Y733F}$.RHOp.Ex/Int.M3/M5.RHO$^{M3/5R}$.WPRE (henceforth referred to as AAV-M3/5.RHO) (SEQ ID NO: 31) was manufactured using a transgene plasmid cloned from the elements outlined above, including:

AAV genome: The AAV genome is flanked by inverted terminal repeat (ITR) sequences derived from AAV serotype 2.

Capsid: The capsid used is derived from AAV serotype 8 which has a predilection for photoreceptors, the target cell type for this treatment. The particular variant used is the Y733F mutant which has been shown to increase gene expression following viral transduction[4,5].

RHOp: The AAV genome uses the human rhodopsin promoter. This ensures that the virally delivered gene products are expressed only in rod photoreceptor cells.

Ex/Int: The first exon and intron of the chicken beta-actin gene together with the splice acceptor from the rabbit beta-globin gene is included 3' of the RHO promoter. It was shown experimentally as discussed above that this improves downstream transgene expression whilst maintaining promoter cellular specificity.

M3/M5: Two 3' tailed mirtrons ('Mirtron 3' and 'Mirtron 5') designed to target different regions of the human rhodopsin mRNA transcript;

DNA sequences containing exonic splice enhancers (ESEs) derived from the enhanced green fluorescent protein (eGFP) gene flanking and between the two mirtrons.

Kozak consensus sequence.

RHO$^{M3/5R}$: The human rhodopsin coding sequence (CDS). The 21 base pair target regions for mirtrons 3 and 5 have been altered using alternative codons such that the transcript is resistant to mirtron-mediated knock-down but nevertheless encodes the same functional protein, as described above.

WPRE: The Woodchuck Hepatitis Post-transcriptional Regulatory Element (WPRE) is included downstream of the RHO stop codon. This sequence has been shown to improve transgene expression following retinal gene therapy in mice and humans.

bovine growth hormone poly A signal.

A schematic of AAV-M3/5.RHO is shown in FIG. 33.

Example 23—In Vivo Experimental Design

To assess efficacy of AAV-M3/5.RHO as a treatment for RP caused by rhodopsin mutations, the vector was tested in P23H mice. The vector was delivered subretinally at a 'low dose' (n=17) of $2\times10^8$ gc or a 'high dose' of $2\times10^9$ gc in 1.5 µl into the right eyes of 3-week-old mice. Left eyes were not injected and acted as internal controls. Two further groups of mice were similarly injected with vector AAV-Ex/Int (see above), which is identical to AAV-M3/5.RHO but without the mirtrons and accompanying ESE-rich flanking sequences, and without RHO codon-modification.

A separate group of P23H mice (n=12) received sham subretinal injections of the 1.5 µl phosphate buffered saline (PBS) in the right eye. Again, left eyes were not injected. In all cases, injections were delivered superiorly.

Figure 34:
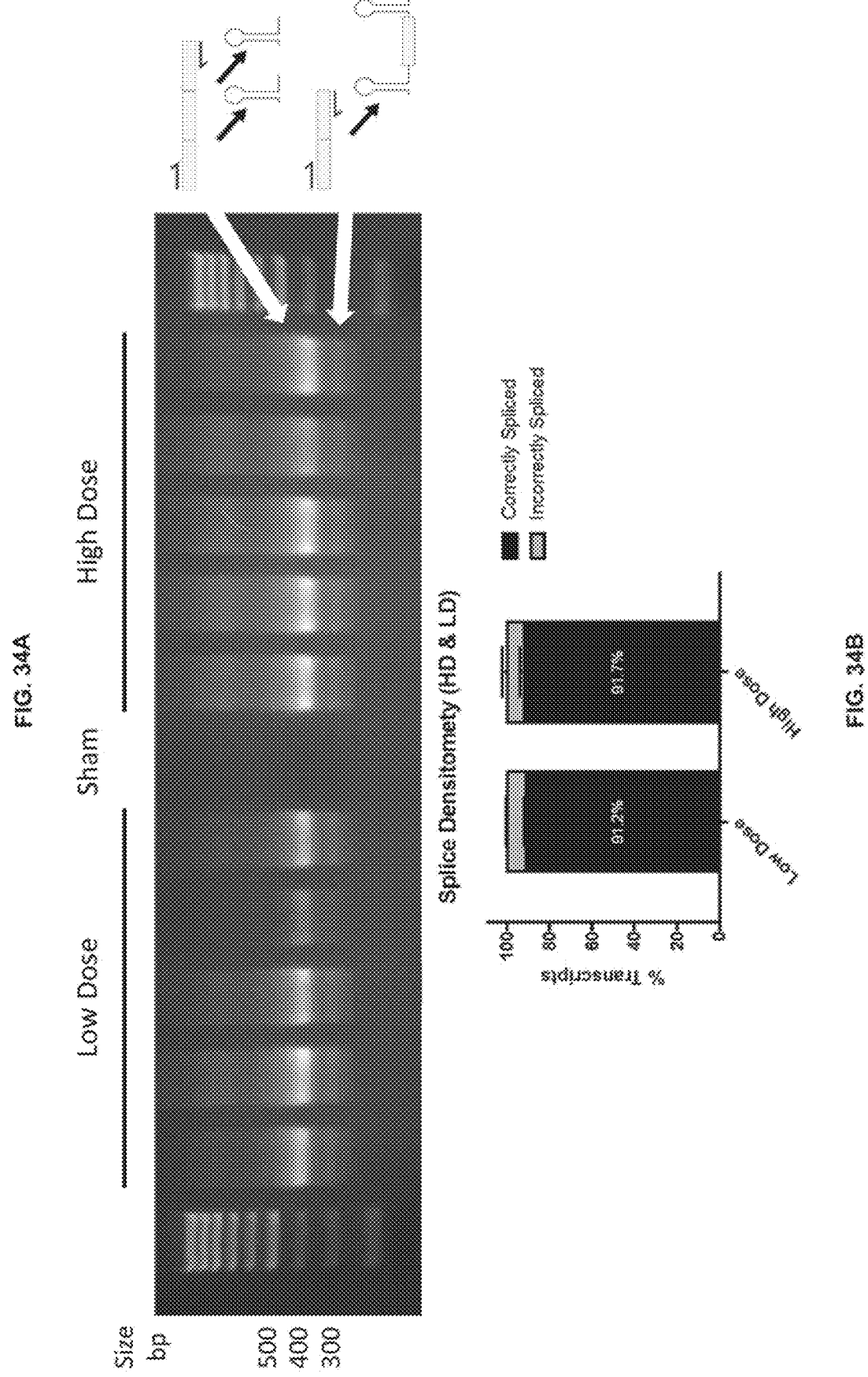

Retinae of some mice were extracted at 4 weeks post-injection for RNA extraction, cDNA synthesis and RT-qPCR (FIGS. 34 to 37). PCR splice analysis using mirtron-spanning primers and template cDNA derived from retinal lysates of injected mice showed highly efficient splicing in vivo (FIG. 34). For RT-qPCR, mouse and human rhodopsin in each eye was normalized to GFP levels (a gene only expressed in rods in P23H mice) to account for any rescue/ toxicity effects. This data demonstrates that Mirtron 3 induces knock-down of mouse rhodopsin in vivo. No significant reduction in mRho was noted at low or high dose after delivery of AAV-Ex/Int which contains no mirtrons. When the mirtron-containing vector was delivered at high dose, a 34% knockdown in total retinal mRho mRNA was evident compared with fellow sham-injected eyes P=0.0024, 2-way ANOVA Sidak's multiple comparison test. No significant knockdown was seen at low dose (FIG. 35). At low dose, RHO supplementation approximates to native levels. At high dose, a 4.6 fold increase is seen, (P=0.0011, 2-way ANOVA Sidak's multiple comparison test) suggesting a degree of overexpression (FIG. 36). Human RHO expression correlated with mRho knockdown in eyes treated with the mirtron-containing vector but not with the AAV without Mirtron 3 (FIG. 37). Together, this gene expression analysis represents the first demonstration of function of an artificial mirtron in vivo.

For the remaining mice retinal anatomy has so far been assessed by SD-OCT at 1, 2 and 3 months post-injection and retinal function has been assessed by electroretinography (ERG) at 1 month and 3 months post-injection.

Example 23—OCT Scans

Representative OCT scans from the low dose injected right and un-injected left eye of a treated P23H mouse at one month are shown in FIG. 38. Note that a thicker PRL is present in the treated eye (see arrows) which suggests a slowing of the retinal degeneration.

FIG. 39 shows photoreceptor layer (PRL) thickness of the injected eye normalised to that of its uninjected counterpart for each mouse in the AAV- and sham-injected groups. A small dip in PRL thickness can be appreciated superiorly in sham-injected animals (PRL ratio <1) as a result of surgery. In the AAV-injected group, this dip was not present and increased retinal thickness (PRL ratio>1) was evident along the horizontal meridian (p<0.0001 for both nasal and temporal retina, 2-way ANOVA, Sidak's multiple comparison test).

Further OCT analysis up to the 3 month time-point is shown in FIGS. 40 to 43.

Example 25—Dark- and Light-Adapted ERG Analysis

Figure 44:
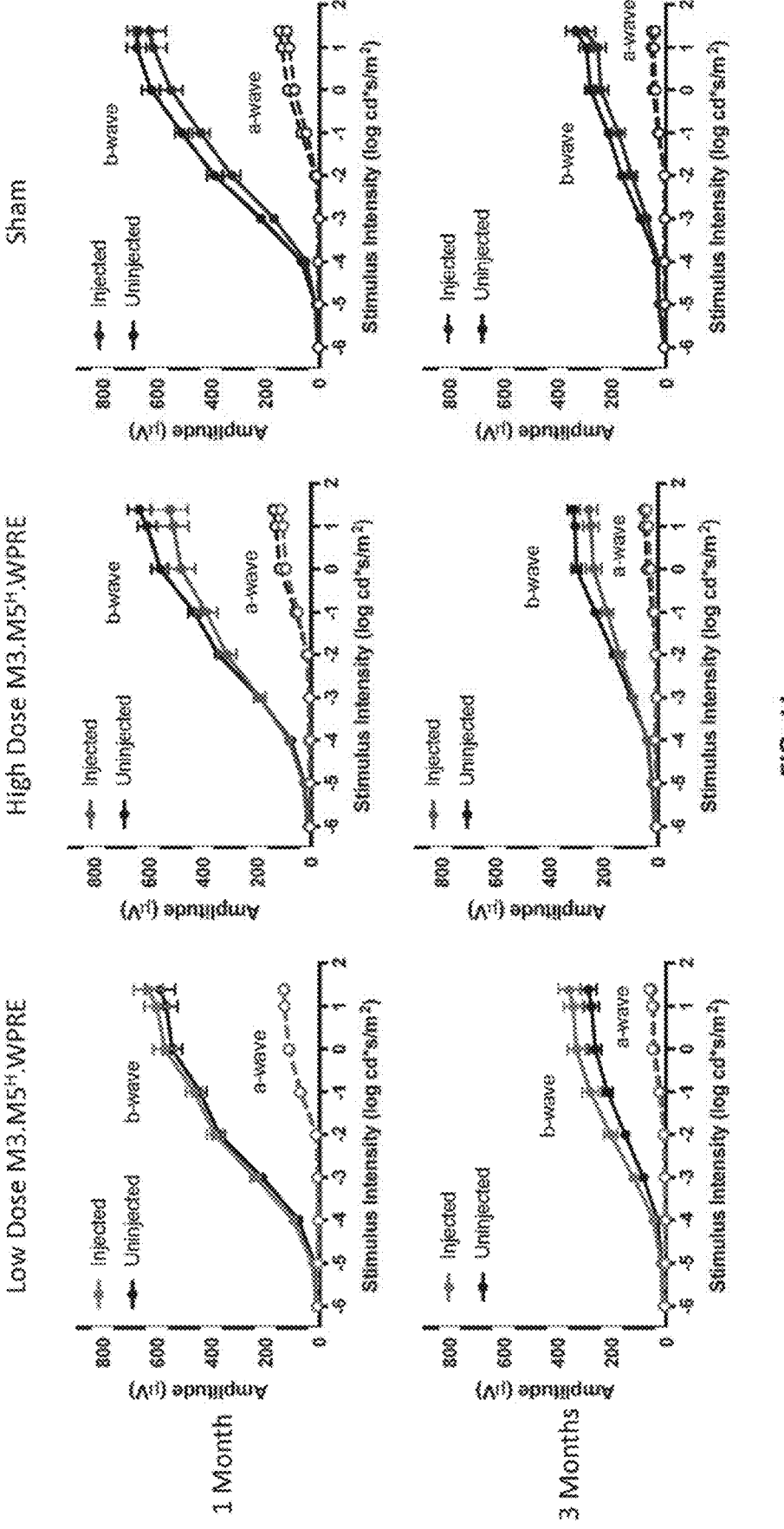

Dark- and light-adapted electroretinography analysis up to the 3 month time-point is shown in FIGS. 44 to 46.

Example 26—Design and Manufacture of New
Vectors without WPRE

The Examples above demonstrate that a benefit of AAV-M3/5$^H$ in P23H mice is achieved using the low dose but some toxicity was apparent at high dose. Given that the mRNA analysis showed very high expression levels of RHO (see FIG. 36) and overexpression of this protein in known to be toxic to photoreceptors, it is likely that this is the cause. Mirtron expression is unlikely to be the cause as this toxicity was also seen with the mirtronless vector.

Two vectors were manufactured without the WPRE which should reduce RHO expression to more physiological levels. Schematic of the two vectors are shown in FIG. 47. Vector AAV2/8$^{Y733F}$.RHOp.Ex/Int.M3/M5H.RHO$^{M3/5R}$ ("AAV-M3/5H") contains the same two mirtrons as AAV2/8$^{Y733F}$.RHOp.Ex/Int.M3/M5.RHO$^{M3/5R}$, WPRE (AAV-M3/5.RHO), whereas AAV2/8$^{Y733F}$.RHOp.Ex/Int.M3/M5M.RHO$^{M3/5R}$ ("AAV-M3/5M") replaces the mirtron 5 directed against human RHO with the mirtron 5 directed against mouse RHO. This will make it possible to assess the difference between having one or two active mirtrons in vivo.

---

The invention claimed is:

1. A method of treating a retinitis pigmentosa in a subject in need thereof, the method comprising administering to the subject a vector that comprises a mirtron for knocking down expression of rhodopsin expressed in the retina, and wherein a guide strand of the mirtron complements a rhodopsin nucleotide sequence selected from SEQ ID NO: 5 or SEQ ID NO: 7 or a nucleotide sequence having at least 80% sequence identity to SEQ ID NO: 5 or SEQ ID NO: 7.

2. The method according to claim 1, wherein the vector further comprises a transgene for expression of rhodopsin, wherein the rhodopsin transgene is resistant to knock-down by the mirtron.

3. The method according to claim 2, wherein
the mirtron is located in the 5'UTR of the rhodopsin transgene.

4. The method according to claim 2, wherein the mirtron guide strand complements the sequence of SEQ ID NO: 5 and the transgene for expression of rhodopsin comprises the nucleotide sequence of SEQ ID NO: 24, and/or the mirtron guide strand complements the sequence of SEQ ID NO: 7 and the transgene for expression of rhodopsin comprises the nucleotide sequence of SEQ ID NO: 25.

5. The method according to claim 1, wherein
(i) the mirtron is embedded in a fragment of a polynucleotide sequence that encodes eGFP between positions 346 and 347 of an eGFP coding sequence aligned with SEQ ID NO: 35; or (ii) the mirtron is flanked upstream by the nucleotide sequence of SEQ ID NO: 37 or a nucleotide sequence having at least 80% homology to SEQ ID NO: 37 or is flanked downstream by the nucleotide sequence of SEQ ID NO: 38 or a nucleotide sequence having at least 80% homology to SEQ ID NO: 38.

6. The method according to claim 1, wherein the vector comprises two or more mirtrons for knocking down expression of rhodopsin.

7. The method according to claim 6, wherein
one of the mirtron guide strands complements a rhodopsin nucleotide sequence selected from SEQ ID NO: 5 and a nucleotide sequence having at least 80% sequence identity to SEQ ID NO: 5, and the other mirtron guide strand complements a rhodopsin nucleotide sequence selected from SEQ ID NO: 7 and a nucleotide sequence having at least 80% sequence identity to SEQ ID NO: 7.

8. The method according to claim 1 wherein
(i) the vector comprises the nucleotide sequence of SEQ ID NO: 26 or a nucleotide sequence having at least 80% sequence identity to SEQ ID NO: 26; or (ii) the vector comprising the nucleotide sequence of SEQ ID NO: 31, SEQ ID NO: 64 or SEQ ID NO: 65.

* * * * *

SEQUENCE LISTING

```
<160> NUMBER OF SEQ ID NOS: 71

<210> SEQ ID NO 1
<211> LENGTH: 1047
<212> TYPE: DNA
<213> ORGANISM: Homo sapiens

<400> SEQUENCE: 1
atgaatggca cagaaggccc taacttctac gtgcccttct ccaatgcgac gggtgtggta      60
cgcagcccct tcgagtaccc acagtactac ctggctgagc catggcagtt ctccatgctg     120
gccgcctaca tgtttctgct gatcgtgctg ggcttcccca tcaacttcct cacgctctac     180
gtcaccgtcc agcacaagaa gctgcgcacg cctctcaact acatcctgct caacctagcc     240
gtggctgacc tcttcatggt cctaggtggc ttcaccagca ccctctacac ctctctgcat     300
ggatacttcg tcttcgggcc cacaggatgc aatttggagg gcttctttgc caccctgggc     360
ggtgaaattg ccctgtggtc cttggtggtc ctggccatcg agcggtacgt ggtggtgtgt     420
aagcccatga gcaacttccg cttcggggag aaccatgcca tcatgggcgt tgccttcacc     480
tgggtcatgg cgctggcctg cgccgcaccc ccactcgccg gctggtccag gtacatcccc     540
gagggcctgc agtgctcgtg tggaatcgac tactacacgc tcaagccgga ggtcaacaac     600
gagtcttttg tcatctacat gttcgtggtc cacttcacca tccccatgat tatcatcttt     660
ttctgctatg ggcagctcgt cttcaccgtc aaggaggccg ctgcccagca gcaggagtca     720
gccaccacac agaaggcaga gaaggaggtc acccgcatgg tcatcatcat ggtcatcgct     780
ttcctgatct gctgggtgcc ctacgccagc gtggcattct acatcttcac ccaccaggGc     840
tccaacttcg gtcccatctt catgaccatc ccagcgttct ttgccaagag cgccgccatc     900
tacaaccctg tcatctatat catgatgaac aagcagttcc ggaactgcat gctcaccacc     960
atctgctgcg gcaagaaccc actgggtgac gatgaggcct ctgctaccgt gtccaagacg    1020
gagacgagcc aggtggcccc ggcctaa                                        1047
```

```
<210> SEQ ID NO 2
<211> LENGTH: 348
<212> TYPE: PRT
<213> ORGANISM: Homo sapiens

<400> SEQUENCE: 2

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45
```

-continued

```
Val Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
                100                 105                 110

Glu Gly Phe Phe Ala Thr Leu Gly Gly Glu Ile Ala Leu Trp Ser Leu
                115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
                180                 185                 190

Thr Leu Lys Pro Glu Val Asn Asn Glu Ser Phe Val Ile Tyr Met Phe
                195                 200                 205

Val Val His Phe Thr Ile Pro Met Ile Ile Ile Phe Phe Cys Tyr Gly
    210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Val Pro Tyr Ala Ser Val Ala
                260                 265                 270

Phe Tyr Ile Phe Thr His Gln Gly Ser Asn Phe Gly Pro Ile Phe Met
                275                 280                 285

Thr Ile Pro Ala Phe Phe Ala Lys Ser Ala Ala Ile Tyr Asn Pro Val
    290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
                340                 345
```

```
<210> SEQ ID NO 3
<211> LENGTH: 21
<212> TYPE: DNA
<213> ORGANISM: Artificial Sequence
<220> FEATURE:
<223> OTHER INFORMATION: Target sequence of mirtron 1

<400> SEQUENCE: 3
atctacatgt tcgtggtcca c                                                 21

<210> SEQ ID NO 4
<211> LENGTH: 21
<212> TYPE: DNA
<213> ORGANISM: Artificial Sequence
<220> FEATURE:
<223> OTHER INFORMATION: Target sequence of mirtron 2

<400> SEQUENCE: 4
```
atcaacttcc tcacgctcta c                                    21

<210> SEQ ID NO 5
<211> LENGTH: 21
<212> TYPE: DNA
<213> ORGANISM: Artificial Sequence
<220> FEATURE:
<223> OTHER INFORMATION: Target sequence of mirtron 3

<400> SEQUENCE: 5
cttccccatc aacttcctca c                                    21

<210> SEQ ID NO 6
<211> LENGTH: 21
<212> TYPE: DNA
<213> ORGANISM: Artificial Sequence
<220> FEATURE:
<223> OTHER INFORMATION: Target sequence of mirtron 4

<400> SEQUENCE: 6
cttcctcacg ctctacgtca c                                    21

<210> SEQ ID NO 7
<211> LENGTH: 21
<212> TYPE: DNA
<213> ORGANISM: Artificial Sequence
<220> FEATURE:
<223> OTHER INFORMATION: Target sequence of mirtron 5H

<400> SEQUENCE: 7
aacgagtctt ttgtcatcta c                                    21

<210> SEQ ID NO 8
<211> LENGTH: 21
<212> TYPE: DNA
<213> ORGANISM: Artificial Sequence
<220> FEATURE:
<223> OTHER INFORMATION: Target sequence of mirtron 6

<400> SEQUENCE: 8
catgttcgtg gtccacttca c                                    21

<210> SEQ ID NO 9
<211> LENGTH: 21
<212> TYPE: DNA
<213> ORGANISM: Artificial Sequence
<220> FEATURE:
<223> OTHER INFORMATION: Target sequence of mirtron 7

<400> SEQUENCE: 9
gttccggaac tgcatgctca c                                    21

<210> SEQ ID NO 10
<211> LENGTH: 76
<212> TYPE: DNA
<213> ORGANISM: Artificial Sequence
<220> FEATURE:
<223> OTHER INFORMATION: Mirtron 1

<400> SEQUENCE: 10
gtggaccacg aacatgtaga tttcaagaga atctacatgt cgtggtccc tcagtttttt     60 ctctttcttt tcgaag                                          76

<210> SEQ ID NO 11
<211> LENGTH: 76

```
<212> TYPE: DNA
<213> ORGANISM: Artificial Sequence
<220> FEATURE:
<223> OTHER INFORMATION: Mirtron 2

<400> SEQUENCE: 11
gtagagcgtg aggaagttga tttcaagaga atcaacttcc tcacgctttc tcagtttttt      60
ctctttcttt tcgaag                                                       76

<210> SEQ ID NO 12
<211> LENGTH: 76
<212> TYPE: DNA
<213> ORGANISM: Artificial Sequence
<220> FEATURE:
<223> OTHER INFORMATION: Mirtron 3

<400> SEQUENCE: 12
gtgaggaagt tgatggggaa gttcaagaga cttccccatc aacttctttc tcagtttttt      60
ctctttcttt tcgaag                                                       76

<210> SEQ ID NO 13
<211> LENGTH: 76
<212> TYPE: DNA
<213> ORGANISM: Artificial Sequence
<220> FEATURE:
<223> OTHER INFORMATION: Mirtron 4

<400> SEQUENCE: 13
gtgacgtaga gcgtgaggaa gttcaagaga cttcctcacg ctctacgttc tcagtttttt      60
ctctttcttt tcgaag                                                       76

<210> SEQ ID NO 14
<211> LENGTH: 76
<212> TYPE: DNA
<213> ORGANISM: Artificial Sequence
<220> FEATURE:
<223> OTHER INFORMATION: Mirtron 5H

<400> SEQUENCE: 14
gtagatgaca aaagactcgt tttcaagaga aacgagtctt ttgtcatttc tcagtttttt      60
ctctttcttt tcgaag                                                       76

<210> SEQ ID NO 15
<211> LENGTH: 76
<212> TYPE: DNA
<213> ORGANISM: Artificial Sequence
<220> FEATURE:
<223> OTHER INFORMATION: Mirtron 6

<400> SEQUENCE: 15
gtgaagtgga ccacgaacat gttcaagaga catgttcgtg gtccactttc tcagtttttt      60
ctctttcttt tcgaag                                                       76

<210> SEQ ID NO 16
<211> LENGTH: 76
<212> TYPE: DNA
<213> ORGANISM: Artificial Sequence
<220> FEATURE:
<223> OTHER INFORMATION: Mirtron 7

<400> SEQUENCE: 16
gtgagcatgc agttccggaa cttcaagaga gttccggaac tgcatgtttc tcagtttttt      60
```

-continued

```
ctctttcttt tcgaag                                                 76

<210> SEQ ID NO 17
<211> LENGTH: 21
<212> TYPE: DNA
<213> ORGANISM: Artificial Sequence
<220> FEATURE:
<223> OTHER INFORMATION: Guide strand sequence of mirtron 1

<400> SEQUENCE: 17
gtggaccacg aacatgtaga t                                           21

<210> SEQ ID NO 18
<211> LENGTH: 21
<212> TYPE: DNA
<213> ORGANISM: Artificial Sequence
<220> FEATURE:
<223> OTHER INFORMATION: Guide strand sequence of mirtron 2

<400> SEQUENCE: 18
gtagagcgtg aggaagttga t                                           21

<210> SEQ ID NO 19
<211> LENGTH: 21
<212> TYPE: DNA
<213> ORGANISM: Artificial Sequence
<220> FEATURE:
<223> OTHER INFORMATION: Guide strand sequence of mirtron 3

<400> SEQUENCE: 19
gtgaggaagt tgatggggaa g                                           21

<210> SEQ ID NO 20
<211> LENGTH: 21
<212> TYPE: DNA
<213> ORGANISM: Artificial Sequence
<220> FEATURE:
<223> OTHER INFORMATION: Guide strand sequence of mirtron 4

<400> SEQUENCE: 20
gtgacgtaga gcgtgaggaa g                                           21

<210> SEQ ID NO 21
<211> LENGTH: 21
<212> TYPE: DNA
<213> ORGANISM: Artificial Sequence
<220> FEATURE:
<223> OTHER INFORMATION: Guide strand sequence of mirtron 5

<400> SEQUENCE: 21
gtagatgaca aaagactcgt t                                           21

<210> SEQ ID NO 22
<211> LENGTH: 21
<212> TYPE: DNA
<213> ORGANISM: Artificial Sequence
<220> FEATURE:
<223> OTHER INFORMATION: Guide strand sequence of mirtron 6

<400> SEQUENCE: 22
gtgaagtgga ccacgaacat g                                           21

<210> SEQ ID NO 23
<211> LENGTH: 21
<212> TYPE: DNA
<213> ORGANISM: Artificial Sequence
```

<220> FEATURE:
<223> OTHER INFORMATION: Guide strand sequence of mirtron 7

<400> SEQUENCE: 23
gtgagcatgc agttccggaa c                                                              21

<210> SEQ ID NO 24
<211> LENGTH: 21
<212> TYPE: DNA
<213> ORGANISM: Artificial Sequence
<220> FEATURE:
<223> OTHER INFORMATION: Modified target sequence of mirtron 3

<400> SEQUENCE: 24
atttccaatt aattttctga c                                                              21

<210> SEQ ID NO 25
<211> LENGTH: 21
<212> TYPE: DNA
<213> ORGANISM: Artificial Sequence
<220> FEATURE:
<223> OTHER INFORMATION: Modified target sequence of mirtron 5H

<400> SEQUENCE: 25
aatgaatcct tcgtgattta t                                                              21

<210> SEQ ID NO 26
<211> LENGTH: 340
<212> TYPE: DNA
<213> ORGANISM: Artificial Sequence
<220> FEATURE:
<223> OTHER INFORMATION: 5'UTR insert (eGFP - M3 - eGFP - M5 - eGFP)

<400> SEQUENCE: 26
tgacgggaac tacaagaccc gcgctgaagt caagttcgaa ggtgaggaag ttgatgggga         60
agttcaagag acttccccat caacttcttt ctcagttttt tctctttctt ttcgaaggtg        120
acaccctggt gaatagaatc gagctgaagg gcattgactt taaggaggat tgacgggaac        180
tacaagaccc gcgctgaagt caagttcgaa ggtagatgac aaaagactcg ttttcaagag        240
aaacgagtct tttgtcattt ctcagttttt tctctttctt ttcgaaggtg acaccctggt        300
gaatagaatc gagctgaagg gcattgactt taaggaggat                              340

<210> SEQ ID NO 27
<211> LENGTH: 779
<212> TYPE: DNA
<213> ORGANISM: Artificial Sequence
<220> FEATURE:
<223> OTHER INFORMATION: 5'UTR with mirtrons and additional ESE-rich
      sequences

<400> SEQUENCE: 27
ggagtcgctg cgcgctgcct tcgccccgtg ccccgctccg ccgccgcctc gcgccgcccg         60
ccccggctct gactgaccgc gttactccca caggtgagcg ggcgggacgg cccttctcct        120
ccgggctgta attagcgctt ggtttaatga cggcttgttt cttttctgtg gctgcgtgaa        180
agccttgagg ggctccggga gggccctttg tgcgggggga gcggctcggg gctgtccgcg        240
gggggacggc tgccttcggg gggacgggg  cagggcgggg ttcggcttct ggcgtgtgac        300
cggcggctct agagcctctg ctaaccatgt tcatgccttc ttcttttttcc tacagctcct        360 gggcaacgtg ctggttattg tgctgtctca tcattttggc aaagaattgg atcctagctt        420
gattgacggg aactacaaga cccgcgctga agtcaagttc gaaggtgagg aagttgatgg        480

-continued

```
ggaagttcaa gagacttccc catcaacttc tttctcagtt ttttctcttt cttttcgaag     540
gtgacaccct ggtgaataga atcgagctga agggcattga ctttaaggag gattgacggg     600
aactacaaga cccgcgctga agtcaagttc gaaggtagat gacaaaagac tcgtttttcaa     660 gagaaacgag tcttttgtca tttctcagtt ttttctcttt cttttcgaag gtgacaccct     720
ggtgaataga atcgagctga agggcattga ctttaaggag gatatcgaat ccgccacc      779
```

```
<210> SEQ ID NO 28
<211> LENGTH: 3947
<212> TYPE: DNA
<213> ORGANISM: Artificial Sequence
<220> FEATURE:
<223> OTHER INFORMATION: AAV sequence

<400> SEQUENCE: 28
```

```
cacatacgat ttaggtgaca ctatagaata cacggaatta attctagctg cgcgctcgct      60
cgctcactga ggccgcccgg gcaaagcccg ggcgtcgggc gacctttggt cgcccggcct     120
cagtgagcga gcgagcgcgc agagagggag tggccaactc catcactagg ggttccttgt     180
agttaatgat taacccgcca tgctacttat ctacgtagcc atgctctagg tacccagatc     240
ttccccacct agccacctgg caaactgctc cttctctcaa aggcccaaac atggcctccc     300
agactgcaac ccccaggcag tcaggccctg tctccacaac ctcacagcca ccctggacgg     360
aatctgcttc ttcccacatt tgagtcctcc tcagccctg agctcctctg ggcagggctg     420
tttctttcca tctttgtatt cccaggggc tgcaaataaa tgtttaatga acgaacaaga     480
gagtgaattc caattccatg caacaaggat tgggctcctg ggccctaggc tatgtgtctg     540
gcaccagaaa cggaagctgc aggttgcagc ccctgccctc atggagctcc tcctgtcaga     600
ggagtgtggg gactggatga ctccagaggt aacttgtggg ggaacgaaca ggtaaggggc     660
tgtgtgacga gatgagagac tgggagaata aaccagaaag tctctagctg tccagaggac     720
atagcacaga ggcccatggt ccctatttca aacccaggcc accagactga gctgggacct     780
tgggacagac aagtcatgca gaagttaggg gaccttctcc tccctttttcc tggatcctga     840 gtacctctcc tccctgacct caggcttcct cctagtgtca ccttggcccc tcttagaagc     900
caattaggcc ctcagtttct gcagcgggga ttaatatgat tatgaacacc cccaatctcc     960
cagatgctga ttcagccagg agcttaggag ggggaggtca ctttataagg gtctgggggg    1020
gtcagaaccc agagtcatcc ggagtcgctg cgcgctgcct tcgccccgtg ccccgctccg    1080
ccgccgcctc gcgccgcccg ccccggctct gactgaccgc gttactccca caggtgagcg    1140
ggcgggacgg cccttctcct ccgggctgta attagcgctt ggtttaatga cggcttgttt    1200
cttttctgtg gctgcgtgaa agccttgagg ggctccggga gggccctttg tgcgggggga    1260
gcggctcggg gctgtccgcg ggggacggc tgccttcggg ggggacgggg cagggcgggg    1320
ttcggcttct ggcgtgtgac cggcggctct agagcctctg ctaaccatgt tcatgccttc    1380
ttctttttcc tacagctcct gggcaacgtg ctggttattg tgctgtctca tcattttggc    1440
aaagaattgg atcctagctt gattgacggg aactacaaga cccgcgctga agtcaagttc    1500 gaaggtgagaa aagttgatgg ggaagttcaa gagacttccc catcaacttc tttctcagtt    1560
ttttctcttt cttttcgaag gtgacaccct ggtgaataga atcgagctga agggcattga    1620
ctttaaggag gattgacggg aactacaaga cccgcgctga agtcaagttc gaaggtagat    1680
gacaaaagac tcgtttttcaa gagaaacgag tcttttgtca tttctcagtt ttttctcttt    1740
```

```
cttttcgaag gtgacaccct ggtgaataga atcgagctga agggcattga ctttaaggag     1800
gatatcgaat tccgccacca tgaatggcac agaaggccct aacttctacg tgcccttctc     1860
caatgcgacg ggtgtggtac gcagcccctt cgagtaccca cagtactacc tggctgagcc     1920
atggcagttc tccatgctgg ccgcctacat gtttctgctg atcgtgctgg gatttccaat     1980
taattttctg acgctctacg tcaccgtcca gcacaagaag ctgcgcacgc ctctcaacta     2040
catcctgctc aacctagccg tggctgacct cttcatggtc ctaggtggct tcaccagcac     2100
cctctacacc tctctgcatg gatacttcgt cttcgggccc acaggatgca atttggaggg     2160 cttcttttgcc accctgggcg gtgaaattgc cctgtggtcc ttggtggtcc tggccatcga     2220
gcggtacgtg gtggtgtgta gcccatgag caacttccgc ttcggggaga accatgccat     2280
catgggcgtt gccttcacct gggtcatggc gctggcctgc gccgcacccc cactcgccgg     2340
ctggtccagg tacatccccg agggcctgca gtgctcgtgt ggaatcgact actacacgct     2400
caagccggag gtcaacaatg aatccttcgt gatttatatg ttcgtggtcc acttcaccat     2460
ccccatgatt atcatctttt tctgctatgg gcagctcgtc ttcaccgtca aggaggccgc     2520
tgcccagcag caggagtcag ccaccacaca gaaggcagag aaggaggtca cccgcatggt     2580
catcatcatg gtcatcgctt tcctgatctg ctgggtgccc tacgccagcg tggcattcta     2640
catcttcacc caccagggct ccaacttcgg tcccatcttc atgaccatcc cagcgttctt     2700
tgccaagagc gccgccatct acaaccctgt catctatatc atgatgaaca gcagttccg     2760 gaactgcatg ctcaccacca tctgctgcgg caagaaccca ctgggtgacg atgaggcctc     2820
tgctaccgtg tccaagacgg agacgagcca ggtggccccg gcctaaaagc ttatcgataa     2880
tcaacctctg gattacaaaa tttgtgaaag attgactggt attcttaact atgttgctcc     2940
ttttacgcta tgtggatacg ctgctttaat gcctttgtat catgctattg cttcccgtat     3000
ggctttcatt ttctcctcct tgtataaatc ctggttgctg tctctttatg aggagttgtg     3060
gcccgttgtc aggcaacgtg gcgtggtgtg cactgtgttt gctgacgcaa cccccactgg     3120
ttggggcatt gccaccacct gtcagctcct ttccgggact ttcgctttcc cctccctat     3180 tgccacggcg gaactcatcg ccgcctgcct tgcccgctgc tggacagggg ctcggctgtt     3240
gggcactgac aattccgtgg tgttgtcggg gaaatcatcg tcctttcctt ggctgctcgc     3300
ctgtgttgcc acctggattc tgcgcgggac gtccttctgc tacgtccctt cggccctcaa     3360
tccagcggac cttccttccc gcggcctgct gccggctctg cggcctcttc cgcgtcttcg     3420
ccttcgccct cagacgagtc ggatctccct ttgggccgcc tccccgcatc gataccgtcg     3480
actcgctgat cagcctcgac tgtgccttct agttgccagc catctgttgt ttgcccctcc     3540
cccgtgcctt ccttgaccct ggaaggtgcc actcccactg tcctttccta ataaaatgag     3600
gaaattgcat cgcattgtct gagtaggtgt cattctattc tggggggtgg ggtggggcag     3660
gacagcaagg gggaggattg ggaagacaat agcaggcatg ctggggatgc ggtgggctct     3720
atggcttctg aggcggaaag aaccagctgg ggctcgacta gagcatggct acgtagataa     3780
gtagcatggc gggttaatca ttaactacaa ggaacccta gtgatggagt tggccactcc     3840
ctctctgcgc gctcgctcgc tcactgaggc cgggcgacca aaggtcgccc gacgcccggg     3900
cggcctcagt gagcgagcga gcgcgcagag cttttttgcaa aagccta              3947
```

<210> SEQ ID NO 29
<211> LENGTH: 589
<212> TYPE: DNA
<213> ORGANISM: Artificial Sequence

```
<220> FEATURE:
<223> OTHER INFORMATION: WPRE

<400> SEQUENCE: 29
aatcaacctc tggattacaa aatttgtgaa agattgactg gtattcttaa ctatgttgct        60
ccttttacgc tatgtggata cgctgcttta atgcctttgt atcatgctat tgcttcccgt       120
atggctttca ttttctcctc cttgtataaa tcctggttgc tgtctcttta tgaggagttg       180
tggcccgttg tcaggcaacg tggcgtggtg tgcactgtgt ttgctgacgc aacccccact       240
ggttggggca ttgccaccac ctgtcagctc ctttccggga ctttcgcttt ccccctccct       300
attgccacgg cggaactcat cgccgcctgc cttgcccgct gctggacagg ggctcggctg       360
ttgggcactg acaattccgt ggtgttgtcg gggaaatcat cgtcctttcc ttggctgctc       420
gcctgtgttg ccacctggat tctgcgcggg acgtccttct gctacgtccc ttcggccctc       480
aatccagcgg accttccttc ccgcggcctg ctgccggctc tgcggcctct tccgcgtctt       540
cgccttcgcc ctcagacgag tcggatctcc ctttgggccg cctccccgc                   589

<210> SEQ ID NO 30
<211> LENGTH: 7
<212> TYPE: DNA
<213> ORGANISM: Artificial Sequence
<220> FEATURE:
<223> OTHER INFORMATION: BstB1 restriction site and adjacent downstream
      'G'

<400> SEQUENCE: 30 ttcgaag                                                                    7

<210> SEQ ID NO 31
<211> LENGTH: 7012
<212> TYPE: DNA
<213> ORGANISM: Artificial Sequence
<220> FEATURE:
<223> OTHER INFORMATION: Gene therapy vector

<400> SEQUENCE: 31
cacatacgat ttaggtgaca ctatagaata cacggaatta attctagctg cgcgctcgct        60
cgctcactga ggccgcccgg gcaaagcccg ggcgtcgggc gacctttggt cgcccggcct       120
cagtgagcga gcgagcgcgc agagagggag tggccaactc catcactagg ggttccttgt       180
agttaatgat taacccgcca tgctacttat ctacgtagcc atgctctagg tacccagatc       240
ttccccacct agccacctgg caaactgctc cttctctcaa aggcccaaac atggcctccc       300
agactgcaac ccccaggcag tcaggccctg tctccacaac ctcacagcca ccctggacgg       360
aatctgcttc ttcccacatt tgagtcctcc tcagccctg agctcctctg gcagggctg        420 tttctttcca tctttgtatt cccagggggcc tgcaaataaa tgtttaatga acgaacaaga      480
gagtgaattc caattccatg caacaaggat tgggctcctg ggccctaggc tatgtgtctg       540
gcaccagaaa cggaagctgc aggttgcagc ccctgccctc atggagctcc tcctgtcaga       600
ggagtgtggg gactggatga ctccagaggt aacttgtggg ggaacgaaca ggtaaggggc       660
tgtgtgacga gatgagagac tgggagaata aaccagaaag tctctagctg tccagaggac       720
atagcacaga ggcccatggt ccctatttca aacccaggcc accagactga gctgggacct       780
tgggacagac aagtcatgca gaagttaggg gaccttctcc tcccttttcc tggatcctga       840
gtacctctcc tccctgacct caggcttcct cctagtgtca ccttggcccc tcttagaagc       900
caattaggcc ctcagtttct gcagcgggga ttaatatgat tatgaacacc cccaatctcc       960
```

-continued

```
cagatgctga ttcagccagg agcttaggag ggggaggtca cttttataagg gtctgggggg     1020 gtcagaaccc agagtcatcc ggagtcgctg cgcgctgcct tcgccccgtg ccccgctccg     1080
ccgccgcctc gcgccgcccg ccccggctct gactgaccgc gttactccca caggtgagcg     1140
ggcgggacgg cccttctcct ccgggctgta attagcgctt ggtttaatga cggcttgttt     1200
cttttctgtg gctgcgtgaa agccttgagg ggctccggga gggccctttg tgcgggggga     1260
gcggctcggg gctgtccgcg gggggacggc tgccttcggg ggggacgggg cagggcgggg     1320
ttcggcttct ggcgtgtgac cggcggctct agagcctctg ctaaccatgt tcatgccttc     1380 ttcttttttcc tacagctcct gggcaacgtg ctggttattg tgctgtctca tcattttggc     1440
aaagaattgg atcctagctt gattgacggg aactacaaga cccgcgctga agtcaagttc     1500
gaaggtgagg aagttgatgg ggaagttcaa gagacttccc catcaacttc tttctcagtt     1560
ttttctcttt cttttcgaag gtgacaccct ggtgaataga atcgagctga agggcattga     1620
ctttaaggag gattgacggg aactacaaga cccgcgctga agtcaagttc gaaggtagat     1680
gacaaaagac tcgttttcaa gagaaacgag tcttttgtca tttctcagtt ttttctcttt     1740
cttttcgaag gtgacaccct ggtgaataga atcgagctga agggcattga ctttaaggag     1800
gatatcgaat tccgccacca tgaatggcac agaaggccct aacttctacg tgcccttctc     1860
caatgcgacg ggtgtggtac gcagcccctt cgagtaccca cagtactacc tggctgagcc     1920
atggcagttc tccatgctgg ccgcctacat gtttctgctg atcgtgctgg gatttccaat     1980
taattttctg acgctctacg tcaccgtcca gcacaagaag ctgcgcacgc ctctcaacta     2040
catcctgctc aacctagccg tggctgacct cttcatggtc ctaggtggct tcaccagcac     2100
cctctacacc tctctgcatg gatacttcgt cttcgggccc acaggatgca atttggaggg     2160
cttctttgcc accctgggcg gtgaaattgc cctgtggtcc ttggtggtcc tggccatcga     2220
gcggtacgtg gtggtgtgta agcccatgag caacttccgc ttcggggaga accatgccat     2280
catgggcgtt gccttcacct gggtcatggc gctggcctgc gccgcacccc cactcgccgg     2340
ctggtccagg tacatccccg agggcctgca gtgctcgtgt ggaatcgact actacacgct     2400
caagccggag gtcaacaatg aatccttcgt gatttatatg ttcgtggtcc acttcaccat     2460
ccccatgatt atcatctttt tctgctatgg gcagctcgtc ttcaccgtca aggaggccgc     2520
tgcccagcag caggagtcag ccaccacaca gaaggcagag aaggaggtca cccgcatggt     2580
catcatcatg gtcatcgctt tcctgatctg ctgggtgccc tacgccagcg tggcattcta     2640
catcttcacc caccagggct ccaacttcgg tcccatcttc atgaccatcc cagcgttctt     2700
tgccaagagc gccgccatct acaaccctgt catctatatc atgatgaaca agcagttccg     2760
gaactgcatg ctcaccacca tctgctgcgg caagaaccca ctgggtgacg atgaggcctc     2820
tgctaccgtg tccaagacgg agacgagcca ggtggccccg gcctaaaagc ttatcgataa     2880
tcaacctctg gattacaaaa tttgtgaaag attgactggt attcttaact atgttgctcc     2940
ttttacgcta tgtggatacg ctgctttaat gcctttgtat catgctattg cttcccgtat     3000
ggctttcatt ttctcctcct tgtataaatc ctggttgctg tctctttatg aggagttgtg     3060
gcccgttgtc aggcaacgtg gcgtggtgtg cactgtgttt gctgacgcaa ccccactgg     3120 ttggggcatt gccaccacct gtcagctcct ttccgggact ttcgctttcc ccctccctat     3180
tgccacggcg gaactcatcg ccgcctgcct tgcccgctgc tggacagggg ctcggctgtt     3240
gggcactgac aattccgtgg tgttgtcggg gaaatcatcg tcctttcctt ggctgctcgc     3300
```

-continued

```
ctgtgttgcc  acctggattc  tgcgcgggac  gtccttctgc  tacgtccctt  cggccctcaa       3360
tccagcggac  cttccttccc  gcggcctgct  gccggctctg  cggcctcttc  cgcgtcttcg       3420
ccttcgccct  cagacgagtc  ggatctccct  ttgggccgcc  tccccgcatc  gataccgtcg       3480
actcgctgat  cagcctcgac  tgtgccttct  agttgccagc  catctgttgt  ttgcccctcc       3540
cccgtgcctt  ccttgaccct  ggaaggtgcc  actcccactg  tcctttccta  ataaaatgag       3600
gaaattgcat  cgcattgtct  gagtaggtgt  cattctattc  tggggggtgg  ggtggggcag       3660
gacagcaagg  gggaggattg  ggaagacaat  agcaggcatg  ctggggatgc  ggtgggctct       3720
atggcttctg  aggcggaaag  aaccagctgg  ggctcgacta  gagcatggct  acgtagataa       3780
gtagcatggc  gggttaatca  ttaactacaa  ggaacccta   gtgatggagt  tggccactcc       3840
ctctctgcgc  gctcgctcgc  tcactgaggc  cgggcgacca  aaggtcgccc  gacgcccggg       3900
cggcctcagt  gagcgagcga  gcgcgcagag  cttttttgcaa  aagcctaggc  ctccaaaaaa       3960
gcctcctcac  tacttctgga  atagctcaga  ggccgaggcg  gcctcggcct  ctgcataaat       4020
aaaaaaaatt  agtcagccat  ggggcggaga  atggcggaac  tgggcggag   ttaggggcgg       4080 gatgggcgga  gttaggggcg  ggactatggt  tgctgactaa  ttgagatgca  tgctttgcat       4140
acttctgcct  gctggggagc  ctggggactt  tccacacctg  gttgctgact  aattgagatg       4200
catgctttgc  atacttctgc  ctgctgggga  gcctggggac  tttccacacc  ctaactgaca       4260
cacattccac  agctgcatta  atgaatcggc  caacgcgcgg  ggagaggcgg  tttgcgtatt       4320
gggcgctctt  ccgcttcctc  gctcactgac  tcgctgcgct  cggtcgttcg  gctgcggcga       4380
gcggtatcag  ctcactcaaa  ggcggtaata  cggttatcca  cagaatcagg  ggataacgca       4440
ggaaagaaca  tgtgagcaaa  aggccagcaa  aaggccagga  accgtaaaaa  ggccgcgttg       4500
ctggcgtttt  tccataggct  ccgcccccct  gacgagcatc  acaaaaatcg  acgctcaagt       4560
cagaggtggc  gaaacccgac  aggactataa  agataccagg  cgtttccccc  tggaagctcc       4620
ctcgtgcgct  ctcctgttcc  gaccctgccg  cttaccggat  acctgtccgc  ctttctccct       4680
tcgggaagcg  tggcgctttc  tcatagctca  cgctgtaggt  atctcagttc  ggtgtaggtc       4740
gttcgctcca  agctgggctg  tgtgcacgaa  ccccccgttc  agcccgaccg  ctgcgcctta       4800
tccggtaact  atcgtcttga  gtccaacccg  gtaagacacg  acttatcgcc  actggcagca       4860
gccactggta  acaggattag  cagagcgagg  tatgtaggcg  gtgctacaga  gttcttgaag       4920
tggtggccta  actacggcta  cactagaaga  acagtatttg  gtatctgcgc  tctgctgaag       4980
ccagttacct  tcggaaaaag  agttggtagc  tcttgatccg  gcaaacaaac  caccgctggt       5040
agcggtggtt  tttttgtttg  caagcagcag  attacgcgca  gaaaaaaagg  atctcaagaa       5100
gatcctttga  tcttttctac  ggggtctgac  gctcagtgga  acgaaaactc  acgttaaggg       5160
attttggtca  tgagattatc  aaaaaggatc  ttcacctaga  tccttttaaa  ttaaaaatga       5220
agttttaaat  caatctaaag  tatatatgag  taaacttggt  ctgacagtta  ccaatgctta       5280
atcagtgagg  cacctatctc  agcgatctgt  ctatttcgtt  catccatagt  tgcctgactc       5340
cccgtcgtgt  agataactac  gatacgggag  ggcttaccat  ctggccccag  tgctgcaatg       5400
ataccgcgag  acccacgctc  accggctcca  gatttatcag  caataaacca  gccagccgga       5460
agggccgagc  gcagaagtgg  tcctgcaact  ttatccgcct  ccatccagtc  tattaattgt       5520
tgccgggaag  ctagagtaag  tagttcgcca  gttaatagtt  tgcgcaacgt  tgttgccatt       5580
gctacaggca  tcgtggtgtc  acgctcgtcg  tttggtatgg  cttcattcag  ctccggttcc       5640
caacgatcaa  ggcgagttac  atgatccccc  atgttgtgca  aaaaagcggt  tagctccttc       5700
```

-continued

```
ggtcctccga tcgttgtcag aagtaagttg gccgcagtgt tatcactcat ggttatggca    5760
gcactgcata attctcttac tgtcatgcca tccgtaagat gctttctgt gactggtgag     5820 tactcaacca agtcattctg agaatagtgt atgcggcgac cgagttgctc ttgcccggcg    5880
tcaatacggg ataataccgc gccacatagc agaactttaa aagtgctcat cattggaaaa    5940
cgttcttcgg ggcgaaaact ctcaaggatc ttaccgctgt tgagatccag ttcgatgtaa    6000
cccactcgtg cacccaactg atcttcagca tcttttactt tcaccagcgt ttctgggtga    6060
gcaaaaacag gaaggcaaaa tgccgcaaaa aagggaataa gggcgacacg gaaatgttga    6120
atactcatac tcttcctttt tcaatattat tgaagcattt atcagggtta ttgtctcatg    6180
agcggataca tatttgaatg tatttagaaa aataaacaaa taggggttcc gcgcacattt    6240
ccccgaaaag tgccacctga cgtctaagaa accattatta tcatgacatt aacctataaa    6300
aataggcgta tcacgaggcc ctttcgtctc gcgcgtttcg gtgatgacgg tgaaaacctc    6360
tgacacatgc agctcccgga cacggtcaca gcttgtctgt aagcggatgc cgggagcaga    6420
caagcccgtc agggcgcgtc agcgggtgtt ggcgggtgtc ggggctggct taactatgcg    6480
gcatcagagc agattgtact gagagtgcac cattcgacgc tctcccttat gcgactcctg    6540
cattaggaag cagcccagta gtaggttgag gccgttgagc accgccgccg caaggaatgg    6600
tgcatgcaag gagatggcgc ccaacagtcc cccggccacg gggcctgcca ccatacccac    6660
gccgaaacaa gcgctcatga gcccgaagtg gcgagcccga tcttccccat cggtgatgtc    6720
ggcgatatag gcgccagcaa ccgcacctgt ggcgccggtg atgccggcca cgatgcgtcc    6780
ggcgtagagg atctggctag cgatgaccct gctgattggt tcgctgacca tttccgggtg    6840
cgggacggcg ttaccagaaa ctcagaaggt tcgtccaacc aaaccgactc tgacggcagt    6900
ttacgagaga gatgataggg tctgcttcag taagccagat gctacacaat taggcttgta    6960
catattgtcg ttagaacgcg gctacaatta atacataacc ttatgtatca ta            7012
```

```
<210> SEQ ID NO 32
<211> LENGTH: 177
<212> TYPE: DNA
<213> ORGANISM: Artificial Sequence
<220> FEATURE:
<223> OTHER INFORMATION: Forward ITR

<400> SEQUENCE: 32
cacatacgat ttaggtgaca ctatagaata cacggaatta attctagctg cgcgctcgct     60
cgctcactga ggccgcccgg gcaaagcccg ggcgtcgggc gacctttggt cgcccggcct    120
cagtgagcga gcgagcgcgc agagagggag tggccaactc catcactagg ggttcct       177
```

```
<210> SEQ ID NO 33
<211> LENGTH: 137
<212> TYPE: DNA
<213> ORGANISM: Artificial Sequence
<220> FEATURE:
<223> OTHER INFORMATION: Reverse ITR

<400> SEQUENCE: 33 ggaacccta gtgatggagt tggccactcc ctctctgcgc gctcgctcgc tcactgaggc      60
cgggcgacca aaggtcgccc gacgcccggg cggcctcagt gagcgagcga gcgcgcagag    120 cttttttgcaa aagccta                                                  137
```

```
<210> SEQ ID NO 34
```

-continued

```
<211> LENGTH: 806
<212> TYPE: DNA
<213> ORGANISM: Artificial Sequence
<220> FEATURE:
<223> OTHER INFORMATION: Forward ITR human rhodopsin promoter

<400> SEQUENCE: 34
cagatcttcc ccacctagcc acctggcaaa ctgctccttc tctcaaaggc ccaaacatgg        60
cctcccagac tgcaaccccc aggcagtcag gccctgtctc cacaacctca cagccaccct       120
ggacggaatc tgcttcttcc cacatttgag tcctcctcag cccctgagct cctctgggca       180
gggctgtttc tttccatctt tgtattccca ggggcctgca aataaatgtt taatgaacga       240
acaagagagt gaattccaat tccatgcaac aaggattggg ctcctgggcc ctaggctatg       300
tgtctggcac cagaaacgga agctgcaggt tgcagcccct gccctcatgg agctcctcct       360
gtcagaggag tgtggggact ggatgactcc agaggtaact tgtgggggaa cgaacaggta       420
aggggctgtg tgacgagatg agagactggg agaataaacc agaaagtctc tagctgtcca       480
gaggacatag cacagaggcc catggtccct atttcaaacc caggccacca gactgagctg       540
ggaccttggg acagacaagt catgcagaag ttaggggacc ttctcctccc ttttcctgga       600
tcctgagtac ctctcctccc tgacctcagg cttcctccta gtgtcacctt ggcccctctt       660
agaagccaat taggccctca gtttctgcag cggggattaa tatgattatg aacacccca        720 atctcccaga tgctgattca gccaggagct taggaggggg aggtcacttt ataagggtct       780 ggggggggtca gaacccagag tcatcc                                          806

<210> SEQ ID NO 35
<211> LENGTH: 717
<212> TYPE: DNA
<213> ORGANISM: Artificial Sequence
<220> FEATURE:
<223> OTHER INFORMATION: eGFP CDS

<400> SEQUENCE: 35
atgagcaagg gcgaggaact gttcactggc gtggtcccaa ttctcgtgga actggatggc        60
gatgtgaatg gcacaaaatt ttctgtcagc ggagagggtg aaggtgatgc cacatacgga       120
aagctcaccc tgaaattcat ctgcaccact ggaaagctcc ctgtgccatg ccaacactg        180 gtcactaccc tgacctatgg cgtgcagtgc ttttccagat acccagacca tatgaagcag       240
catgactttt tcaagagcgc catgcccgag ggctatgtgc aggagagaac catcttttc        300 aaagatgacg ggaactacaa gacccgcgct gaagtcaagt tcgaaggtga cacccrggtg       360
aatagaatcg agctgaaggg cattgacttt aaggaggatg gaaacattct cggccacaag       420
ctggaataca actataactc ccacaatgtg tacatcatgg ccgacaagca aaagaatggc       480
atcaaggtca acttcaagat cagacacaac attgaggatg gatccgtgca gctggccgac       540
cattatcaac agaacactcc aatcggcgac ggccctgtgc tcctcccaga caaccattac       600
ctgtccaccc agtctgccct gtctaaagat cccaacgaaa agagagacca catggtcctg       660
ctggagtttg tgaccgctgc tgggatcaca catggcatgg acgagctgta caagtga        717

<210> SEQ ID NO 36
<211> LENGTH: 238
<212> TYPE: PRT
<213> ORGANISM: Artificial Sequence
<220> FEATURE:
<223> OTHER INFORMATION: eGFP amino acid

<400> SEQUENCE: 36
```

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 37
<211> LENGTH: 41
<212> TYPE: DNA
<213> ORGANISM: Artificial Sequence
<220> FEATURE:
<223> OTHER INFORMATION: 5' ESE rich sequence

<400> SEQUENCE: 37
tgacgggaac tacaagaccc gcgctgaagt caagttcgaa g                    41

<210> SEQ ID NO 38
<211> LENGTH: 53
<212> TYPE: DNA
<213> ORGANISM: Artificial Sequence
<220> FEATURE:
<223> OTHER INFORMATION: 3' ESE rich sequence

<400> SEQUENCE: 38
gtgacaccct ggtgaataga atcgagctga agggcattga ctttaaggag gat        53

<210> SEQ ID NO 39
<211> LENGTH: 439
<212> TYPE: DNA
<213> ORGANISM: Artificial Sequence
<220> FEATURE:
<223> OTHER INFORMATION: 5'UTR without mirtrons and additional ESE-rich
      sequences

<400> SEQUENCE: 39
ggagtcgctg cgcgctgcct tcgccccgtg ccccgctccg ccgccgcctc gcgccgcccg    60
ccccggctct gactgaccgc gttactccca caggtgagcg ggcgggacgg cccttctcct    120
ccgggctgta attagcgctt ggtttaatga cggcttgttt cttttctgtg gctgcgtgaa    180
agccttgagg ggctccggga gggccctttg tgcggggggga gcggctcggg gctgtccgcg    240
gggggacggc tgccttcggg ggggacgggg caggcgggg ttcggcttct ggcgtgtgac    300
cggcggctct agagcctctg ctaaccatgt tcatgccttc ttcttttttcc tacagctcct    360 gggcaacgtg ctggttattg tgctgtctca tcattttggc aaagaattgg atcctagctt    420
gatatcgaat tccgccacc    439

<210> SEQ ID NO 40
<211> LENGTH: 94
<212> TYPE: DNA
<213> ORGANISM: Artificial Sequence
<220> FEATURE:
<223> OTHER INFORMATION: ESE-rich sequence between tandem mirtrons

<400> SEQUENCE: 40
gtgacaccct ggtgaataga atcgagctga agggcattga ctttaaggag gattgacggg    60
aactacaaga cccgcgctga agtcaagttc gaag    94

<210> SEQ ID NO 41
<211> LENGTH: 76
<212> TYPE: DNA
<213> ORGANISM: Artificial Sequence
<220> FEATURE:
<223> OTHER INFORMATION: Mirtron 1 forward oligonucleotide

<400> SEQUENCE: 41
cgaaggtgga ccacgaacat gtagatttca agagaatcta catgttcgtg gtccctcagt    60
tttttctctt tctttt    76

<210> SEQ ID NO 42
<211> LENGTH: 76
<212> TYPE: DNA
<213> ORGANISM: Artificial Sequence
<220> FEATURE:
<223> OTHER INFORMATION: Mirtron 2 forward oligonucleotide

<400> SEQUENCE: 42
cgaaggtaga gcgtgaggaa gttgatttca agagaatcaa cttcctcacg ctttctcagt    60
tttttctctt tctttt    76

<210> SEQ ID NO 43
<211> LENGTH: 76
<212> TYPE: DNA
<213> ORGANISM: Artificial Sequence
<220> FEATURE:
<223> OTHER INFORMATION: Mirtron 3 forward oligonucleotide

<400> SEQUENCE: 43
cgaaggtgag gaagttgatg gggaagttca agagacttcc ccatcaactt ctttctcagt    60
tttttctctt tctttt    76

<210> SEQ ID NO 44
<211> LENGTH: 76
<212> TYPE: DNA
<213> ORGANISM: Artificial Sequence -continued
<220> FEATURE:
<223> OTHER INFORMATION: Mirtron 4 forward oligonucleotide

<400> SEQUENCE: 44
cgaaggtgac gtagagcgtg aggaagttca agagacttcc tcacgctcta cgttctcagt       60
tttttctctt tctttt                                                       76

<210> SEQ ID NO 45
<211> LENGTH: 76
<212> TYPE: DNA
<213> ORGANISM: Artificial Sequence
<220> FEATURE:
<223> OTHER INFORMATION: Mirtron 5H forward oligonucleotide

<400> SEQUENCE: 45
cgaaggtaga tgacaaaaga ctcgttttca agagaaacga gtcttttgtc atttctcagt       60
tttttctctt tctttt                                                       76

<210> SEQ ID NO 46
<211> LENGTH: 76
<212> TYPE: DNA
<213> ORGANISM: Artificial Sequence
<220> FEATURE:
<223> OTHER INFORMATION: Mirtron 6 forward oligonucleotide

<400> SEQUENCE: 46
cgaaggtgaa gtggaccacg aacatgttca agagacatgt tcgtggtcca ctttctcagt       60
tttttctctt tctttt                                                       76

<210> SEQ ID NO 47
<211> LENGTH: 76
<212> TYPE: DNA
<213> ORGANISM: Artificial Sequence
<220> FEATURE:
<223> OTHER INFORMATION: Mirtron 7 forward oligonucleotide

<400> SEQUENCE: 47
cgaaggtgag catgcagttc cggaacttca agagagttcc ggaactgcat gtttctcagt       60
tttttctctt tctttt                                                       76

<210> SEQ ID NO 48
<211> LENGTH: 76
<212> TYPE: DNA
<213> ORGANISM: Artificial Sequence
<220> FEATURE:
<223> OTHER INFORMATION: Mirtron 1 reverse oligonucleotide

<400> SEQUENCE: 48
cgaaaagaaa gagaaaaaac tgagggacca cgaacatgta gattctcttg aaatctacat       60
gttcgtggtc cacctt                                                       76

<210> SEQ ID NO 49
<211> LENGTH: 76
<212> TYPE: DNA
<213> ORGANISM: Artificial Sequence
<220> FEATURE:
<223> OTHER INFORMATION: Mirtron 2 reverse oligonucleotide

<400> SEQUENCE: 49
cgaaaagaaa gagaaaaaac tgagaaagcg tgaggaagtt gattctcttg aaatcaactt       60
cctcacgctc tacctt                                                       76

-continued

```
<210> SEQ ID NO 50
<211> LENGTH: 76
<212> TYPE: DNA
<213> ORGANISM: Artificial Sequence
<220> FEATURE:
<223> OTHER INFORMATION: Mirtron 3 reverse oligonucleotide

<400> SEQUENCE: 50
cgaaaagaaa gagaaaaaac tgagaaagaa gttgatgggg aagtctcttg aacttcccca      60
tcaacttcct cacctt                                                      76

<210> SEQ ID NO 51
<211> LENGTH: 76
<212> TYPE: DNA
<213> ORGANISM: Artificial Sequence
<220> FEATURE:
<223> OTHER INFORMATION: Mirtron 4 reverse oligonucleotide

<400> SEQUENCE: 51
cgaaaagaaa gagaaaaaac tgagaacgta gagcgtgagg aagtctcttg aacttcctca      60
cgctctacgt cacctt                                                      76

<210> SEQ ID NO 52
<211> LENGTH: 76
<212> TYPE: DNA
<213> ORGANISM: Artificial Sequence
<220> FEATURE:
<223> OTHER INFORMATION: Mirtron 5H reverse oligonucleotide

<400> SEQUENCE: 52
cgaaaagaaa gagaaaaaac tgagaaatga caaaagactc gtttctcttg aaaacgagtc      60
ttttgtcatc tacctt                                                      76

<210> SEQ ID NO 53
<211> LENGTH: 76
<212> TYPE: DNA
<213> ORGANISM: Artificial Sequence
<220> FEATURE:
<223> OTHER INFORMATION: Mirtron 6 reverse oligonucleotide

<400> SEQUENCE: 53
cgaaaagaaa gagaaaaaac tgagaaagtg gaccacgaac atgtctcttg aacatgttcg      60
tggtccactt cacctt                                                      76

<210> SEQ ID NO 54
<211> LENGTH: 76
<212> TYPE: DNA
<213> ORGANISM: Artificial Sequence
<220> FEATURE:
<223> OTHER INFORMATION: Mirtron 7 reverse oligonucleotide

<400> SEQUENCE: 54
cgaaaagaaa gagaaaaaac tgagaaacat gcagttccgg aactctcttg aagttccgga      60
actgcatgct cacctt                                                      76

<210> SEQ ID NO 55
<211> LENGTH: 76
<212> TYPE: DNA
<213> ORGANISM: Artificial Sequence
<220> FEATURE:
<223> OTHER INFORMATION: Mirtron 5M

<400> SEQUENCE: 55
```

-continued gtagatgaca aaggattcgt tttcaagaga aacgaatcct ttgtcatttc tcagtttttt          60
ctctttcttt tcgaag                                                           76

<210> SEQ ID NO 56
<211> LENGTH: 76
<212> TYPE: DNA
<213> ORGANISM: Artificial Sequence
<220> FEATURE:
<223> OTHER INFORMATION: Mirtron 5M forward oligonucleotide

<400> SEQUENCE: 56
cgaaggtaga tgacaaagga ttcgttttca agagaaacga atcctttgtc atttctcagt          60
tttttctctt tctttt                                                           76

<210> SEQ ID NO 57
<211> LENGTH: 76
<212> TYPE: DNA
<213> ORGANISM: Artificial Sequence
<220> FEATURE:
<223> OTHER INFORMATION: Mirtron 5M reverse oligonucleotide

<400> SEQUENCE: 57
cgaaaagaaa gagaaaaaac tgagaaatga caaaggattc gtttctcttg aaaacgaatc          60
ctttgtcatc tacctt                                                           76

<210> SEQ ID NO 58
<211> LENGTH: 76
<212> TYPE: DNA
<213> ORGANISM: Artificial Sequence
<220> FEATURE:
<223> OTHER INFORMATION: Mirtron M2U-M2

<400> SEQUENCE: 58
atagagcgtg aggaagttga tttcaagaga atcaacttcc tcacgctttc tcagtttttt          60
ctctttcttt tcgaag                                                           76

<210> SEQ ID NO 59
<211> LENGTH: 76
<212> TYPE: DNA
<213> ORGANISM: Artificial Sequence
<220> FEATURE:
<223> OTHER INFORMATION: Mirtron M2U-M2 forward oligonucleotide

<400> SEQUENCE: 59
cgaagataga gcgtgaggaa gttgatttca agagaatcaa cttcctcacg ctttctcagt          60
tttttctctt tctttt                                                           76

<210> SEQ ID NO 60
<211> LENGTH: 76
<212> TYPE: DNA
<213> ORGANISM: Artificial Sequence
<220> FEATURE:
<223> OTHER INFORMATION: Mirtron M2U-M2 reverse oligonucleotide

<400> SEQUENCE: 60
cgaaaagaaa gagaaaaaac tgagaaagcg tgaggaagtt gattctcttg aaatcaactt          60
cctcacgctc tatctt                                                           76

<210> SEQ ID NO 61
<211> LENGTH: 76
<212> TYPE: DNA

-continued

```
<213> ORGANISM: Artificial Sequence
<220> FEATURE:
<223> OTHER INFORMATION: Mirtron Scr-M2

<400> SEQUENCE: 61
gtagagatgt ggttgaggat tttcaagaga aatcctcaac cacatctttc tcagtttttt      60
ctctttcttt tcgaag                                                      76

<210> SEQ ID NO 62
<211> LENGTH: 76
<212> TYPE: DNA
<213> ORGANISM: Artificial Sequence
<220> FEATURE:
<223> OTHER INFORMATION: Mirtron Scr-M2 forward oligonucleotide

<400> SEQUENCE: 62
cgaaggtaga gatgtggttg aggattttca agagaaatcc tcaaccacat ctttctcagt      60
tttttctctt tctttt                                                      76

<210> SEQ ID NO 63
<211> LENGTH: 76
<212> TYPE: DNA
<213> ORGANISM: Artificial Sequence
<220> FEATURE:
<223> OTHER INFORMATION: Mirtron Scr-M2 reverse oligonucleotide

<400> SEQUENCE: 63
cgaaaagaaa gagaaaaaac tgagaaagat gtggttgagg atttctcttg aaaatcctca      60
accacatctc tacctt                                                      76

<210> SEQ ID NO 64
<211> LENGTH: 6417
<212> TYPE: DNA
<213> ORGANISM: Artificial Sequence
<220> FEATURE:
<223> OTHER INFORMATION: vector AAV2/8Y733F.RHOp.Ex/Int.M3/M5.RHOM3/5R

<400> SEQUENCE: 64
cacatacgat ttaggtgaca ctatagaata cacggaatta attctagctg cgcgctcgct      60
cgctcactga ggccgcccgg gcaaagcccg ggcgtcgggc gacctttggt cgcccggcct     120
cagtgagcga gcgagcgcgc agagagggag tggccaactc catcactagg ggttccttgt     180
agttaatgat taacccgcca tgctacttat ctacgtagcc atgctctagg tacccagatc     240
ttccccacct agccacctgg caaactgctc cttctctcaa aggcccaaac atggcctccc     300
agactgcaac ccccaggcag tcaggccctg tctccacaac ctcacagcca ccctggacgg     360
aatctgcttc ttcccacatt tgagtcctcc tcagcccctg agctcctctg ggcagggctg     420
tttctttcca tctttgtatt cccaggggcc tgcaaataaa tgtttaatga acgaacaaga     480
gagtgaattc caattccatg caacaaggat tgggctcctg ggccctaggc tatgtgtctg     540
gcaccagaaa cggaagctgc aggttgcagc ccctgccctc atggagctcc tcctgtcaga     600
ggagtgtggg gactggatga ctccagaggt aacttgtggg ggaacgaaca ggtaaggggc     660
tgtgtgacga gatgagagac tgggagaata aaccagaaag tctctagctg tccagaggac     720
atagcacaga ggcccatggt ccctatttca aacccaggcc accagactga gctgggacct     780
tgggacagac aagtcatgca gaagttaggg gaccttctcc tcccttttcc tggatcctga     840
gtacctctcc tccctgacct caggcttcct cctagtgtca ccttggcccc tcttagaagc     900
caattaggcc ctcagtttct gcagcgggga ttaatatgat tatgaacacc cccaatctcc     960
```

```
cagatgctga ttcagccagg agcttaggag ggggaggtca cttttataagg gtctgggggg    1020 gtcagaaccc agagtcatcc ggagtcgctg cgcgctgcct tcgccccgtg ccccgctccg    1080
ccgccgcctc gcgccgcccg ccccggctct gactgaccgc gttactccca caggtgagcg    1140
ggcgggacgg cccttctcct ccgggctgta attagcgctt ggtttaatga cggcttgttt    1200
cttttctgtg gctgcgtgaa agccttgagg ggctccggga gggccctttg tgcgggggga    1260
gcggctcggg gctgtccgcg gggggacggc tgccttcggg ggggacgggg cagggcgggg    1320
ttcggcttct ggcgtgtgac cggcggctct agagcctctg ctaaccatgt tcatgccttc    1380
ttctttttcc tacagctcct gggcaacgtg ctggttattg tgctgtctca tcattttggc    1440
aaagaattgg atcctagctt gattgacggg aactacaaga cccgcgctga agtcaagttc    1500
gaaggtgagg aagttgatgg ggaagttcaa gagacttccc catcaacttc tttctcagtt    1560
ttttctcttt cttttcgaag gtgacaccct ggtgaataga atcgagctga agggcattga    1620
ctttaaggag gattgacggg aactacaaga cccgcgctga agtcaagttc gaaggtagat    1680
gacaaaagac tcgtttttcaa gagaaacgag tcttttgtca tttctcagtt ttttctcttt    1740
cttttcgaag gtgacaccct ggtgaataga atcgagctga agggcattga ctttaaggag    1800
gatatcgaat tccgccacca tgaatggcac agaaggccct aacttctacg tgcccttctc    1860
caatgcgacg ggtgtggtac gcagccccct cgagtaccca cagtactacc tggctgagcc    1920
atggcagttc tccatgctgg ccgcctacat gtttctgctg atcgtgctgg gatttccaat    1980
taattttctg acgctctacg tcaccgtcca gcacaagaag ctgcgcacgc ctctcaacta    2040
catcctgctc aacctagccg tggctgacct cttcatggtc ctaggtggct tcaccagcac    2100
cctctacacc tctctgcatg gatacttcgt cttcgggccc acaggatgca atttggaggg    2160
cttctttgcc accctgggcg gtgaaattgc cctgtggtcc ttggtggtcc tggccatcga    2220
gcggtacgtg gtggtgtgta gcccatgag caacttccgc ttcggggaga accatgccat    2280
catgggcgtt gccttcacct gggtcatggc gctggcctgc gccgcacccc cactcgccgg    2340
ctggtccagg tacatccccg agggcctgca gtgctcgtgt ggaatcgact actacacgct    2400
caagccggag gtcaacaatg aatccttcgt gatttatatg ttcgtggtcc acttcaccat    2460
ccccatgatt atcatcttttt tctgctatgg gcagctcgtc ttcaccgtca aggaggccgc    2520
tgcccagcag caggagtcag ccaccacaca gaaggcagag aaggaggtca cccgcatggt    2580
catcatcatg gtcatcgctt tcctgatctg ctgggtgccc tacgccagcg tggcattcta    2640
catcttcacc caccagggct ccaacttcgg tcccatcttc atgaccatcc cagcgttctt    2700
tgccaagagc gccgccatct acaaccctgt catctatatc atgatgaaca agcagttccg    2760
gaactgcatg ctcaccacca tctgctgcgg caagaaccca ctgggtgacg atgaggcctc    2820
tgctaccgtg tccaagacgg agacgagcca ggtggccccg gcctaaaagc ttatcgatac    2880
cgtcgactcg ctgatcagcc tcgactgtgc cttctagttg ccagccatct gttgtttgcc    2940 cctccccgt gccttccttg accctggaag gtgccactcc cactgtcctt tcctaataaa    3000
atgaggaaat tgcatcgcat tgtctgagta ggtgtcattc tattctgggg ggtggggtgg    3060
ggcaggacag caagggggag gattgggaag acaatagcag gcatgctggg gatgcggtgg    3120
gctctatggc ttctgaggcg gaaagaacca gctgggggctc gactagagca tggctacgta    3180
gataagtagc atggcgggtt aatcattaac tacaaggaac ccctagtgat ggagttggcc    3240
actccctctc tgcgcgctcg ctcgctcact gaggccgggc gaccaaaggt cgcccgacgc    3300
```

-continued

```
ccgggcggcc tcagtgagcg agcgagcgcg cagagctttt tgcaaaagcc taggcctcca   3360
aaaaagcctc ctcactactt ctggaatagc tcagaggccg aggcggcctc ggcctctgca   3420
taaataaaaa aaattagtca gccatggggc ggagaatggg cggaactggg cggagttagg   3480
ggcgggatgg gcggagttag gggcgggact atggttgctg actaattgag atgcatgctt   3540
tgcatacttc tgcctgctgg ggagcctggg gactttccac acctggttgc tgactaattg   3600
agatgcatgc tttgcatact ctgcctgct ggggagcctg gggactttcc acaccctaac   3660
tgacacacat tccacagctg cattaatgaa tcggccaacg cgcggggaga ggcggtttgc   3720
gtattgggcg ctcttccgct tcctcgctca ctgactcgct gcgctcggtc gttcggctgc   3780
ggcgagcggt atcagctcac tcaaaggcgg taatacggtt atccacagaa tcaggggata   3840
acgcaggaaa gaacatgtga gcaaaaggcc agcaaaaggc caggaaccgt aaaaaggccg   3900
cgttgctggc gttttttccat aggctccgcc ccctgacga gcatcacaaa aatcgacgct   3960
caagtcagag gtggcgaaac ccgacaggac tataaagata ccaggcgttt ccccctggaa   4020
gctccctcgt gcgctctcct gttccgaccc tgccgcttac cggatacctg tccgcctttc   4080
tcccttcggg aagcgtggcg ctttctcata gctcacgctg taggtatctc agttcggtgt   4140
aggtcgttcg ctccaagctg ggctgtgtgc acgaacccccc cgttcagccc gaccgctgcg   4200
ccttatccgg taactatcgt cttgagtcca acccggtaag acacgactta tcgccactgg   4260
cagcagccac tggtaacagg attagcagag cgaggtatgt aggcggtgct acagagttct   4320
tgaagtggtg gcctaactac ggctacacta gaagaacagt atttggtatc tgcgctctgc   4380
tgaagccagt taccttcgga aaaagagttg gtagctcttg atccggcaaa caaaccaccg   4440
ctggtagcgg tggtttttttt gtttgcaagc agcagattac gcgcagaaaa aaaggatctc   4500
aagaagatcc tttgatcttt tctacggggt ctgacgctca gtggaacgaa aactcacgtt   4560
aagggatttt ggtcatgaga ttatcaaaaa ggatcttcac ctagatcctt ttaaattaaa   4620
aatgaagttt taaatcaatc taaagtatat atgagtaaac ttggtctgac agttaccaat   4680
gcttaatcag tgaggcacct atctcagcga tctgtctatt tcgttcatcc atagttgcct   4740
gactccccgt cgtgtagata actacgatac gggagggctt accatctggc cccagtgctg   4800
caatgatacc gcgagaccca cgctcaccgg ctccagattt atcagcaata aaccagccag   4860
ccggaagggc cgagcgcaga agtggtcctg caactttatc cgcctccatc cagtctatta   4920
attgttgccg ggaagctaga gtaagtagtt cgccagttaa tagtttgcgc aacgttgttg   4980
ccattgctac aggcatcgtg gtgtcacgct cgtcgtttgg tatggcttca ttcagctccg   5040
gttcccaacg atcaaggcga gttacatgat cccccatgtt gtgcaaaaaa gcggttagct   5100
ccttcggtcc tccgatcgtt gtcagaagta agttggccgc agtgttatca ctcatggtta   5160
tggcagcact gcataattct cttactgtca tgccatccgt aagatgcttt tctgtgactg   5220
gtgagtactc aaccaagtca ttctgagaat agtgtatgcg cgaccgagt tgctcttgcc   5280 cggcgtcaat acgggataat accgcgccac atagcagaac tttaaaagtg ctcatcattg   5340
gaaaacgttc ttcggggcga aaactctcaa ggatcttacc gctgttgaga tccagttcga   5400
tgtaacccac tcgtgcaccc aactgatctt cagcatcttt tactttcacc agcgtttctg   5460
ggtgagcaaa aacaggaagg caaaatgccg caaaaaaggg aataagggcg acacggaaat   5520
gttgaatact catactcttc ctttttcaat attattgaag catttatcag ggttattgtc   5580
tcatgagcgg atacatattt gaatgtattt agaaaaataa acaaataggg gttccgcgca   5640
catttccccg aaaagtgcca cctgacgtct aagaaaccat tattatcatg acattaacct   5700
```

-continued

```
ataaaaatag gcgtatcacg aggcccttc gtctcgcgcg tttcggtgat gacggtgaaa    5760
acctctgaca catgcagctc ccggagacgg tcacagcttg tctgtaagcg gatgccggga    5820
gcagacaagc ccgtcagggc gcgtcagcgg gtgttggcgg gtgtcggggc tggcttaact    5880
atgcggcatc agagcagatt gtactgagag tgcaccattc gacgctctcc cttatgcgac    5940
tcctgcatta ggaagcagcc cagtagtagg ttgaggccgt tgagcaccgc cgccgcaagg    6000
aatggtgcat gcaaggagat ggcgcccaac agtcccccgg ccacggggcc tgccaccata    6060
cccacgccga aacaagcgct catgagcccg aagtggcgag cccgatcttc cccatcggtg    6120
atgtcggcga tataggcgcc agcaaccgca cctgtggcgc cggtgatgcc ggccacgatg    6180
cgtccggcgt agaggatctg gctagcgatg accctgctga ttggttcgct gaccatttcc    6240
gggtgcggga cggcgttacc agaaactcag aaggttcgtc caaccaaacc gactctgacg    6300
gcagtttacg agagagatga tagggtctgc ttcagtaagc cagatgctac acaattaggc    6360
ttgtacatat tgtcgttaga acgcggctac aattaataca taaccttatg tatcata     6417
```

```
<210> SEQ ID NO 65
<211> LENGTH: 6417
<212> TYPE: DNA
<213> ORGANISM: Artificial Sequence
<220> FEATURE:
<223> OTHER INFORMATION: AAV2/8Y733F.RHOp.Ex/Int.M3/M5M.RHOM3/5R

<400> SEQUENCE: 65
```

```
cacatacgat ttaggtgaca ctatagaata cacggaatta attctagctg cgcgctcgct     60
cgctcactga ggccgcccgg gcaaagcccg ggcgtcgggc gacctttggt cgcccggcct    120
cagtgagcga gcgagcgcgc agagagggag tggccaactc catcactagg ggttccttgt    180
agttaatgat taacccgcca tgctacttat ctacgtagcc atgctctagg tacccagatc    240
ttccccacct agccacctgg caaactgctc cttctctcaa aggcccaaac atggcctccc    300
agactgcaac ccccaggcag tcaggccctg tctccacaac ctcacagcca ccctggacgg    360
aatctgcttc ttcccacatt tgagtcctcc tcagcccctg agctcctctg ggcagggctg    420
tttctttcca tctttgtatt cccaggggcc tgcaaataaa tgtttaatga acgaacaaga    480
gagtgaattc caattccatg caacaaggat tgggctcctg ggccctaggc tatgtgtctg    540
gcaccagaaa cggaagctgc aggttgcagc ccctgccctc atggagctcc tcctgtcaga    600
ggagtgtggg gactggatga ctccagaggt aacttgtggg ggaacgaaca ggtaaggggc    660
tgtgtgacga gatgagagac tgggagaata aaccagaaag tctctagctg tccagaggac    720
atagcacaga ggcccatggt ccctatttca aacccaggcc accagactga gctgggacct    780
tgggacagac aagtcatgca gaagttaggg gaccttctcc tcccttttcc tggatcctga    840
gtacctctcc tccctgacct caggcttcct cctagtgtca ccttggcccc tcttagaagc    900
caattaggcc ctcagtttct gcagcggga ttaatatgat tatgaacacc cccaatctcc    960
cagatgctga ttcagccagg agcttaggag ggggaggtca ctttataagg gtctgggggg    1020
gtcagaaccc agagtcatcc ggagtcgctg cgcgctgcct tcgccccgtg ccccgctccg    1080
ccgccgcctc gcgccgcccg ccccggctct gactgaccgc gttactccca caggtgagcg    1140
ggcgggacgg cccttctcct ccgggctgta attagcgctt ggtttaatga cggcttgttt    1200
cttttctgtg gctgcgtgaa agccttgagg ggctccggga gggcccttg tgcggggga     1260 gcggctcggg gctgtccgcg gggggacggc tgccttcggg ggggacgggg cagggcgggg    1320
```

-continued

```
ttcggcttct ggcgtgtgac cggcggctct agagcctctg ctaaccatgt tcatgccttc      1380
ttctttttcc tacagctcct gggcaacgtg ctggttattg tgctgtctca tcattttggc      1440
aaagaattgg atcctagctt gattgacggg aactacaaga cccgcgctga agtcaagttc      1500
gaaggtgagg aagttgatgg ggaagttcaa gagacttccc catcaacttc tttctcagtt      1560
ttttctcttt cttttcgaag gtgacaccct ggtgaataga atcgagctga agggcattga      1620
ctttaaggag gattgacggg aactacaaga cccgcgctga agtcaagttc gaaggtagat      1680
gacaaaggat tcgtttttcaa gagaaacgaa tcctttgtca tttctcagtt ttttctcttt     1740
cttttcgaag gtgacaccct ggtgaataga atcgagctga agggcattga ctttaaggag      1800
gatatcgaat tccgccacca tgaatggcac agaaggccct aacttctacg tgcccttctc      1860
caatgcgacg ggtgtggtac gcagcccctt cgagtaccca cagtactacc tggctgagcc      1920
atggcagttc tccatgctgg ccgcctacat gtttctgctg atcgtgctgg gatttccaat      1980
taattttctg acgctctacg tcaccgtcca gcacaagaag ctgcgcacgc ctctcaacta      2040
catcctgctc aacctagccg tggctgacct cttcatggtc ctaggtggct tcaccagcac      2100
cctctacacc tctctgcatg gatacttcgt cttcgggccc acaggatgca atttggaggg      2160
cttctttgcc accctgggcg gtgaaattgc cctgtggtcc ttggtggtcc tggccatcga      2220
gcggtacgtg gtggtgtgta agcccatgag caacttccgc ttcggggaga accatgccat      2280
catgggcgtt gccttcacct gggtcatggc gctggcctgc gccgcacccc cactcgccgg      2340
ctggtccagg tacatccccg agggcctgca gtgctcgtgt ggaatcgact actacacgct      2400
caagccggag gtcaacaatg aatccttcgt gatttatatg ttcgtggtcc acttcaccat      2460
ccccatgatt atcatctttt tctgctatgg gcagctcgtc ttcaccgtca aggaggccgc      2520
tgcccagcag caggagtcag ccaccacaca gaaggcagag aaggaggtca cccgcatggt      2580
catcatcatg gtcatcgctt tcctgatctg ctgggtgccc tacgccagcg tggcattcta      2640
catcttcacc caccagggct ccaacttcgg tcccatcttc atgaccatcc cagcgttctt      2700
tgccaagagc gccgccatct acaaccctgt catctatatc atgatgaaca agcagttccg      2760
gaactgcatg ctcaccacca tctgctgcgg caagaaccca ctgggtgacg atgaggcctc      2820
tgctaccgtg tccaagacgg agacgagcca ggtggccccg gcctaaaagc ttatcgatac      2880
cgtcgactcg ctgatcagcc tcgactgtgc cttctagttg ccagccatct gttgtttgcc      2940
cctcccccgt gccttccttg accctggaag gtgccactcc cactgtcctt tcctaataaa      3000
atgaggaaat tgcatcgcat tgtctgagta ggtgtcattc tattctgggg ggtggggtgg      3060
ggcaggacag caagggggag gattgggaag acaatagcag gcatgctggg gatgcggtgg      3120
gctctatggc ttctgaggcg gaaagaacca gctggggctc gactagagca tggctacgta      3180
gataagtagc atggcgggtt aatcattaac tacaaggaac ccctagtgat ggagttggcc      3240
actccctctc tgcgcgctcg ctcgctcact gaggccgggc gaccaaaggt cgcccgacgc      3300
ccgggcggcc tcagtgagcg agcgagcgcg cagagctttt tgcaaaagcc taggcctcca      3360
aaaaagcctc ctcactactt ctggaatagc tcagaggccg aggcggcctc ggcctctgca      3420
taaataaaaa aaattagtca gccatggggc ggagaatggg cggaactggg cggagttagg      3480
ggcgggatgg gcggagttag gggcgggact atggttgctg actaattgag atgcatgctt      3540
tgcatacttc tgcctgctgg ggagcctggg gactttccac acctggttgc tgactaattg      3600
agatgcatgc tttgcatact tctgcctgct ggggagcctg gggactttcc acaccctaac      3660
tgacacacat tccacagctg cattaatgaa tcggccaacg cgcggggaga ggcggtttgc      3720
```

-continued

```
gtattgggcg ctcttccgct tcctcgctca ctgactcgct gcgctcggtc gttcggctgc      3780
ggcgagcggt atcagctcac tcaaaggcgg taatacggtt atccacagaa tcaggggata      3840
acgcaggaaa gaacatgtga gcaaaaggcc agcaaaaggc caggaaccgt aaaaaggccg      3900
cgttgctggc gtttttccat aggctccgcc cccctgacga gcatcacaaa aatcgacgct      3960
caagtcagag gtggcgaaac ccgacaggac tataaagata ccaggcgttt ccccctggaa      4020
gctccctcgt gcgctctcct gttccgaccc tgccgcttac cggatacctg tccgcctttc      4080
tcccttcggg aagcgtggcg ctttctcata gctcacgctg taggtatctc agttcggtgt      4140
aggtcgttcg ctccaagctg ggctgtgtgc acgaaccccc cgttcagccc gaccgctgcg      4200
ccttatccgg taactatcgt cttgagtcca acccggtaag acacgactta tcgccactgg      4260
cagcagccac tggtaacagg attagcagag cgaggtatgt aggcggtgct acagagttct      4320
tgaagtggtg gcctaactac ggctacacta agaacagt atttggtatc tgcgctctgc      4380
tgaagccagt taccttcgga aaaagagttg gtagctcttg atccggcaaa caaaccaccg      4440
ctggtagcgg tggtttttttt gtttgcaagc agcagattac gcgcagaaaa aaaggatctc      4500
aagaagatcc tttgatcttt tctacggggt ctgacgctca gtggaacgaa aactcacgtt      4560
aagggatttt ggtcatgaga ttatcaaaaa ggatcttcac ctagatcctt ttaaattaaa      4620
aatgaagttt taaatcaatc taaagtatat atgagtaaac ttggtctgac agttaccaat      4680
gcttaatcag tgaggcacct atctcagcga tctgtctatt tcgttcatcc atagttgcct      4740
gactccccgt cgtgtagata actacgatac gggagggctt accatctggc cccagtgctg      4800
caatgatacc gcgagaccca cgctcaccgg ctccagattt atcagcaata aaccagccag      4860
ccggaagggc cgagcgcaga agtggtcctg caactttatc cgcctccatc cagtctatta      4920
attgttgccg ggaagctaga gtaagtagtt cgccagttaa tagtttgcgc aacgttgttg      4980
ccattgctac aggcatcgtg gtgtcacgct cgtcgtttgg tatggcttca ttcagctccg      5040
gttcccaacg atcaaggcga gttacatgat cccccatgtt gtgcaaaaaa gcggttagct      5100
ccttcggtcc tccgatcgtt gtcagaagta agttggccgc agtgttatca ctcatggtta      5160
tggcagcact gcataattct cttactgtca tgccatccgt aagatgcttt tctgtgactg      5220
gtgagtactc aaccaagtca ttctgagaat agtgtatgcg gcgaccgagt tgctcttgcc      5280
cggcgtcaat acgggataat accgcgccac atagcagaac tttaaaagtg ctcatcattg      5340
gaaaacgttc ttcggggcga aaactctcaa ggatcttacc gctgttgaga tccagttcga      5400
tgtaacccac tcgtgcaccc aactgatctt cagcatcttt tactttcacc agcgtttctg      5460
ggtgagcaaa aacaggaagg caaaatgccg caaaaaaggg aataagggcg acacggaaat      5520
gttgaatact catactcttc cttttttcaat attattgaag catttatcag ggttattgtc      5580
tcatgagcgg atacatattt gaatgtattt agaaaaataa acaaataggg gttccgcgca      5640
catttccccg aaaagtgcca cctgacgtct aagaaaccat tattatcatg acattaacct      5700
ataaaaatag gcgtatcacg aggccctttc gtctcgcgcg tttcggtgat gacggtgaaa      5760
acctctgaca catgcagctc ccggagacgg tcacagcttg tctgtaagcg gatgccggga      5820
gcagacaagc ccgtcagggc gcgtcagcgg gtgttggcgg gtgtcggggc tggcttaact      5880
atgcggcatc agagcagatt gtactgagag tgcaccattc gacgctctcc cttatgcgac      5940
tcctgcatta ggaagcagcc cagtagtagg ttgaggccgt tgagcaccgc cgccgcaagg      6000
aatggtgcat gcaaggagat ggcgcccaac agtcccccgg ccacgggcc tgccaccata      6060
```

-continued

```
cccacgccga aacaagcgct catgagcccg aagtggcgag cccgatcttc cccatcggtg      6120
atgtcggcga tataggcgcc agcaaccgca cctgtggcgc cggtgatgcc ggccacgatg      6180
cgtccggcgt agaggatctg gctagcgatg accctgctga ttggttcgct gaccatttcc      6240
gggtgcggga cggcgttacc agaaaactcag aaggttcgtc caaccaaacc gactctgacg      6300
gcagtttacg agagagatga tagggtctgc ttcagtaagc cagatgctac acaattaggc      6360
ttgtacatat tgtcgttaga acgcggctac aattaataca taaccttatg tatcata       6417
```

<210> SEQ ID NO 66
<211> LENGTH: 31
<212> TYPE: DNA
<213> ORGANISM: Artificial Sequence
<220> FEATURE:
<223> OTHER INFORMATION: 5' ESE rich sequence

<400> SEQUENCE: 66

```
tacaagaccc gcgctgaagt caagttcgaa g                                    31
```

<210> SEQ ID NO 67
<211> LENGTH: 160
<212> TYPE: DNA
<213> ORGANISM: Artificial Sequence
<220> FEATURE:
<223> OTHER INFORMATION: 5'UTR insert (eGFP - M3 - eGFP - M5 - eGFP)

<400> SEQUENCE: 67

```
tacaagaccc gcgctgaagt caagttcgaa ggtgaggaag ttgatgggga agttcaagag      60
acttccccat caacttcttt ctcagttttt tctctttctt ttcgaaggtg acaccctggt     120
gaatagaatc gagctgaagg gcattgactt taaggaggat                           160
```

<210> SEQ ID NO 68
<211> LENGTH: 27
<212> TYPE: DNA
<213> ORGANISM: Artificial Sequence
<220> FEATURE:
<223> OTHER INFORMATION: 5' ESE rich sequence

<400> SEQUENCE: 68

```
agacccgcgc tgaagtcaag ttcgaag                                         27
```

<210> SEQ ID NO 69
<211> LENGTH: 58
<212> TYPE: DNA
<213> ORGANISM: Artificial Sequence
<220> FEATURE:
<223> OTHER INFORMATION: 3' ESE rich sequence

<400> SEQUENCE: 69

```
gtgacaccct ggtgaataga atcgagctga agggcattga ctttaaggag gatatcga       58
```

<210> SEQ ID NO 70
<211> LENGTH: 161
<212> TYPE: DNA
<213> ORGANISM: Artificial Sequence
<220> FEATURE:
<223> OTHER INFORMATION: 5'UTR insert (eGFP - M3 - eGFP - M5 - eGFP)

<400> SEQUENCE: 70

```
agacccgcgc tgaagtcaag ttcgaaggta gatgacaaaa gactcgtttt caagagaaac      60
gagtcttttg tcatttctca gtttttttctc tttcttttcg aaggtgacac cctggtgaat     120
agaatcgagc tgaagggcat tgactttaag gaggatatcg a                         161
```

-continued

```
<210> SEQ ID NO 71
<211> LENGTH: 5
<212> TYPE: PRT
<213> ORGANISM: Artificial Sequence
<220> FEATURE:
<223> OTHER INFORMATION: APVAT link peptide

<400> SEQUENCE: 71

Ala Pro Val Ala Thr
1               5
```